US011390613B2

(12) United States Patent
Hadden

(10) Patent No.: US 11,390,613 B2
(45) Date of Patent: Jul. 19, 2022

(54) AZOLE ANALOGUES AND METHODS OF USE THEREOF

(71) Applicant: UNIVERSITY OF CONNECTICUT, Farmington, CT (US)

(72) Inventor: Matthew Kyle Hadden, Ellington, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 48 days.

(21) Appl. No.: 16/639,242

(22) PCT Filed: Aug. 20, 2018

(86) PCT No.: PCT/US2018/047070
§ 371 (c)(1),
(2) Date: Feb. 14, 2020

(87) PCT Pub. No.: WO2019/040363
PCT Pub. Date: Feb. 28, 2019

(65) Prior Publication Data
US 2020/0317649 A1 Oct. 8, 2020

Related U.S. Application Data

(60) Provisional application No. 62/547,853, filed on Aug. 20, 2017.

(51) Int. Cl.
*C07D 405/14* (2006.01)
*A61P 35/00* (2006.01)
*A61K 47/38* (2006.01)
*C07D 405/12* (2006.01)

(52) U.S. Cl.
CPC ............ *C07D 405/14* (2013.01); *A61K 47/38* (2013.01); *A61P 35/00* (2018.01); *C07D 405/12* (2013.01)

(58) Field of Classification Search
None
See application file for complete search history.

(56) References Cited

U.S. PATENT DOCUMENTS

| | | | |
|---|---|---|---|
| 4,456,605 A | 6/1984 | Heeres et al. | |
| 4,619,931 A | 10/1986 | Heeres et al. | |
| 4,791,111 A | 12/1988 | Herres et al. | |
| 5,075,309 A | 12/1991 | Heeres et al. | |
| 5,693,626 A * | 12/1997 | Saksena | C07D 231/12 514/85 |
| 6,384,030 B1 | 5/2002 | Meerpoel et al. | |
| 6,881,745 B2 | 4/2005 | Hayes et al. | |
| 8,771,739 B2 | 7/2014 | Hayes et al. | |
| 8,921,374 B2 | 12/2014 | Mudge et al. | |
| 9,650,365 B2 | 5/2017 | Hadden et al. | |
| 9,839,636 B2 | 12/2017 | Hadden et al. | |
| 2009/0203713 A1 | 8/2009 | Beachy et al. | |
| 2012/0283194 A1 | 11/2012 | Atwood et al. | |
| 2016/0340346 A1 | 11/2016 | Hadden et al. | |
| 2017/0209436 A1 | 7/2017 | Hadden et al. | |

FOREIGN PATENT DOCUMENTS

| | | |
|---|---|---|
| EP | 1886695 A1 | 2/2008 |
| WO | 9315719 A1 | 8/1993 |
| WO | 2009110955 A2 | 9/2009 |
| WO | 2013036866 A1 | 3/2013 |
| WO | 2015116947 A1 | 8/2015 |
| WO | 2016094570 A1 | 6/2016 |
| WO | 2015116947 | 8/2016 |
| WO | 2018178338 A1 | 10/2018 |
| WO | 2019040363 A1 | 2/2019 |

OTHER PUBLICATIONS

Saksena et al., Bioorganic & Medicinal Chemistry (1995), 5(2), pp. 127-132.*
Extended European Search Report issued in Application No. 18847496.9 dated Mar. 15, 2021, 8 pages.
Banerjee et al.; "Evaluation of vitamin D3 A-ring analogues as Hedgehog pathway inhibitors"; Bioorg. Med. Chem. Lett. 2012, 22 (3), 1330-1334.
Brun et al.; "Survivin as a therapeutic target in Sonic hedgehog-driven medulloblastoma"; Oncogene 2015, 34 (29), 3770-3779.
Costa et al.; "Liposome Formation Using a Coaxial Turbulent Jet in Co-Flow"; Pharm Res; 33(2); pp. 404-416; (2016).
Heeres et al.; "Antimycotic Azoles. 7. Synthesis and Antifungal Properties of a Series of Novel Triazol-3-ones"; J. Med. Chem. 1984, 27 (7), 894-900.
Mishra et al.; "Radiation Damage of Myoglobin Crystals in Weak Stationary Electric and Magnetic Fields"; J. Phys. Conf. Ser. 2014, 534(1), 1-8.
Shi et al.; "Impact of Absolute Stereochemistry on the Antiangiogenic and Antifungal Activities of Itraconazole"; ACS Medicinal Chemistry Letters, 2010, 1 (4), 155-159.
Shi et al; Itraconazole Side Chain Analogues: Structure-Act. Relationship Studies for Inh. of Engothelial Cell Proliferation, Vascular Endothelial Growth Factor Receptor 2 (VEGFR2) Glycosylation, & Hedehog Signaling, J. Med. Chem. 2011, 54:20, 7363-74.
Tanoury et al.; Total synthesis of (2R,4S,2,S,3,R)-hydroxyitraconazole: implementations of a recycle protocol and a mild and safe phase-transfer reagent for preparation of the key chiral units; Tetrahedron: Asymmetry 2003, 14 (22), 3487-3493.
Pondugula, Satyanarayana R. et al.; "Pregnane X Receptor and Cancer: Context-Specificity is Key"; Nuclear Receptor Research, vol. 3, (2016), Article ID 101198, 12 pages.
Power, Eoin C. et al.; "Partial structures of ketoconazole as modulators of the large conductance calcium-activated potassium channel (BKCa)"; Bioorganic & Medicinal Chemistry Letters 16 (2006) 887-890.

(Continued)

*Primary Examiner* — Brian J Davis
(74) *Attorney, Agent, or Firm* — Cantor Colburn LLP

(57) ABSTRACT

Disclosed herein are analogues of itraconazole that are both angiogenesis and hedgehog signaling pathway inhibitors, formulations thereof, including liposome formulations thereof. The compounds are expected to be useful in the treatment of cell proliferation disorders such as cancer, particularly cancers that are dependent upon the hedgehog signaling pathway such as basal cell carcinoma and medulloblastoma.

27 Claims, No Drawings

(56) References Cited

OTHER PUBLICATIONS

Wen, Jiachen et al.; "Truncated Itraconazole Analogues Exhibiting Potent Anti-Hedgehog Activity and Improved Drug-like Properties". ACS Med. Chem. Lett. 2019, 10, 1290-1295.
Chen et al.; "Posaconazole, a Second-Generation Triazole Antifungal Drug, Inhibits the Hedgehog Signaling Pathway and Progression of Basal Cell Carcinoma"; Molecular Cancer Therapeutics; 15(5); pp. 866-876; (2006).
Chong et al.; "Inhibition of Angiogenesis by the Antifungal Drug Itraconazole"; ASC Chemical Biology: 2(4); pp. 263-270; (2007).
International Search Report and Written Opinion; International Application No. PCT/US15/13808; International Filing Date Jan. 30, 2015; dated Apr. 9, 2015; 9 pages.
International Search Report for PCT/US2018/47070 for International Filing Date Aug. 20, 2018, dated Jan. 2, 2019, 6 pages.
Pace et al.; "Repurposing the Clinically Efficacious Antifungal Agent Itraconazole as an Anticancer Chemotherapeutic"; Journal of Medicinal Chemistry; 59; pp. 3635-3649; (2016).
Written Opinion for PCT/US2018/47070 for International Filing Date Aug. 20, 2018, dated Jan. 2, 2019, 7 pages.

* cited by examiner

AZOLE ANALOGUES AND METHODS OF USE THEREOF

CROSS-REFERENCE TO RELATED APPLICATIONS

This application is a U.S. National Stage entry of International Application No. PCT/US2018/047070, filed Aug. 20, 2018, which claims the benefit of U.S. Provisional Application 62/547,853, filed Aug. 20, 2017, each of which is incorporated herein by reference in its entirety.

STATEMENT REGARDING FEDERALLY SPONSORED RESEARCH & DEVELOPMENT

This invention was made with government support under Grant #CA190617 awarded by the National Institutes of Health. The government has certain rights in the invention.

FIELD OF THE DISCLOSURE

The present disclosure is related to novel azole-based compounds having utility as anti-proliferative agents, specifically novel derivatives of azole antifungals.

BACKGROUND

Hh signaling is essential to embryonic development by regulating the proliferation and differentiation of cells in a time-dependent and positional manner. Inappropriate activation of the Hedgehog (Hh) signaling pathway has been implicated in many cancers such as basal cell carcinoma and medulloblastoma. As a result, the Hh signaling pathway has emerged as a promising target for drug intervention. Itraconazole and posaconazole are azole antifungals that have previously been identified as Hh inhibitors with the ability to decrease tumor growth in models of Hh-dependent basal cell carcinoma and medulloblastoma.

The Hh pathway is a developmental signaling pathway that plays a key role in directing growth and tissue patterning during embryonic development. Dysregulation of Hh signaling has been linked to the development of a variety of human tumors; most notably, basal cell carcinoma (BCC) and medulloblastoma (MB). Recent years have seen the development of numerous small molecule Hh pathway inhibitors, the majority of which directly bind Smoothened (SMO), a 7-transmembrane GPCR-like receptor and key regulator of pathway signaling. Two Hh pathway inhibitors that target Smoothened (Smo) are approved for treatment of metastatic BCC (Vismodegib and Sonidegib). Clinically relevant resistance in BCC and MB is due to point mutations in Smo that prevents binding of the drug. The importance of angiogenesis in tumor formation, growth, and metastasis is well-documented and numerous small molecules and biologics that inhibit angiogenesis are clinically useful anti-cancer agents.

Itraconazole (ITZ) is a clinically efficacious anti-fungal drug that was recently identified as an Hh pathway inhibitor (IC50=690 nM). ITZ maintains potent anti-Hh activity in vitro and in vivo in the presence of all resistant forms of mutant Smo it has been tested against. In both in vitro and in vivo studies, ITZ significantly decreased tumor growth in murine models of Hh-dependent BCC and MB.

Posaconazole (PSZ) also inhibited Hh signaling in the murine BCC cell line, ASZ, with an IC50 value of 540 nM. PSZ is metabolically more stable than ITZ and like ITZ maintains Hh-inhibition even in the presence of mutant Smo.

While itraconazole has anti-proliferative activity, it can have serious detrimental interactions with other commonly taken medications such as anticoagulants, statins and calcium channel blockers. While clinically approved, PSZ suffers from several undesirable properties such as poor solubility, high efflux, and unfavorable drug-drug interactions due to its ability to inhibit CYP3A4. It is thus desirable to provide alternatives to itraconazole and posaconazole that maintain the anti-proliferative properties, but that potentially do not have the side-effects observed from these two compounds.

BRIEF SUMMARY

In an embodiment, a compound of the structure of Formula (I)

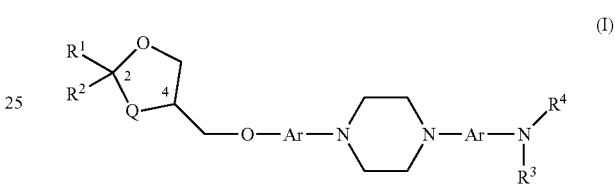

wherein
Q is O or $CH_2$;
each Ar is independently unsubstituted or substituted aryl;
$R^1$ is $C_{1-6}$ alkyl optionally substituted with an amino ($-NH_2$), a $C_{1-6}$ alkylamino, a $C_{1-6}$ dialkylamino, an N-acylamino, $-COOH$, an aryl, a heterocycle, pyrrolidine, pyrrole or pyridinyl, group;
$R^2$ is $C_{1-6}$ alkyl or unsubstituted or substituted aryl;
$R^3$ is H or unsubstituted or substituted $C_{1-6}$ alkyl;
$R^4$ is $C(=O)-R^5$, $C(=O)-O-R^5$, or $S(=O)_n-R^5$, wherein $R^5$ is $C_{1-6}$ alkyl, unsubstituted or substituted $C_{3-7}$ cycloalkyl, unsubstituted or substituted aryl, unsubstituted or substituted heteroaryl, and n is 0, 1, or 2; or $R^4$ is H or unsubstituted or substituted $C_{1-6}$ alkyl; or $R^3$ and $R^4$ along with the nitrogen atom form a nitro ($NO_2$) group; or $R^3$ and $R^4$ join to form an unsubstituted or substituted 5- or 6-membered ring with the proviso that it does not contain a $-N-(=J)-N-$ moiety where J is O or S;
wherein the substituted groups is substituted with 1, 2, or 3 substituents, each substituent is independently $C_{1-6}$ alkyl, halo, $-OH$, $-COOH$, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl; a pharmaceutically acceptable salt, a stereoisomeric form thereof, or a combination thereof.

In another embodiment, a compound of the structure of Formula (Ia)

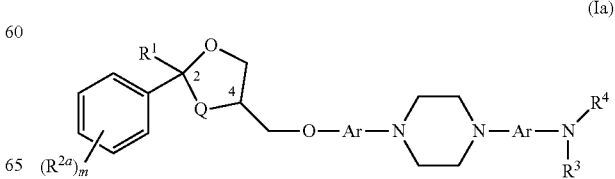

wherein

Q is O or CH$_2$;

each Ar is independently unsubstituted or substituted aryl;

R$^1$ is C$_{1-6}$ alkyl optionally substituted with an amino (—NH$_2$), a C$_{1-6}$ alkylamino, a C$_{1-6}$ dialkylamino, an N-acylamino, —COOH, an aryl, a heterocycle, pyrrolidine, pyrrole or pyridinyl, group;

each R$^{2a}$ independently is C$_{1-6}$ alkyl, halo, —OH, —COOH, cyano, nitro, amine, C$_{1-6}$ monoalkylamine, C$_{1-6}$ dialkylamine, C$_{1-6}$ haloalkyl, C$_{1-6}$ haloalkoxy, C$_{2-6}$ alkanoyl, or C$_{1-6}$ alkoxcarbonyl;

m is 0, 1, 2, or 3;

R$^3$ is H or unsubstituted or substituted C$_{1-6}$ alkyl;

R$^4$ is C(=O)—R$^5$, C(=O)—O—R$^5$, or S(=O)$_n$—R$^5$, wherein R$^5$ is C$_{1-6}$ alkyl, unsubstituted or substituted C$_{3-7}$ cycloalkyl, unsubstituted or substituted aryl, unsubstituted or substituted heteroaryl, and n is 0, 1, or 2; or R$^4$ is H or unsubstituted or substituted C$_{1-6}$ alkyl; or R$^3$ and R$^4$ along with the nitrogen atom form a nitro (NO$_2$) group; or R$^3$ and R$^4$ join to form an unsubstituted or substituted 5- or 6-membered ring with the proviso that it does not contain a —N—(=J)-N— moiety where J is O or S;

wherein the substituted groups is substituted with 1, 2, or 3 substituents, each substituent is independently C$_{1-6}$ alkyl, halo, —OH, —COOH, cyano, nitro, amine, C$_{1-6}$ monoalkylamine, C$_{1-6}$ dialkylamine, C$_{1-6}$ haloalkyl, C$_{1-6}$ haloalkoxy, C$_{2-6}$ alkanoyl, or C$_{1-6}$ alkoxcarbonyl; a pharmaceutically acceptable salt, a stereoisomeric form thereof, or a combination thereof.

DETAILED DESCRIPTION

For the treatment of different cancers and other cell proliferation disorders, there remains a need for the design of targeted therapies that, unlike standard chemotherapies, block tumor growth at precise molecular targets without causing cytotoxic effects to healthy tissue. Using the azole antifungal scaffold, disclosed are specific structural modifications to develop improved analogues with enhanced activity against Hh-dependent cell proliferation disorders, such as Hh-dependent cancers.

Disclosed herein are itraconazole (ITZ) and posaconazole (PSZ) analogues with novel structures that were designed based on systematic exploration of the ITZ and PSZ scaffolds to identify structural modifications that enhance inhibition of Hh signaling and maintain this activity against SMO mutants that confer resistance against vismodegib or other Hh inhibitors. The ITZ and PSZ analogues are angiogenesis inhibitors and are thus particularly useful as antiproliferative agents, for example, to treat cancers and other cell proliferation disorders that are dependent upon the Hh signaling pathway. In another aspect, the ITZ and PSZ analogs are useful to treat cell proliferation disorders, such as cancers, that are resistant to Vismodegib. In another embodiment, PSZ is disclosed as useful to treat a cell proliferation disorder, including for example, Hh signaling pathway-dependent cell proliferation disorders, such as Hh signaling pathway-dependent cancers.

Specifically, described herein are ITZ and PSZ analogues, wherein the ITZ and PSZ analogues are lacking the triazole moiety, or wherein the triazole moiety has been modified. In certain aspects, the ITZ and PSZ analogues are effective inhibitors of the Hh pathway, do not inhibit CYP3A4, and/or have anti-angiogenic activity.

The ITZ and PSZ analogues are compounds having the structure of Formula (I) or Formula (Ia):

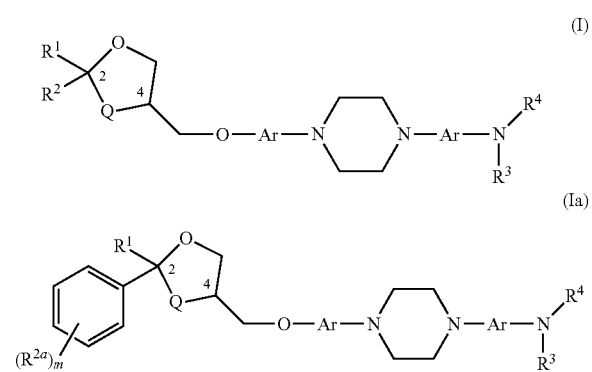

wherein

Q is O or CH$_2$;

each Ar is independently unsubstituted or substituted aryl;

R$^1$ is C$_{1-6}$ alkyl optionally substituted with an amino (—NH$_2$), a C$_{1-6}$ alkylamino, a C$_{1-6}$ dialkylamino, an N-acylamino, —COOH, an aryl, a heterocycle, pyrrolidine, pyrrole or pyridinyl, group;

R$^2$ is C$_{1-6}$ alkyl or unsubstituted or substituted aryl;

R$^3$ is H or unsubstituted or substituted C$_{1-6}$ alkyl;

R$^4$ is C(=O)—R$^5$, C(=O)—O—R$^5$, or S(=O)$_n$—R$^5$, wherein R$^5$ is C$_{1-6}$ alkyl, unsubstituted or substituted C$_{3-7}$ cycloalkyl, unsubstituted or substituted aryl, unsubstituted or substituted heteroaryl, and n is 0, 1, or 2; or R$^4$ is H or unsubstituted or substituted C$_{1-6}$ alkyl; or R$^3$ and R$^4$ along with the nitrogen atom form a nitro (NO$_2$) group; or R$^3$ and R$^4$ join to form an unsubstituted or substituted 5- or 6-membered ring with the proviso that it does not contain a —N—(=J)-N— moiety where J is O or S;

each R$^{2a}$ independently C$_{1-6}$ alkyl, halo, —OH, —COOH, cyano, nitro, amine, C$_{1-6}$ monoalkylamine, C$_{1-6}$ dialkylamine, C$_{1-6}$ haloalkyl, C$_{1-6}$ haloalkoxy, C$_{2-6}$ alkanoyl, or C$_{1-6}$ alkoxcarbonyl; and m is 0, 1, 2, or 3;

wherein each substituted group is substituted with 1, 2, or 3 substituents independently selected from C$_{1-6}$ alkyl, halo, —OH, —COOH, cyano, nitro, amine, C$_{1-6}$ monoalkylamine, C$_{1-6}$ dialkylamine, C$_{1-6}$ haloalkyl, C$_{1-6}$ haloalkoxy, C$_{2-6}$ alkanoyl, or C$_{1-6}$ alkoxcarbonyl;

a pharmaceutically acceptable salt, a stereoisomeric form thereof, or a combination thereof.

In an embodiment, for Formula (I) and (Ia), Q is O; and each Ar is phenyl, pyridine, pyrazine, or pyridazine.

In another embodiment, for Formula (I) and (Ia), Ar is phenyl.

In an embodiment, for Formula (I) and (Ia), R$^1$ is methyl or R$^1$ is methyl substituted with one of 1-pyrrole, 3-pyridine, 4-pyridine, phenyl, m-aminophenyl, p-aminophenyl, acetylamine, 1-pyrrolidine, amino, or dimethylamino; and R$^2$ is unsubstituted or substituted phenyl.

In an embodiment, for Formula (I) and (Ia), R$^1$ is methyl and R$^2$ is 2,4-dichlorophenyl or 2,4-difluorophenyl.

In an embodiment, for Formula (I) and (Ia), R4 is C(=O)—R5 or S(=O)n-R5. In an embodiment, for Formula (I) and (Ia), R$^5$ is unsubstituted or substituted C$_{3-7}$ cycloalkyl, unsubstituted or substituted aryl, unsubstituted or substituted heteroaryl.

Within Formula (I) and (Ia), the compounds can be prepared in racemic form, or any optically enriched form. Exemplary stereoisomers of Formula (I) include Formulae (I-1), (I-2), (I-3), or (I-4), and it is to be understood that the corresponding stereoisomers of Formula (Ia) are also included:

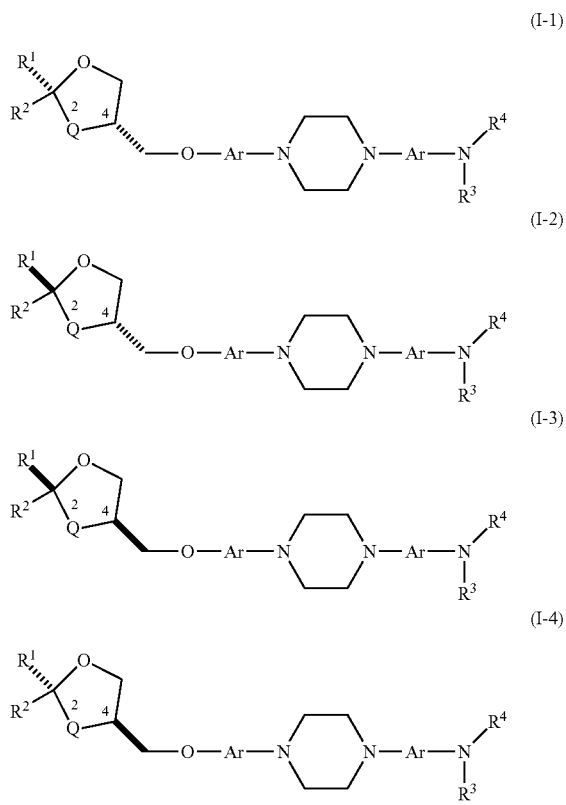

Also disclosed herein are liposome formulation comprising a compound having the structure of Formula (I) or (Ia) previously described, or a compound having the structure of Formula (II):

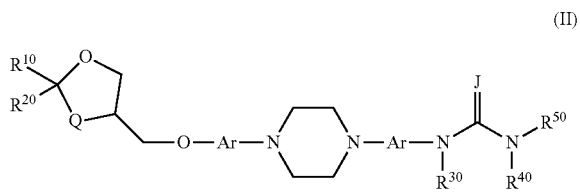

wherein

Q is O or $CH_2$, specifically O;

each Ar is independently unsubstituted or substituted aryl, specifically phenyl, pyridine, pyrazine, or pyridazine, and more specifically phenyl;

J is O or S, specifically O;

$R^{10}$ is $C_{1-6}$ alkyl optionally substituted with an amino, a $C_{1-6}$ alkylamino, a $C_{1-6}$ dialkylamino, an N-acylamino, —COOH, an aryl, a heterocycle, pyrrolidine, pyrrole, or pyridinyl group, specifically $R^{10}$ is methyl, optionally substituted with 1-pyrrole, 3-pyridine, 4-pyridine, phenyl, m-aminophenyl, p-aminophenyl, acetylamine, 1-pyrrolidine, amino, or dimethylamino, and more specifically $R^{10}$ is methyl;

$R^{20}$ is $C_{1-6}$ alkyl or unsubstituted or substituted aryl, specifically unsubstituted or substituted phenyl, and more specifically $R^{20}$ is 2,4-dichlorophenyl or 2,4-difluorophenyl;

$R^{30}$ is H or unsubstituted or substituted $C_{1-6}$ alkyl;

$R^{40}$ is H or unsubstituted or substituted $C_{1-6}$ alkyl; or $R^{30}$ and $R^{40}$ join to form an unsubstituted or substituted 5- or 6-membered ring with the —N—(=J)-N— moiety where $R^{30}$ and $R^{40}$ form a unsubstituted or substituted $C_{2-3}$ carbohydryl group or a unsubstituted or substituted $C_{1-2}$ carbohydryl group linked via a nitrogen to a nitrogen of the —N—(=J)-N— moiety;

$R^{50}$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$ alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_{1-6}$ haloalkoxy;

a pharmaceutically acceptable salt, a stereoisomeric form thereof, or a combination thereof.

Exemplary compounds according to Formula (II) include those described in U.S. Pat. No. 9,650,365 incorporated herein by reference in its entirety.

Specifically, in certain embodiments, the compounds of Formula (II) excludes itraconazole (CAS registry no. 84625-61-6) and posaconazole (CAS registry no. 171228-49-2).

In an embodiment of Formula (II), $R^{30}$ and $R^{40}$ join to form an unsubstituted or substituted 5- or 6-membered ring with the —N—(=J)-N— moiety where $R^{30}$ and $R^{40}$ form a unsubstituted or substituted $C_{2-3}$ carbohydryl group such as CH=CH, $CH_2$—$CH_2$, $CH_2$—$CH_2$—$CH_2$, or a unsubstituted or substituted $C_{1-2}$ carbohydryl group linked via a nitrogen to a nitrogen of the —N—(=J)-N— moiety, e.g. CH=N.

In an embodiment of Formula (II), $R^{50}$ is propyl; 2'-sec-butyl, the R isomer, the S isomer, a racemate or any enantiomerically enriched form; 2-hydroxypentan-3-yl, the 2R,3R-isomer, the 2S,3S, isomer, the 2R,3S, isomer, the 2S,3R isomer, or any diastereomerically enriched form; 2-hydroxyprop-2-yl; or 2-hydroxyprop-1-yl, the R isomer, the S isomer, a racemate, or any enantiomerically enriched form.

Within Formula (II), the compounds can be prepared in racemic form, or any optically enriched form. Exemplary stereoisomers of Formula (II) include Formulae (II-1), (II-2), (II-3), or (II-4):

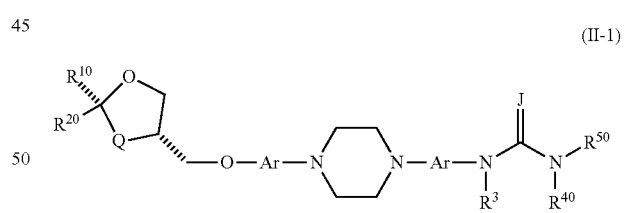

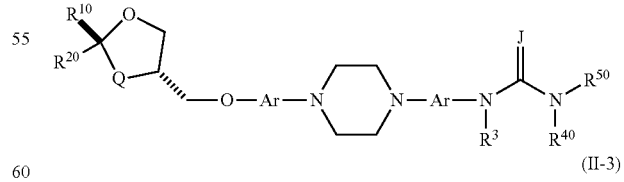

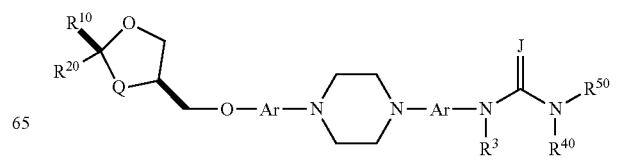

-continued

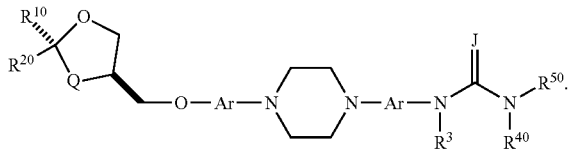

(II-4)

In another embodiment, the compounds have the structure of Formula (IIa)

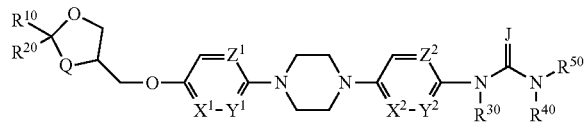

(IIa)

wherein

Q, J, $R^{10}$, $R^{20}$, $R^{30}$, $R^{40}$, and $R^{50}$ are as previously defined, and wherein each one of $X^1$, $X^2$, $Y^1$, $Y^2$, $Z^1$, and $Z^2$ independently is CH, $CCH_3$, or N.

Specifically, in certain embodiments, Formula (IIa) excludes itraconazole (CAS registry no. 84625-61-6) and posaconazole (CAS registry no. 171228-49-2). In several embodiments, a compound according to Formula (IIa) is included, wherein $X^1$ is N and $Y^1$, $Z^1$, $X^2$, $Y^2$, and $Z^2$ are CH;
$Y^1$ is N and $X^1$, $Z^1$, $X^2$, $Y^2$, and $Z^2$ are CH;
$X^1$ and $Y^1$ are N and $Z^1$, $X^2$, $Y^2$, and $Z^2$ are CH;
$X^1$ and $Z^1$ are N and $Y^1$, $X^2$, $Y^2$, and $Z^2$ are CH;
$X^2$ is N and $X^1$, $Y^1$, $Z^1$, $Y^2$, and $Z^2$ are CH;
$Y^2$ is N and $X^1$, $Y^1$, $Z^1$, $X^2$, and $Z^2$ are CH;
$X^2$ and $Y^2$ are N and $X^1$, $Y^1$, $Z^1$, and $Z^2$ are CH; or
$X^2$ and $Z^2$ are N and $X^1$, $Y^1$, $Z^1$, and $Y^2$ are CH.

It will be understood that the corresponding chiral Formulae of (IIa) similar to (II-1)-(II4) are included.

In certain situations, the compounds of Formulae I, Ia, and II may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with double bonds may occur in Z- and E-forms, with all isomeric forms of the compounds being included in the present disclosure. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The term "substituted", as used herein, means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a subject.

Chemical compounds are described using standard nomenclature. For example, any position not substituted by any indicated group is understood to have its valency filled by a bond as indicated, or a hydrogen atom. Unless defined otherwise, all technical and scientific terms used herein have the same meaning as is commonly understood by one of skill in the art to which this invention belongs. Structures and formulas include all subformulae thereof. For example formulas and compound structures include pharmaceutically acceptable salts, prodrugs and other derivatives, hydrates, polymorphs thereof. All forms (for example solvates, optical isomers, enantiomeric forms, polymorphs, free compound and salts) of an active agent may be employed either alone or in combination.

A dash ("-") that is not between two letters or symbols is used to indicate a point of attachment for a substituent. For example, —COOH is attached through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, phenyl$C_0$-$C_4$ alkyl, the indicated group, in this case phenyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, sec-pentyl, and n-hexyl. Specific alkyl groups include lower alkyl groups, those alkyl groups having 1, 2, 3, 4, 5, or 6 carbon atoms.

"Alkenyl" as used herein, indicates hydrocarbon chains of either a straight or branched configuration comprising one or more unsaturated carbon-carbon bonds, which may occur in any stable point along the chain, such as ethenyl and propenyl.

"Alkynyl" as used herein, indicates hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)—$.

The term "alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C=O)—$.

As used herein the term "alkanoyloxy" indicates an alkanoyl group as defined above, having the indicated number of carbon atoms, attached through an oxygen (—O—) bridge. Examples of alkanoyloxy groups include groups of the formula $CH_3(CH_2)(C=O)—O—$ and the like.

The term "alkylcarboxamide" indicates an alkyl group, as defined above, having the indicated number of carbon atoms, attached through a carboxamide linkage, i.e., a —$CONH_2$ linkage, where one or both of the amino hydrogens is replaced by an alkyl group. Alkylcarboxamide groups may be mono- or di-alkylcarboxamide groups, such an ethylcarboxamide or dimethylcarboxamide.

As used herein, the term "mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino. "Amino" on its own means —$NH_2$.

As used herein, the term "aryl" indicates aromatic groups containing only carbon in the aromatic ring or rings. Such aromatic groups may be further substituted with carbon or non-carbon atoms or groups. Typical aryl groups contain 1 to 3 separate, fused, or pendant rings and from 6 to about 18 ring atoms, specifically from about 8 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, anthracene, pentacene, fluorene, and bi-phenyl.

In the term "(aryl)alkyl", aryl and alkyl are as defined above, and the point of attachment is on the alkyl group. This term encompasses, but is not limited to, benzyl, phenylethyl, and piperonyl. Likewise, in the term (aryl)carbhydryl, aryl and carbhydryl are as defined above and the point of attachment is on the carbhydryl group, for example a phenylpropen-1-yl group.

"Carbhydryl" as used herein, includes both branched and straight-chain hydrocarbon groups, which are saturated or unsaturated, having the specified number of carbon atoms.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norbornane or adamantane.

"Haloalkyl" indicates both branched and straight-chain saturated aliphatic hydrocarbon groups having the specified number of carbon atoms, substituted with 1 or more halogen atoms, generally up to the maximum allowable number of halogen atoms ("perhalogenated", e.g. perfluorinated). Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge.

"Halo" or "halogen" as used herein refers to fluoro, chloro, bromo, or iodo.

As used herein, "heteroaryl" indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, these heteroatoms are not adjacent to one another. In one embodiment, the total number of S and O atoms in the heteroaryl group is not more than 2. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. In the term "heteroarylalkyl," heteroaryl and alkyl are as defined above, and the point of attachment is on the alkyl group. This term encompasses, but is not limited to, pyridylmethyl, thiophenylmethyl, and pyrrolyl(1-ethyl).

The term "heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

"Pharmaceutically acceptable salts" includes derivatives of the disclosed compounds wherein the parent compound is modified by making an acid or base salt thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional salts and the quaternary ammonium salts of the parent compound formed, for example, from inorganic or organic acids. For example, conventional acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Liposome formulations for targeted delivery of the disclosed compounds are disclosed. Liposomes offer an alternative mode of delivery of drugs to the brain. Often times, drugs that could be advantageous chemotherapeutic agents are not considered due to their physicochemical properties. A nanoparticle vehicle such as a liposome holds promise as a large percentage of small molecules and antibodies are not able to penetrate the blood brain barrier (BBB). In addition to modifying liposome properties via different lipids and different formation methods, liposomes can also be tagged with proteins that can aid in BBB penetration. For instance, liposomes can be formulated to contain a target ligand that can aid in penetrating the BBB and reaching the brain; these proteins include but are not limited to transferrin receptor (TfR), lipoprotein receptor-related protein (LRP), and nicotinic acetylcholine receptor (nAChRs). Transferrin receptors are widely expressed in endothelial cells of the BBB. While nanotechnology has proved successful with transferrin ligand, it may not be optimal to have this drug delivery system competing with natural ligand. A mouse monoclonal antibody (MAb) against rat TfR, OX26, has successfully been used to target liposomes across the BBB and coined "immunoliposome-based drug delivery." LRP has been reported to mediate transport of various lipid-conjugated nanoparticles across the BBB. The LRP ligand Aprotinin and more specifically, Angioprep, have effectively increased liposome treatment to the brain and have increased survival time of brain tumor-bearing mice. Nicotinic acetylcholine receptors (nAChRs) are ligand-ion channels that are expressed in the brain and brain capillary endothelial cells. Various peptides derived from viruses and toxins have been tagged to nanoparticles and enabled successful brain-targeted drug delivery. In addition to being advantageous for brain cancers, liposomes serve as a promising route of drug delivery for pediatric cancers.

There are four conventional ways to prepare liposomes: thin-film hydration method, reverse-phase evaporation technique, ethanol-injection method, and detergent dialysis. The thin-film hydration method involves dissolving lipids in organic solvent and then evaporating off the solvent resulting in a thin-film. To ensure that solvents are removed completely, the film is put on high vacuum overnight. Rehydration with aqueous solvent forms the liposomes: vigorous shaking yields multilamellar vesicles (MLVs) and gentle shaking yields giant unilamellar vesicles. Small unilamellar vesicles can be formed with various size reduction techniques. The reverse-phase evaporation technique involves dissolving lipid in organic solvent and then evaporating off the solvent to create a thin film. The film is redissolved in solvent and aqueous buffer is added to create a two-phase system. Slow evaporation of the organic solvent by rotary evaporation leads to liposome formation. The ethanol-injection method involves dissolving phospholipids in organic solvent (ethanol) and adding to aqueous solvent. Upon addition of the ethanol solution, liposomes are formed. The detergent dialysis method uses phospholipids dissolved in detergents to create micelles. This is then added to aqueous phase. Removal of detergent via dialysis or size-exclusion gel chromatography results in large unilamellar vesicles.

All four of these liposome formation methods typically result in larger-sized liposomes. However, small unilamellar vesicles can be formed with various size reduction techniques. As liposome size and size distribution are the most important liposome characteristics, it is often necessary to utilize additional size reduction techniques after the initial liposome formation. Size reduction can be achieved via sonication or extrusion. Probe sonication uses a titanium probe inserted into the liposome preparation. This generates smaller liposomes efficiently and can be used to prepare a desired liposome size. Water sonication can also be used if there is concern of metal contamination or high temperature affecting liposomes/lipid components. Alternatively, the size extrusion method uses a pressurized instrument to force liposomes through a polycarbonate membrane. The number of extrusion cycles depends on the size of the polycarbonate membrane pores.

The most well-known liposomal formulation is the ethanol-injection method. This method offers a plethora of advantages including using less toxic solvents, control over particle size/distribution, avoiding size reduction measures, and most importantly, that it is a naturally continuous process. Continuous processing offers benefits in comparison to batch processing and is thus important to consider in the pharmaceutical industry. First, continuous processing depends on the process run-time as opposed to the size of the reactor. Second, continuous processing has the potential to be automated and this reduces human involvement and error. Both of these factors are important to consider when scaling up a pharmaceutical process.

A suitable continuous processing method for the production of monodispersed liposomes is disclosed in Costa et al. Pharm. Res. 2016, 33 (2), 404-416, incorporated herein in its entirety. This production method depends heavily on fluid mechanics and physics. There have been a few reports of utilizing the ethanol-injection method for the production of unilamellar liposomes and these processes involve the use of two different fluid mixing techniques: laminar and turbulent. Laminar flow consists of smooth, steady fluid motion and relies heavily on fluid viscosity. Turbulent flow consists of chaotic fluid motion and relies less on the viscosity of the fluid. Reynolds number (Re) is an important factor in fluid flow and is described as the ratio of inertial to viscous forces. Reynolds number takes into account the fluid's resistance to change of motion and the amount of friction due to viscosity of fluid. Laminar conditions consist of water slowly mixing with the alcohol phase (low Reynolds number). Turbulent conditions consist of rapid mixing of the alcohol stream with the aqueous stream (high Reynolds number). Taking this into consideration, the liposome formation process was explored by relating these fluid dynamic properties with liposomal physical properties.

A suitable continuous processing method for the formation of liposomes utilizes a coaxial turbulent jet in co-flow. The turbulent jet co-flow apparatus begins with preparation containers that house lipid and aqueous solutions separately. A solution containing lipids and a water-miscible organic solvent is prepared by heating the solution to 50-60° C. and sonication. Once the components are dissolved, the lipid solution can be taken up by stainless steel tanks, which are pressurized and can be heated to help maintain solubility of lipids. These three tanks converge at a single point and static mixers are used to make sure the lipid solutions from three different tanks are mixed appropriately before introducing the aqueous phase. The aqueous phase enters the apparatus straight from its preparation container. The lipid solution is injected into the aqueous phase at different flow rates (5-40 mL/min or 60-400 mL/min, respectively). It is important to note that a hydrophilic drug would be incorporated into the aqueous solution and a hydrophobic drug would be incorporated into the lipid solution. This apparatus is controlled by a computer program, which was custom designed. The entire system is automated and exceptionally user friendly. The user only needs to define the final lipid concentration and the molar ratios of the lipid formulation. This apparatus is also attached to a Zetasizer® which records the size and polydispersion index (PDI) of a liposome population. This allows the lipid and aqueous phase flow rates to be adjusted in real-time to obtain the optimal sized liposomes. Exemplarly lipids, solvents, and aqueous phases for use in preparing liposomes include those in Table 1.

TABLE 1

| | Lipids | Solvent | Aqueous Phase |
|---|---|---|---|
| 1 | Soy phosphatidyl choline, cholesterol, stearylamine | CHCl$_3$ | Phosphate buffer (pH = 7.4) |
| 2 | Lecithin, cholesterol, | CHCl$_3$ | Phosphate buffer (pH = 5.8) |
| 3 | Lecithin, cholesterol, cyclodextrin | CHCl$_3$:MeOH | N/A |
| 4 | Soy lecithin, cholesterol, carboxymethyl chitosan | CHCl$_3$ | Phosphate buffer (pH = 7.4) |
| 5 | DPPC, cortisone acetate, polyethylene glycol (PEG200) | CHCl$_3$ | Phosphate buffer (pH = 7.4) |
| 6 | DPPC | CHCl$_3$ | 10 mM PBS (pH = 7.4) |
| 7 | Egg PC, MPEG-2000-DSPE, cholesterol | CHCl$_3$ | 6.67 mM KH$_2$PO$_4$ (pH = 6) |

Dipalmitoylphosphotidylcholine (DPPC), potassium dihydrogen phosphate (KH$_2$PO$_4$), 1,2-distearoyl-phosphitdylehtanolamine-methyl-polyethylene glycol-2000 (DSPE)

The ITZ and PSZ analogues disclosed herein as well as PSZ are expected to have activity as angiogenesis inhibitors and thus to be useful in the treatment of cancerous and non-cancerous cell proliferation disorders. In certain embodiments, the compounds disclosed herein and PSZ are inhibitors of the Hh signaling pathway and to be particularly useful in the treatment of cell proliferation disorders that are dependent upon the Hh signaling pathway. In cells regulated by the Hh pathway, signal transmission is controlled through a cascade that determines the balance between activator and repressor forms of the Gli family of transcription factors. In the absence of Hh ligand, Patched (Ptch) suppresses the activity of Smoothened (Smo), a seven-transmembrane protein that is normally observed in endosomes. This inhibition ultimately results in the generation of N-terminal truncated Gli proteins, Gli$^R$, that act as repressors of Hh-responsive genes. Binding of an Hh ligand to Ptch abolishes its inhibition of Smo, leading to the production of full-length Gli activator (Gli$^A$) proteins and resulting in expression of Hh target genes that control proper cell fate determination. Dysregulation of the pathway causes constitutive activation, resulting in uncontrolled proliferation and tumor growth; most notably, in basal cell carcinoma (BCC) and MB. Other cancers that may be treated with Hh signaling pathway inhibitors include, but are not limited to, chronic myeloid leukemia, lung cancer, prostate cancer, pancreatic cancer and bone cancer.

BCC is the most commonly diagnosed form of cancer in persons of European ancestry (affecting approximately 1 million Americans annually). It has been estimated that approximately 30% of Caucasians living in areas of high sun exposure will develop a BCC during their lifetime and the incidence of BCC in younger populations (especially young females) is rising. While BCC is rarely fatal, it can result in significant morbidity and the large number of affected individuals presents an increasing health burden.

MB is the most common malignant central nervous system tumor in children, accounting for approximately 20% of pediatric brain tumors and most commonly occurring in children under the age of 8 (40% before the age of 5). Current therapy for pediatric MB patients includes surgery followed by radiation and high-dose chemotherapy. While survival rates for pediatric MB patients have improved over the last ten years, long-term side effects of this course of treatment can include neurocognitive and endocrine deficits as well as growth impairment. In addition, these patients are at an increased risk of developing secondary tumors later in life. Uncontrolled activation of Hh signaling, including both mutation and amplification of key pathway components, has been implicated in approximately 25% of MBs. ITZ is currently administered to and tolerated by children for the treatment of various fungal infections and serves as a promising scaffold for pediatric cancer treatment.

Patients in need of treatment using the ITZ and PSZ analogues disclosed herein, compositions containing them, can be identified using standard techniques known to those in the medical or veterinary professions, as appropriate. In some embodiments, the proliferation disorder to be treated is one characterized by upregulation (elevation) of Hedgehog (Hh) level and/or Hedgehog pathway (HhP) signaling above the constitutive level (or normal level for the normal cell type in question). As indicated above, optionally, subjects in need of treatment (or further treatment) of a proliferation disorder such as prostate cancer, basal cell carcinoma, lung cancer, or other proliferation disorder, may be selected as an individual particularly suitable for treatment with an ITZ or PSZ analogue disclosed herein, based on Hh level or signaling, which may be assessed directly or indirectly by measuring a biomarker (an HhP biomarker) that represents the HhP signal itself or a modulator of the HhP signal (inducer or inhibitor).

Cancer is an example of a proliferation disorder that may be treated with the ITZ and PSZ analogues disclosed herein. The terms "cancer" and "malignancy" are used herein interchangeably to refer to or describe the physiological condition in humans and animals that is typically characterized by unregulated cell growth. The methods and compositions of the invention can be utilized for early, middle, or late stage disease, and acute or chronic disease. The cancer may be drug-resistant or drug-sensitive. Examples of cancer include but are not limited to, carcinoma, lymphoma, blastoma, sarcoma, and leukemia. More particular examples of such cancers include breast cancer (such as triple-negative breast cancer), prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer (e.g., hepatic carcinoma), bladder cancer, colorectal cancer, endometrial carcinoma, kidney cancer, medulloblastoma, glioblastoma, and thyroid cancer. In some embodiments, the cancer is a hematologic malignancy (for example, multiple myeloma, leukemia, acute myeloid leukemia, chronic myeloid leukemia (AML), and myeloid dysplastic syndrome). In some embodiments, the cancer is a non-hematologic malignancy.

Other non-limiting examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas. Examples of cancer types that may potentially be treated using the ITZ and PSZ analogues disclosed herein are also listed in Table 2.

TABLE 2

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult (Primary) |
| Acute Myeloid Leukemia, Adult | |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | |
| Gastrointestinal Carcinoid Tumor | Non-Small Cell Lung Cancer |
| Germ Cell Tumor, Extracranial, Childhood | Oral Cancer, Childhood |
| | Oral Cavity Cancer, Lip and |
| Germ Cell Tumor, Extragonadal | Oropharyngeal Cancer |
| Germ Cell Tumor, Ovarian | Osteosarcoma/Malignant Fibrous |

TABLE 2-continued

Examples of Cancer Types

| | |
|---|---|
| Gestational Trophoblastic Tumor | Histiocytoma of Bone |
| Glioma, Adult | Ovarian Cancer, Childhood |
| Glioma, Childhood Brain Stem | Ovarian Epithelial Cancer |
| Glioma, Childhood Cerebral Astrocytoma | Ovarian Germ Cell Tumor |
| | Ovarian Low Malignant Potential Tumor |
| Glioma, Childhood Visual Pathway and Hypothalamic | Pancreatic Cancer |
| | Pancreatic Cancer, Childhood |
| Skin Cancer (Melanoma) | Pancreatic Cancer, Islet Cell |
| Skin Carcinoma, Merkel Cell | Paranasal Sinus and Nasal Cavity Cancer |
| Small Cell Lung Cancer | Parathyroid Cancer |
| Small Intestine Cancer | Penile Cancer |
| Soft Tissue Sarcoma, Adult | Pheochromocytoma |
| Soft Tissue Sarcoma, Childhood | Pineoblastoma and Supratentorial Primitive Neuroectodermal Tumors, Childhood |
| Squamous Cell Carcinoma, see Skin Cancer (non-Melanoma) | |
| | Pituitary Tumor |
| Squamous Neck Cancer with Occult Primary, Metastatic | Plasma Cell Neoplasm/Multiple Myeloma |
| | Pleuropulmonary Blastoma |
| Stomach (Gastric) Cancer | Pregnancy and Breast Cancer |
| Stomach (Gastric) Cancer, Childhood | Pregnancy and Hodgkin's Lymphoma |
| Supratentorial Primitive Neuroectodermal Tumors, Childhood | Pregnancy and Non-Hodgkin's Lymphoma |
| | Primary Central Nervous System Lymphoma |
| T-Cell Lymphoma, Cutaneous, see Mycosis Fungoides and Sézary Syndrome | Prostate Cancer |
| | Rectal Cancer |
| | Renal Cell (Kidney) Cancer |
| Testicular Cancer | Renal Cell (Kidney) Cancer, Childhood |
| Thymoma, Childhood | Renal Pelvis and Ureter, Transitional Cell Cancer |
| Thymoma and Thymic Carcinoma | |
| Thyroid Cancer | Retinoblastoma |
| Thyroid Cancer, Childhood | Rhabdomyosarcoma, Childhood |
| Transitional Cell Cancer of the Renal Pelvis and Ureter | Salivary Gland Cancer |
| | Salivary Gland Cancer, Childhood |
| Trophoblastic Tumor, Gestational | Sarcoma, Ewing's Family of Tumors |
| Unknown Primary Site, Carcinoma of, Adult | Sarcoma, Kaposi's |
| | Sarcoma, Soft Tissue, Adult |
| Unknown Primary Site, Cancer of, Childhood | Sarcoma, Soft Tissue, Childhood |
| | Sarcoma, Uterine |
| Unusual Cancers of Childhood | Sézary Syndrome |
| Ureter and Renal Pelvis, Transitional Cell Cancer | Skin Cancer (non-Melanoma) |
| | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

In some embodiments, the proliferation disorder is prostate cancer. In some embodiments, the prostate cancer is a pre-cancer of the prostate. In some embodiments, the prostate cancer is metastatic. In some embodiments, the prostate cancer is non-metastatic. In some embodiments, the prostate cancer is castration-resistant. In some embodiments, the prostate cancer is non-castration resistant. In some embodiments, the prostate cancer is metastatic, castration-resistant prostate cancer. In some embodiments, the prostate cancer is non-metastatic, castration-resistant prostate cancer. In some embodiments, the subject being treated for prostate cancer has undergone androgen deprivation therapy, undergoes androgen deprivation therapy concurrently with the ITZ analogue or PSZ analogue treatment, or both. Examples of treatments/agents for androgen deprivation therapy that may be utilized include, but are not limited, to orchiectomy (surgical castration), luteinizing hormone-releasing hormone (LHRH) analogs (e.g., leuprolide, goserelin, triptorelin, or histrelin), luteinizing hormone-releasing hormone (LHRH) antagonists (e.g., degarelix and abiraterone), anti-androgens (flutamide, bicalutamide, nilutamide, and enzalutamide), and other androgen-suppressing drugs (e.g., ketoconazole).

In some embodiments, the proliferation disorder is skin cancer, such as melanoma, or a non-melanoma, such as basal cell carcinoma (BCC), which is a nonmelanocytic skin cancer (i.e., an epithelial tumor) and is the most common form of skin cancer. In some embodiments, the BCC is a type selected from among nodular BCC, cystic BCC, cicatricial BCC, infiltrative BCC, micronodular BCC, superficial BCC, pigmented BCC, Jacobi ulcer, fibroepithelioma of Pinkus, polyoid basal-cell carcinoma, pore-like BCC, or aberrant BCC. In some embodiments, the BCC is sporadic BCC. In some embodiments, the BCC is hereditary BCC. In some embodiments, the subject has a BCC tumor equal to or greater than 4 mm.

In some embodiments, the proliferation disorder is lung cancer (stage I, stage II, stage Ma, stage Mb, or stage IV). In some embodiments, the lung cancer is a non-small cell lung cancer (NSCLC), such as squamous cell carcinoma, non-squamous cell carcinoma, large cell carcinoma, and adenocarcinoma. In some embodiments, the lung cancer is small cell lung cancer (SCLC). In some embodiments, the lung cancer is non-squamous cell lung carcinoma. In some embodiments, the lung cancer is mesothelioma (e.g., malignant pleural mesothelioma). In some embodiments, the lung cancer is late-stage metastatic NSCLC.

Optionally, one or more tests are performed before and/or after treatment of the lung cancer, such as bone scan, chest x-ray, complete blood count (CDC), CT scan, liver function tests, magnetic resonance imaging (MRI), positron emission tomography (PET), sputum test, and thoracentesis. Optionally, a biopsy may be obtained before and/or after treatment of the lung cancer (e.g., bronchoscopy with biopsy, CT-scan directed needle biopsy, endoscopic esophageal ultrasound with biopsy, mediastinoscopy with biopsy, open lung biopsy, pleural biopsy, and video assisted thoracoscopy).

As used herein, the term "tumor" refers to all neoplastic cell growth and proliferation, whether malignant or benign, and all pre-cancerous and cancerous cells and tissues. For example, a particular cancer may be characterized by a solid mass tumor or non-solid tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography) or magnetic resonance imaging (MRI), or by needle aspirations. The use of these latter techniques is more common in early detection. Molecular and phenotypic analysis of cancer cells within a tissue can usually be used to confirm if the cancer is endogenous to the tissue or if the lesion is due to metastasis from another site.

As indicated above, an example of a proliferation disorder is cancer, e.g., undesirable or unwanted or aberrant proliferation and survival of cancer cells such as cells associated with prostate cancer, lymphoma, myeloma, sarcoma, leukemia, or other neoplastic disorders disclosed elsewhere herein and known to one of skill in the art. Proliferation disorders include pre-cancerous or pre-malignant conditions (e.g., morphologically identifiable lesions that precede invasive cancers), intraepithelial neoplasia (e.g., prostatic IEN and cervical IEN), atypical adenomatous hyperplasia, colorectal polyps, basal cell nevus syndrome, actinic keratosis, Barrett's esophagus, atrophic gastritis, and cervical dysplasia.

In some embodiments, the proliferation disorder is a non-cancerous proliferation disorder. In some embodiments, the non-cancerous proliferation disorder involves uncontrolled proliferation of endothelial cells and/or epithelial cells. Some examples of non-cancerous proliferation disorders include smooth muscle cell proliferation, systemic sclerosis, cirrhosis of the liver, nonalcoholic steatohepatitis (NASH), adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, fibrosis (e.g., pulmonary fibrosis, kidney fibrosis, liver fibrosis, and pancreatic fibrosis), endometriosis, fibromatosis, hamartomas, lymphangiomatosis, sarcoidosis, desmoid tumors (e.g., aggressive fibromatosis), familial adenomatous polyposis (FAP; e.g., classic FAP, attenuated FAP, Gardner syndrome, or Turcot syndrome), acute or chronic graft-versus-host disease, and over-proliferation of stem cells (e.g., mesenchymal stem cells). Non-cancerous proliferation disorders also include hyperproliferation of cells in the skin such as psoriasis and its varied clinical forms, Reiter's syndrome, *pityriasis rubra* pilaris, hyper-proliferative variants of disorders of keratinization (e.g., actinic keratosis, senile keratosis), scleroderma, seborrheic keratoses, intraepidermal nevi, common warts, benign epithelial tumors, nevoid basal cell carcinoma syndrome (Gorlin syndrome, who are then prone to develop basal cell carcinoma), and the like.

In certain embodiments, the compounds described herein are administered to a patient or subject. A "patient" or "subject", used equivalently herein, means mammals and non-mammals. "Mammals" means a member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

As used herein, the terms "about" and "approximately" shall generally mean an acceptable degree of error for the quantity measured given the nature or precision of the measurements. Exemplary degrees of error are within 20 percent (%), typically, within 10%, and more typically, within 5% of a given value or range of values.

As used herein, and unless otherwise specified, the terms "treat," "treating" and "treatment" contemplate an action that occurs while a subject has a proliferation disorder such as cancer (as therapy), or before the subject has the proliferation disorder (as prophylaxis), which reduces the severity of the proliferation disorder, retards or slows the progression of the proliferation disorder, or prevents the proliferation disorder. Thus, treatment with HhP inhibitors such as the ITZ and PSZ analogues disclosed herein may prevent or manage proliferation disorders such as cancer.

As used herein, unless otherwise specified, the terms "prevent," "preventing", and "prevention" contemplate an action that occurs before a subject begins to suffer from the regrowth of the proliferation disorder and/or which inhibits or reduces the severity of the proliferation disorder, or delays its onset.

As used herein, and unless otherwise specified, the terms "manage," "managing" and "management" encompass preventing the recurrence of the proliferation disorder in a subject who has already suffered from the proliferation disorder, and/or lengthening the time that a subject who has suffered from the proliferation disorder remains in remission. The terms encompass modulating the threshold, development and/or duration of the proliferation disorder, or changing the way that a patient responds to the proliferation disorder.

As used herein, the term "efficacy" in the context of therapy refers to the ability of the therapy with the ITZ analogues or PSZ analogues (as monotherapy or in combination therapy with another HhP inhibitor or other agent that is not an HhP inhibitor) to alleviate one or more symptoms of the proliferation disorder (e.g., cancer), diminish the extent of disease, stabilize (i.e., not worsening) the state of the disease, delay or slow disease progression, amelioration or palliation of the disease state, remission (whether partial or total), whether detectable or undetectable, tumor regression, inhibit tumor growth, inhibit tumor metastasis, reduce cancer cell number, inhibit cancer cell infiltration into peripheral organs, increase progression free survival, improve progression free survival, improve time to disease progression (TTP), improve response rate (RR), prolonged overall survival (OS), prolong time-to-next-treatment (TNTT), or prolong time from first progression to next treatment, or a combination of two or more of the foregoing.

As used herein, the terms "anticancer agent," "conventional anticancer agent," or "cancer therapeutic drug" refer to any therapeutic agents (e.g., chemotherapeutic compounds and/or molecular therapeutic compounds), immunotherapies (e.g., immune checkpoint inhibitors), radiation therapies, or surgical interventions, used in the treatment of cancer (e.g., in mammals). The ITZ analogues and PSZ analogues disclosed herein may be administered with a therapeutic agent, such as an anticancer agent.

As used herein, the terms "proliferation disorder", "cell proliferation disorder", "proliferative disorder", "cell proliferative disorder", "condition characterized by undesirable cell proliferation", and grammatical variations thereof refer to any pathological or non-pathological physiological condition characterized by aberrant or undesirable proliferation of at least one cell, including but not limited to conditions characterized by undesirable or unwanted or aberrant cell proliferation, conditions characterized by undesirable or unwanted or aberrant cell survival, and conditions characterized by deficient or aberrant apoptosis. The term "cell proliferation" and grammatical variations thereof, are understood to encompass both an increase in the number of cells as a result of cell division, as well as an increase in the total mass of cells as a result of cell growth, e.g., by growth of daughter cells after mitosis. Proliferation disorders may be can cancerous or non-cancerous.

The terms "cancer" and "malignancy" are used herein interchangeably to refer to or describe the physiological condition in humans and animals that is typically characterized by unregulated cell growth. The term encompasses dysplasia, carcinoma in situ (CIS), and carcinoma. The cancer may be metastatic or non-metastatic.

The phrase "effective amount," as used herein, means an amount of an agent which is sufficient enough to significantly and positively modify symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

The specific therapeutically effective amount for a particular patient of a compound, composition or formulation disclosed herein will depend on a variety of factors including the activity of the specific compound employed, the age, body weight, general health, sex, diet, time of administration, route of administration, rate of excretion, drug combination, and the severity of the particular disease undergoing therapy. Concentrations of the compounds described herein found in therapeutic compositions will vary depending upon a number of factors, including the dosage of the drug to be administered, the chemical characteristics (e.g., hydrophobicity) of the compounds employed, and the route of administration. In general, a suitable effective dose is in the range of about 0.1 to about 500 mg/kg body weight per day, preferably in the range of about 5 to about 350 mg/kg per day. The total daily dose may be given as a single dose, multiple doses, e.g., two to six times per day, or by intravenous infusion for a selected duration. Dosages above or below the range cited above may be administered to the individual patient if desired and necessary.

As used herein, "pharmaceutical composition" means therapeutically effective amounts of the compound together with a pharmaceutically acceptable excipient, such as diluents, preservatives, solubilizers, emulsifiers, and adjuvants. As used herein "pharmaceutically acceptable excipients" are well known to those skilled in the art.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents. In some embodiments, the ITZ and PSZ analogues disclosed herein are administered systemically (e.g., intravenously or orally). In other embodiments, the ITZ and PSZ analogues disclosed herein are administered locally at the site of a tumor (e.g., by direct injection). Preparations for oral administration can be suitably formulated to give controlled release of active compounds.

The ITZ and PSZ analogues disclosed herein may be formulated as an oral SUBA™ (Mayne Pharma International Pty Ltd.) formulation using SUBA™ bioavailability technology, which is capable of enhancing the bioavailability of poorly soluble drugs. The technology uses a solid dispersion of the active pharmaceutical ingredient (e.g., drug) in a pH-dependent polymeric matrix to enhance the absorption, and thus bioavailability, of drugs in the gastrointestinal tract, compared to conventional formulations. This dispersion improves the dissolution of less soluble drugs relative to their normal crystalline form. Potential benefits include increased bioavailability, reduced intra/inter-patient variability, and reduced side effects.

ITZ is a weakly basic Biopharmaceutics Classification System (BCS) class II (low solubility/high permeability) drug that has a pH-dependent dissolution and thus typically requires an acidic gastric environment for sufficient drug dissolution and adequate absorption. The co-administration of ITZ in a conventional formulation with agents that inhibit gastric acidity, such as ant-acids and proton pump inhibitors, reduce ITZ absorption. Furthermore, the pharmacokinetics of ITZ is complex and highly variable, especially after oral administration. SUBA™ technology has been successfully applied to improve the bioavailability of ITZ (SUBA-itraconazole), and this formulation (brand name Lozanoc®, Mayne Pharma International Pty Ltd.) has received regulatory approval in Australia and some European markets. The SUBA-itraconazole formulation enhances the drug's dissolution and intestinal absorption.

Accordingly, ITZ analogues and PSZ analogues disclosed herein can be used in place of ITZ in a SUBA formulation to provide potential enhancements to patients and care providers in the form of reduced intra- and inter-patient variability, enabling a more predictable clinical response and reduction in the active drug quantity to deliver the required therapeutic blood levels.

In some embodiments, the SUBA formulation is a composition comprising a solid dispersion of at least one ITZ analogue or PSZ analogue disclosed herein, and at least one polymer. The polymers useful for forming the solid dispersion of the composition are those having acidic functional groups. In a preferred form, such polymers will be polycarboxylic acids. Such polycarboxylic acids may be any polycarboxylic acid which, when in a solid dispersion with a relatively insoluble drug, results in the formation of the abovementioned suspension, ideally in the preferred pH ranges, and preferably to provide acceptable absorption in the intestines.

Such polymers may be one or more of the group comprising hydroxypropyl methylcellulose phthalate, polyvinyl acetate phthalate (PVAP), hydroxypropylmethylcellulose acetate succinate (HPMCAS), alginate, carbomer, carboxymethyl cellulose, methacrylic acid copolymer, shellac, cellulose acetate phthalate (CAP), starch glycolate, polacrylin, methyl cellulose acetate phthalate, hydroxypropylcellulose acetate phthalate, cellulose acetate terephthalate, cellulose acetate isophthalate and cellulose acetate trimellitate, and includes the various grades of each polymer such as HPMCAS-LF, HPMCAS-MF and HPMCAS-HG.

In some embodiments, the polymer is a polycarboxylic acid such as a hydroxypropyl methylcellulose phthalate (i.e., hypromellose phthalate or HPMCP) such as that available from Shin-Etsu Chemical Industry Co Ltd. as HP-50, HP-55 or HP-555. However, it is contemplated that alternatives such as the use of an aqueous based enteric polymer, such as the dispersion Eudragit L30D, or enteric polymers dissolved in water with the addition of ammonia or alkaline agents, may be useful.

In relation to amounts of drug and the polymer in the solid dispersion, the ratio of drug to polymer may be in the range of from 3:1 to 1:20. In some embodiments, the ratio of drug to polymer is in the range of 3:1 to 1:5. In some embodiments, the ratio of drug to polymer is in the range of 1:1 to 1:3, or about 1:1.5 (or 2:3). In some embodiments, the composition comprises about 40% ITZ analogue or PSZ analogue and about 60% polymer (e.g., about 60% HP-50).

The solid dispersion of the composition may be formed by spray drying techniques, although it will be understood that suitable solid dispersions may be formed by a skilled addressee utilising other conventional techniques, such as co-grinding, melt extrusion, freeze drying, rotary evaporation or any solvent removal process. With the spray drying technique, the solid dispersion is typically formed by dispersing or dissolving the drug and the polymer in a suitable solvent, and subsequently spray drying to form the solid dispersion in the form of a powder. Suitable solvents or dispersion media include methylene chloride, chloroform, ethanol, methanol, propan-2-ol, ethylacetate, acetone, water or mixtures thereof.

Other excipients may then be blended into the powder (with or without milling or grinding) to form a composition suitable for use in oral dosage forms such as tablets and capsules.

The present invention therefore also provides a process for preparing a SUBA formulation comprising at least one ITZ analogue or PSZ analogue and at least one polymer, the process including dispersing in a solvent the ITZ analogue(s) and or PSZ analogues(s) and a polymer having acidic functional groups, and spray drying the dispersion to form a solid dispersion.

SUBA formulations, and methods for their production, are described in U.S. Pat. No. 6,881,745 (Hayes et al., "Pharmaceutical Compositions for Poorly Soluble Drugs"); U.S. Pat. No. 8,771,739 (Hayes et al., "Pharmaceutical Compositions for Poorly Soluble Drugs"); and U.S. Pat. No. 8,921,374 (Mudge et al., "Itraconazole Compositions and Dosage Forms, and Methods of Using the Same"), which are each incorporated by reference herein in their entireties.

In some embodiments, when administered, the composition in vivo provides a mean $C_{MAX}$ of at least 100 ng/ml (e.g., 150 to 250 ng/ml). In some embodiments, upon administration, the composition forms a suspension at a pH in the range of 4.0 to 8.0, and more preferably in the range of 5.5 to 7.5, and provides acceptable absorption in the intestines.

Drug release occurs in the intestines; therefore, fed or fasted state does not affect the absorption, nor are there restrictions for achlorhydric patients or patients on proton-pump inhibitor drugs for high acid control. Thus, the SUBA formulation can be taken with or without food, and can optionally be taken with drugs that lower gastric acidity without reduction in the availability of the ITZ analogue or PSZ analogue, which increases patient convenience. In some embodiments, the composition is orally administered in an effective amount to achieve a plasma trough level of at least about 1,000 ng/mL of the ITZ analogue or PSZ analogue in the patient. In some embodiments, the composition is orally administered at a dose in the range of 100 mg to 600 mg ITZ analogue or PSZ analogue per day.

Optionally, the ITZ analogue or PSZ analogue used in the SUBA formulation may be formulated as a liposome. Accordingly, optionally, the liposome embodiments of ITZ analogues and PSZ analogues disclosed herein may be formulated as a SUBA formulation. For topical application to the skin, the drug may be made up into a cream, lotion or ointment. Cream or ointment formulations which may be used for the drug are conventional formulations well known in the art. Topical administration includes transdermal formulations such as patches. For topical application to the eye, the compounds may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

In treating a proliferation disorder, one or more ITZ analogues or PSZ analogues disclosed herein (and compositions containing them) may be administered by any route effective for delivery to the desired tissues, e.g., administered orally, parenterally (e.g., intravenously), intramuscularly, sublingually, buccally, rectally, intranasally, intrabronchially, intrapulmonarily, intraperitoneally, topically, transdermally and subcutaneously, for example. The ITZ analogues or PSZ analogues disclosed herein can be formulated for the most effective route of administration. For example, the compounds may be administered orally or locally (e.g., by direct injection) to a desired site, such as a precancerous lesion or tumor (e.g., prostate cancer lesion or prostate tumor or other cancer tumor). The amount administered in a single dose may be dependent on the subject being treated, the subject's weight, the manner of administration and the judgment of the prescribing physician. Generally, however, administration and dosage and the duration of time for which a composition is administered will approximate those which are necessary to achieve a desired result.

The active ingredient may also be administered parenterally in a sterile medium, either subcutaneously, or intravenously, or intramuscularly, or intrasternally, or by infusion techniques, in the form of sterile injectable aqueous or oleaginous suspensions. Such formulations can be presented in unit dosage form, with or without an added preservative. Depending on the vehicle and concentration used, the drug can either be suspended or dissolved in the vehicle. Advantageously, adjuvants such as a local anaesthetic, preservative, suspending agents, stabilizing agents, dispersing agents, and buffering agents or a combination thereof can be dissolved in the vehicle.

The ITZ analogues and PSZ analogues can be disclosed herein can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form. In other embodiments compounds are formulated as long acting formulations that can be administered by implantation (e.g., subcutaneously or intramuscularly) or by intramuscular injection. Such formulations may include suitable polymeric or hydrophobic materials, or ion exchange resins. Other embodiments may include liposomes and/or emulsions.

The ITZ analogues and PSZ analogues disclosed herein can be administered to a subject by itself, or co-administered with one or more other agents such as an HhP inhibitor, or a different agent or agents. In some embodiments, the additional agent is one or more anti-cancer agents. Anti-cancer agents include but are not limited to the anti-cancer agents listed in Table 3.

Co-administration can be carried out simultaneously (in the same or separate formulations) or consecutively with the additional agent administered before and/or after one or more HhP inhibitors. Furthermore, ITZ analogues and PSZ analogues disclosed herein can be administered to a subject as adjuvant therapy. For example, one or more HhP inhibitors can be administered to a patient in conjunction with one or more chemotherapeutic agents.

Thus, the ITZ analogues and PSZ analogues, whether administered separately, or as a pharmaceutical composition, can include various other components as additives. Examples of acceptable components or adjuncts which can be employed in relevant circumstances include antioxidants, free radical scavenging agents, peptides, growth factors, antibiotics, bacteriostatic agents, immunosuppressives, anti-coagulants, buffering agents, anti-inflammatory agents, anti-angiogenics, anti-pyretics, time-release binders, anesthetics, steroids, and corticosteroids. Such components can provide additional therapeutic benefit, act to affect the therapeutic action of the ITZ or PSZ analogues, or act towards preventing any potential side effects that may be posed as a result of administration of these agents. The ITZ analogue or PSZ analogue can be conjugated to a therapeutic agent, as well.

In some embodiments, one or more additional HhP inhibitors are administered with the one or more ITZ analogues and/or one or more PSZ analogues. They may be administered to the subject simultaneously in the same or different formulations, or sequentially. The additional HhP inhibitors may act on the same member of the Hedgehog signaling pathway as the ITZ analogue or PSZ analogue, whether in similar or distinct manners, or on different members of the pathway. For example, it may be desirable to administer HhP inhibitors that inhibit the HhP pathway at different points in the pathway or by different mechanisms. For example, while both itraconazole and vismodegib target Smo, they differ in the way they bind and act on the receptor, inhibiting the HhP by different mechanisms of action. Vismodegib acts as a cylcopamine-competitive antagonist of the Smo receptor, causing the transcription factors Gli1 and Gli2 to remain inactive, which inhibits the expression of tumor mediating genes within the HhP. In contrast, itraconazole inhibits activation of the HhP by targeting Smo at a site distinct from that of cyclopamine mimics currently in development. The Smo protein can generally be activated by its translocation to the primary cilium and/or by changing its configuration. Vismodegib works on Smo effectively by ensuring that the protein does not change its configuration, whereas itraconazole works by preventing its translocation. These distinctions are supported by the ability of these two drugs to synergize. Accordingly, in some embodiments, one or more additional HhP inhibitors are administered and the additional HhP inhibitor differs from the ITZ or PSZ analogue in its mechanism of action by which it inhibits the HhP.

Additional agents that can be co-administered to subjects, in the same or as a separate formulation, include those that modify a given biological response, such as immunomodulators. The additional agents may be, for example, small molecules, polypeptides (proteins, peptides, or antibodies or antibody fragments), or nucleic acids (encoding polypeptides or inhibitory nucleic acids such as antisense oligonucleotides or interfering RNA). For example, proteins such as tumor necrosis factor (TNF), interferon (such as alpha-interferon and beta-interferon), nerve growth factor (NGF), platelet derived growth factor (PDGF), and tissue plasminogen activator can be administered. Biological response modifiers, such as lymphokines, interleukins (such as interleukin-1 (IL-1), interleukin-2 (IL-2), and interleukin-6 (IL-6)), granulocyte macrophage colony stimulating factor (GM-CSF), granulocyte colony stimulating factor (G-CSF), or other growth factors can be administered. In one embodiment, the methods and compositions of the invention incorporate one or more anti-cancer agents, such as cytotoxic agents, chemotherapeutic agents, anti-signaling agents, and anti-angiogenic agents.

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). In one embodiment, the anti-cancer agent administered before, during, or after administration of the ITZ analogue or PSZ analogue is a different HhP inhibitor. Anti-cancer agents include but are not limited to the anti-cancer agents listed in Table 3.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, Tenn.), and anti-androgens such as flutamide, nilutamide, bicalutamide, leuprolide, and goserelin, etc. Examples of chemotherapeutic agents that may be used in conjunction with the ITZ analogues and PSZ analogues are listed in Table 3. In some embodiments, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

TABLE 3

Examples of Anti-Cancer Agents

| | |
|---|---|
| 13-cis-Retinoic Acid | Mylocel |
| 2-Amino-6-Mercaptopurine | Letrozole |
| 2-CdA | Neosar |
| 2-Chlorodeoxyadenosine | Neulasta |
| 5-fluorouracil | Neumega |
| 5-FU | Neupogen |
| 6-TG | Nilandron |
| 6-Thioguanine | Nilutamide |
| 6-Mercaptopurine | Nitrogen Mustard |
| 6-MP | Novaldex |
| Accutane | Novantrone |
| Actinomycin-D | Octreotide |
| Adriamycin | Octreotide acetate |
| Adrucil | Oncospar |
| Agrylin | Oncovin |
| Ala-Cort | Ontak |
| Aldesleukin | Onxal |
| Alemtuzumab | Oprevelkin |
| Alitretinoin | Orapred |
| Alkaban-AQ | Orasone |
| Alkeran | Oxaliplatin |
| All-transretinoic acid | Paclitaxel |
| Alpha interferon | Pamidronate |
| Altretamine | Panretin |
| Amethopterin | Paraplatin |
| Amifostine | Pediapred |
| Aminoglutethimide | PEG Interferon |
| Anagrelide | Pegaspargase |
| | Pegfilgrastim |

TABLE 3-continued

Examples of Anti-Cancer Agents

| | |
|---|---|
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |

TABLE 3-continued

Examples of Anti-Cancer Agents

| | |
|---|---|
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin - 2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | Pemetrexed |

In some embodiments, an antifolate agent (e.g., a pyrimidine-based antifolate agent), such as Pemetrexed, is administered to the subject, before, during, or after administration of the ITZ or PSZ analogues disclosed herein. Pemetrexed is a synthetic pyrimidine-based antifolate. Pemetrexed is also known as LY231514 and (2S)-2-{[4-[2-(2-amino-4-oxo-1,7-dihydropyrrolo[2,3-d]pyrimidin-5-yl)ethyl]benzoyl]amino}pentanedioic acid, and is marked under the brand name N-[4-2-(2-Amino-4,7-dihydro-4-oxo-1H-pyrrolo[2,3-d]pyrimidin-5-yl)ethyl]benzoyl]-1-glutamic acid disodium salt (CAS Number: 150399-23-8). Pemetrexed binds to and inhibits the enzyme thymidylate synthase (TS), which catalyzes the methylation of 2'-deoxyuridine-5'-monophosphate (dUMP) to 2'-deoxythymidine-5'-monophosphate (dTMP), an essential precursor in DNA synthesis.

In some embodiments, a platinum-based agent (coordination complex of platinum) is administered to the subject before, during, or after administration of the ITZ or PSZ analogue disclosed herein. As a class, platinum-based agents are believed to act by causing crosslinking of DNA as a monoadduct, interstrand crosslinks, intrastrand crosslinks, or DNA protein crosslinks, resulting in inhibited DNA repair. In some embodiments, the platinum-based agent is carboplatin, cisplatin, or oxaliplatin, satraplatin, picoplatin, nedaplatin, and triplatin.

The ITZ analogues and PSZ analogues disclosed herein may be administered with one or more immune checkpoint inhibitors, and optionally, an immune modulator. The checkpoint inhibitor may be administered before, during, or after the ITZ analogue or PSZ analogue, and may be administered within the same composition as the ITZ analogue or PSZ analogue, or in a separate composition. Immune checkpoints regulate T cell function in the immune system. T cells play a central role in cell-mediated immunity.

Checkpoint proteins interact with specific ligands which send a signal into the T cell and essentially switch off or inhibit T cell function. Cancer cells take advantage of this system by driving high levels of expression of checkpoint proteins on their surface which results in control of the T cells expressing checkpoint proteins on the surface of T cells that enter the tumor microenvironment, thus suppressing the anticancer immune response. As such, inhibition of checkpoint proteins would result in restoration of T cell function and an immune response to the cancer cells. An immune checkpoint inhibitor (or checkpoint inhibitor) is a compound or agent that blocks or inhibits immune checkpoint proteins (i.e., that blocks or inhibits checkpoint receptors or checkpoint receptor ligands). Examples of checkpoint proteins include, but are not limited to, CTLA-4, PD-L1, PD-L2, PD1, B7-H3, B7-H4, BTLA, HVEM, TIM3, GALS, LAG3, VISTA, IDO, KIR, 2B4 (belongs to the CD2 family of molecules and is expressed on all NK cells, and memory $CD8^+$ T cells), CD160 (also referred to as BY55), CGEN-15049, CHK 1 and CHK2 kinases, A2aR, and various B-7 family ligands. Programmed Death-1 (PD-1) is a member of the immunoglobulin superfamily (IGSF) of molecules involved in regulation of T cell activation. PD-1 acquired its name 'programmed death' when it was identified in 1992 as a gene upregulated in T cell hybridoma undergoing cell death. The structure of PD-1 is composed of one IGSF domain, a transmembrane domain, and an intracellular domain containing an immunoreceptor tyrosine-based inhibitory motif (ITIM) and an immunoreceptor tyrosine-based switch motif (ITSM) [38]. PD-1 has two binding partners: PD-L1 (B7-H1, CD274) and PD-L2 (B7-DC, CD273). PD-L1 is expressed broadly on both hematopoietic and non-hematopoietic lineages. It is found on T cell, B cells, macrophages, NK cells, DCs, and mast cells as well as in peripheral tissues. PD-1 engagement represents one means by which tumors evade immunosurveillance and clearance. Blockade of the PD-1 pathway has been demonstrated by nivolumab, which shows activity in immunocompetent mouse cancer models. Non-limiting examples of checkpoint inhibitors include small molecules, peptides, and antibodies. Non-limiting examples of antibodies include nivolumab (OPDIVO), pembrolizumab (KEYTRUDA), pidilizumab (CT-011), MEDI0680 (AMP-514), AMP-224, AUNP-12, BMS 936559, atezolizumab (MPDL3280A), durvalumab (MEDI4736), avelumab (MSB0010718C), BMS935559 (MDX-1105), rHIgM12B7, BMS-986016, GSK2831781, IMP321, lirilumab (BMS-986015), IPH2101 (1-7F9), Indoximod (NLG 9189), NLG 919, INCB024360, PF-05082566, Urelumab (BMS-663513), and MEDI6469.

EXEMPLIFIED EMBODIMENTS

Embodiment 1. A compound having the structure of Formula (I)

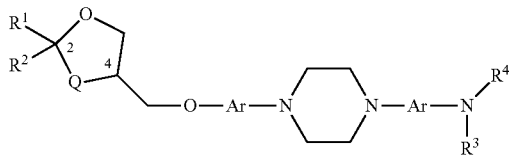

(I)

wherein
Q is O or $CH_2$;
each Ar is independently unsubstituted or substituted aryl;
$R^1$ is $C_{1-6}$ alkyl optionally substituted with an amino (—$NH_2$), a $C_{1-6}$ alkylamino, a $C_{1-6}$ dialkylamino, an N-acylamino, —COOH, an aryl, a heterocycle, pyrrolidine, pyrrole or pyridinyl, group;
$R^2$ is $C_{1-6}$ alkyl or unsubstituted or substituted aryl;
$R^3$ is H or unsubstituted or substituted $C_{1-6}$ alkyl;
$R^4$ is C(=O)—$R^5$, C(=O)—O—$R^5$, or S(=O)$_n$—$R^5$, wherein $R^5$ is $C_{1-6}$ alkyl, unsubstituted or substituted $C_{3-7}$ cycloalkyl, unsubstituted or substituted aryl, unsubstituted or substituted heteroaryl, and n is 0, 1, or 2; or $R^4$ is H or unsubstituted or substituted $C_{1-6}$ alkyl; or $R^3$ and $R^4$ along with the nitrogen atom form a nitro ($NO_2$) group; or $R^3$ and $R^4$ join to form an unsubstituted or substituted 5- or 6-membered ring with the proviso that it does not contain a —N—(=J)-N— moiety where J is O or S;
wherein the substituted groups is substituted with 1, 2, or 3 substituents, each substituent is independently $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl;
a pharmaceutically acceptable salt, a stereoisomeric form thereof, or a combination thereof.

Embodiment 2. The compound of embodiment 1, wherein Q is O; and each Ar is phenyl, pyridine, pyrazine, or pyridazine.

Embodiment 3. The compound of embodiment 1, wherein each Ar is phenyl.

Embodiment 4. The compound of embodiment 1, wherein $R^1$ is methyl or $R^1$ is methyl substituted with one of 1-pyrrole, 3-pyridine, 4-pyridine, phenyl, m-aminophenyl, p-aminophenyl, acetylamine, 1-pyrrolidine, amino, or dimethylamino; and $R^2$ is unsubstituted or substituted phenyl.

Embodiment 5. The compound of embodiment 1, wherein $R^1$ is methyl and $R^2$ is 2,4-dichlorophenyl or 2,4-difluorophenyl.

Embodiment 6. The compound of embodiment 1, wherein $R^4$ is C(=O)—$R^5$ or S(=O)$_n$—$R^5$.

Embodiment 7. The compound of embodiment 6, wherein $R^5$ is unsubstituted or substituted $C_3$-7 cycloalkyl, unsubstituted or substituted aryl, unsubstituted or substituted heteroaryl.

Embodiment 8. A compound having the structure of Formula (Ia)

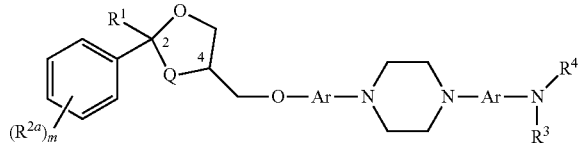

(Ia)

wherein
Q is O or $CH_2$;
each Ar is independently unsubstituted or substituted aryl;
$R^1$ is $C_{1-6}$ alkyl optionally substituted with an amino (—$NH_2$), a $C_{1-6}$ alkylamino, a $C_{1-6}$ dialkylamino, an N-acylamino, —COOH, an aryl, a heterocycle, pyrrolidine, pyrrole or pyridinyl, group;
each $R^{2a}$ independently is $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl;
m is 0, 1, 2, or 3;
$R^3$ is H or unsubstituted or substituted $C_{1-6}$ alkyl;
$R^4$ is C(=O)—$R^5$, C(=O)—O—$R^5$, or S(=O)$_n$—$R^5$, wherein $R^5$ is $C_{1-6}$ alkyl, unsubstituted or substituted $C_{3-7}$ cycloalkyl, unsubstituted or substituted aryl, unsubstituted or substituted heteroaryl, and n is 0, 1, or 2; or $R^4$ is H or unsubstituted or substituted $C_{1-6}$ alkyl; or $R^3$ and $R^4$ along with the nitrogen atom form a nitro ($NO_2$) group; or $R^3$ and $R^4$ join to form an unsubstituted or substituted 5- or 6-membered ring with the proviso that it does not contain a —N—(=J)-N— moiety where J is O or S;
wherein the substituted groups is substituted with 1, 2, or 3 substituents, each substituent is independently $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl; a pharmaceutically acceptable salt, a stereoisomeric form thereof, or a combination thereof.

Embodiment 9. A pharmaceutical composition comprising the compound of any one of embodiments 1-8 and optionally a pharmaceutically acceptable excipient.

Embodiment 10. The pharmaceutical composition of embodiment 9, wherein the composition is a solid dispersion of the compound and a polymer having acidic functional groups.

Embodiment 11. The pharmaceutical composition of embodiment 10, wherein the polymer comprises a polycarboxylic acid.

Embodiment 12. The pharmaceutical composition of embodiment 10 or 11, wherein the polymer comprises hydroxypropyl methylcellulose phthalate.

Embodiment 13. A method of treating a cell proliferation disorder in a subject in need thereof, comprising administering a therapeutically effective amount of the compound of any one of embodiments 1-8, or pharmaceutical composition of any one of embodiments 9-12.

Embodiment 14. The method of embodiment 13, wherein the cell proliferation disorder is dependent upon the Hh signaling pathway.

Embodiment 15. The method of embodiment 13 or 14, wherein the cell proliferation disorder is a non-cancerous cell proliferation disorder.

Embodiment 16. The method of embodiment 13 or 14, wherein the cell proliferation disorder is cancer.

Embodiment 17. The method of embodiment 16, wherein the cancer is basal cell carcinoma (BCC) or medulloblastoma (MB).

Embodiment 18. The method of embodiment 16, wherein the cancer is resistant to Vismodegib.

Embodiment 19. The method of embodiment 16, wherein the cancer is chronic myeloid leukemia, lung cancer, prostate cancer, pancreatic cancer or bone cancer.

Embodiment 20. A liposome formulation comprising the compound of any one of embodiments 1-8 or a compound having the structure of Formula (II):

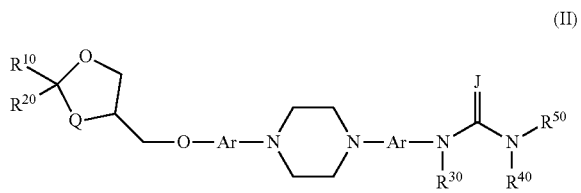

wherein

Q is O or $CH_2$, specifically O;

each Ar is independently unsubstituted or substituted aryl, specifically phenyl, pyridine, pyrazine, or pyridazine, and more specifically phenyl;

J is O or S, specifically O;

$R^{10}$ is $C_{1-6}$ alkyl optionally substituted with an amino, a $C_{1-6}$ alkylamino, a $C_{1-6}$ dialkylamino, an N-acylamino, —COOH, an aryl, a heterocycle, pyrrolidine, pyrrole, or pyridinyl group, specifically $R^{10}$ is methyl, optionally substituted with 1-pyrrole, 3-pyridine, 4-pyridine, phenyl, m-aminophenyl, p-aminophenyl, acetylamine, 1-pyrrolidine, amino, or dimethylamino, and more specifically $R^{10}$ is methyl;

$R^{20}$ is $C_{1-6}$ alkyl or unsubstituted or substituted aryl, specifically unsubstituted or substituted phenyl, and more specifically $R^{20}$ is 2,4-dichlorophenyl or 2,4-difluorophenyl;

$R^{30}$ is H or unsubstituted or substituted $C_{1-6}$ alkyl;

$R^{40}$ is H or unsubstituted or substituted $C_{1-6}$ alkyl; or $R^{30}$ and $R^{40}$ join to form an unsubstituted or substituted 5- or 6-membered ring with the —N—(=J)-N— moiety where $R^{30}$ and $R^{40}$ form a unsubstituted or substituted $C_2$-3 carbohydryl group or a unsubstituted or substituted $C_{1-2}$ carbohydryl group linked via a nitrogen to a nitrogen of the —N—(=J)-N— moiety;

$R^{50}$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$ alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_{1-6}$ haloalkoxy;

a pharmaceutically acceptable salt, a stereoisomeric form thereof, or a combination thereof.

Embodiment 21. A method of treating cell proliferation disorder in a subject in need thereof, comprising administering a therapeutically effective amount of the liposome formulation of embodiment 20.

Embodiment 22. The method of embodiment 21, wherein the cell proliferation disorder is dependent upon the Hh signaling pathway.

Embodiment 23. The method of embodiment 21 or 22, wherein the cell proliferation disorder is a non-cancerous cell proliferation disorder.

Embodiment 24. The method of embodiment 21 or 22, wherein the cell proliferation disorder is cancer.

Embodiment 25. The method of embodiment 24, wherein the cancer is basal cell carcinoma (BCC) or medulloblastoma (MB).

Embodiment 26. The method of embodiment 24, wherein the cancer is resistant to Vismodegib.

Embodiment 27. The method of embodiment 24, wherein the cancer is chronic myeloid leukemia, lung cancer, prostate cancer, pancreatic cancer or bone cancer.

All patents, patent applications, provisional applications, and publications referred to or cited herein, supra or infra, are incorporated by reference in their entirety, including all figures and tables, to the extent they are not inconsistent with the explicit teachings of this specification.

The invention is further illustrated by the following non-limiting examples.

EXAMPLES

Example A: Itraconazole (ITZ) Analogues

Itraconazole (ITZ) is an FDA-approved antifungal agent that has several additional biological activities, including anti-cancer and anti-viral properties. With respect to its anti-cancer properties, ITZ inhibits the hedgehog (Hh) pathway, an embryonic cell-signaling cascade responsible for cell proliferation, differentiation, and tissue growth. Aberrant Hh pathway activation has been identified in a variety of cancers; most notably, basal cell carcinoma (BCC) and medulloblastoma (MB). Previous studies suggest that ITZ inhibits Hh signaling through direct binding interactions with Smoothened (Smo), a key regulatory protein within the Hh pathway. These studies also suggest that ITZ binds Smo in a distinct manner from other Hh pathway inhibitors that function through Smo antagonism. A common pitfall for Smo antagonists has been the emergence of resistance due to mutations in the binding site on Smo; however, ITZ maintains potent Hh pathway inhibition in the presence of both wild type and mutant forms of Smo, presumably through its distinct binding interactions.

Chart 1. Initial SAR for the ITZ scaffold.

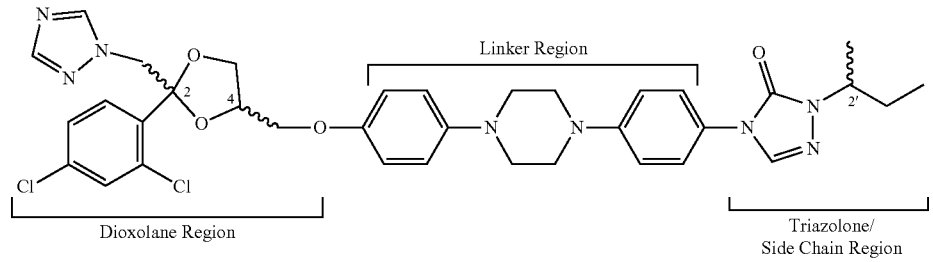

Dioxolane Region | Linker Region | Triazolone/Side Chain Region

1, ITZ
$IC_{50}$ = 140 nm

-continued

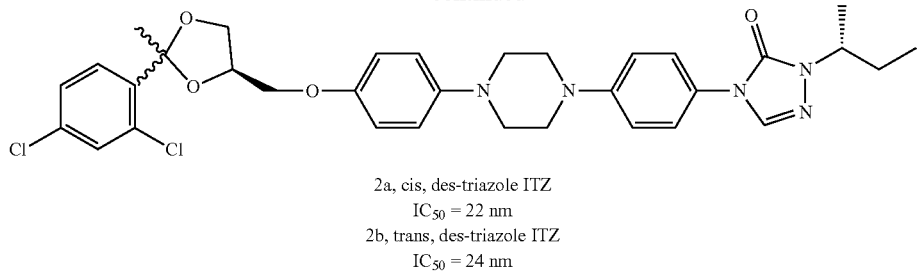

2a, cis, des-triazole ITZ
$IC_{50} = 22$ nm
2b, trans, des-triazole ITZ
$IC_{50} = 24$ nm ITZ consists of a diverse scaffold that is amendable to modification. Previous structure activity relationship (SAR) studies for ITZ, which indicated the functionality and stereochemistry that provides potent Hh pathway inhibition. These SAR studies have resulted in a novel class of Hh pathway inhibitors: des-triazole ITZ analogues. In addition to removing the triazole moiety, the stereochemistry around the dioxolane (4R) was found to be important for potent Hh pathway inhibition. The studies also demonstrated that the absolute stereochemistry of the side chain is less important; however, the methyl of the sec-butyl region allows for maintaining potent Hh pathway inhibition. In addition, several analogues that truncated or completely removed the triazolone and side chain retained potent Hh pathway inhibition. Continued SAR for the des-triazole ITZ scaffold is reported herein. These studies focus on the synthesis and evaluation of analogues containing a wide range of structural modifications to the triazolone/side chain region of lead ITZ analogue 2.

Example 1: Preparation of Des-Triazole ITZ Analogues

The preparation of des-triazole ITZ analogues containing a modified triazolone region starts with direct coupling of the desired dioxolane (3 or 4) with the unprotected linker region (5) to provide key intermediates 6 or 7. The dioxolane-containing nitro was reduced to the aniline in the presence of 10% Pd/C and hydrazine monohydrate (Scheme 1). These key aniline intermediates (8 and 9) can be utilized to provide the most efficient synthetic route towards a diverse set of ITZ analogues that contain modifications to the triazolone/side chain region.

Scheme 1. Synthesis of Aniline Intermediates[a]

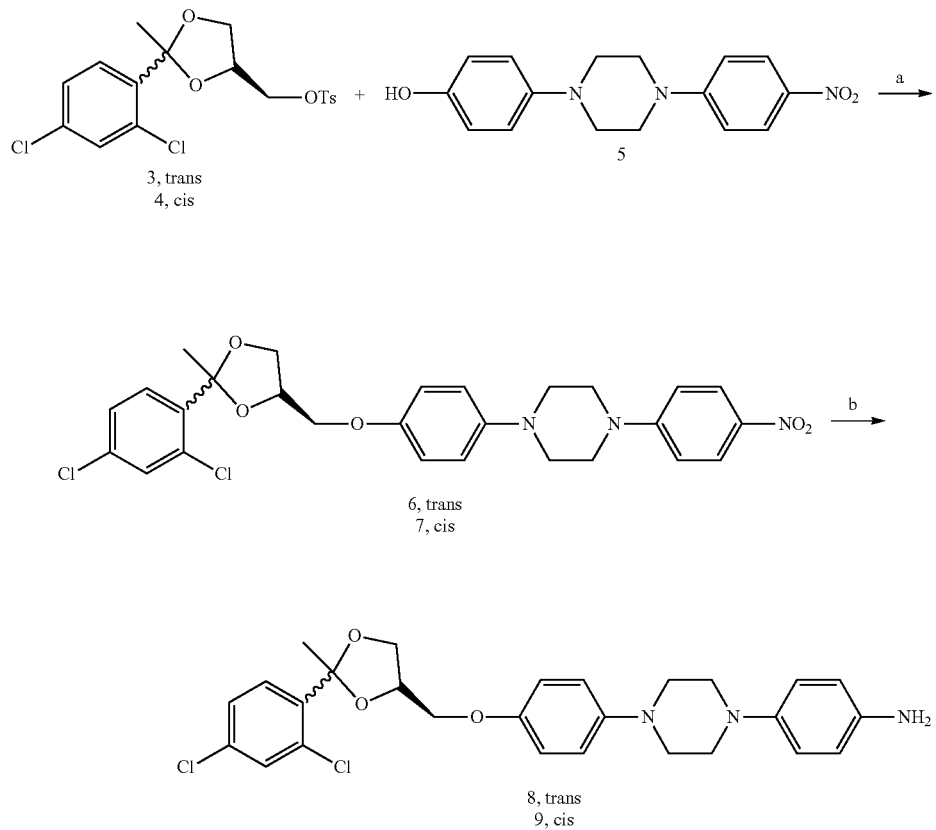

*Reagents and conditions: (a) Cs₂CO₃ (10 eq), DMSO, 90° C., 12 h, 34-85%; (b) 10% Pd/C, hydrazine monohydrate, EtOH, reflux, 3.5 h, 42%-94%.

The majority of des-triazole analogues synthesized and evaluated in this study simplified the ITZ scaffold by replacing the triazolone and side chain with a substituted aromatic moiety directly appended to the aniline of 8 or 9. Synthesis towards these amide analogues (10-19) utilized standard amidation conditions: aniline (8 or 9), activating agent 1-ethyl-3-(3-dimethylaminopropyl)carboniimide (EDCI), 4-dimethylaminopyridine (DMAP), and various carboxylic acids stirred in DCM at room temperature for 12 hours (Scheme 2). While yields in this reaction were less than ideal (<50%) further optimization was not undertaken.

Scheme 2. Initial Synthesis of Des-Triazole Amide Analogues*

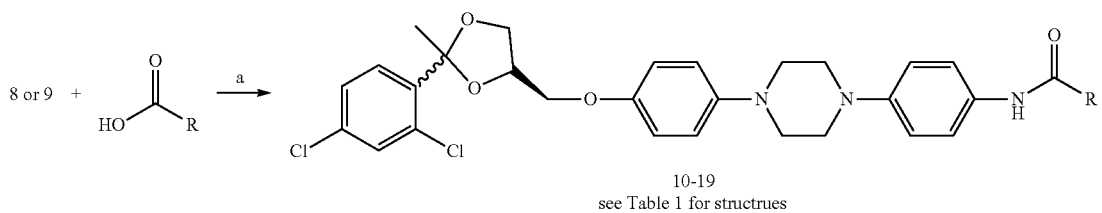

10-19
see Table 1 for structrues

*Reagents and conditions: (a) EDCI, DMAP, DCM, RT, 12 h, <50%.

The synthetic route described in Scheme 2 worked well to generate all the amide-containing analogues with the exception of those incorporating a phenol-substituted phenyl ring. Under these standard conditions, the amide couplings with the phenol carboxylic acids reaction did not proceed, presumably because the free phenol becomes activated allowing for multiple side reactions to occur. Synthesis of these analogues was achieved by protecting the free phenols of the corresponding aromatic esters with the benzyl ether (Scheme 3). Ideally, the benzyl (Bn) group could be removed under mild conditions (palladium on carbon/hydrogen) that would not affect the intact dioxolane. This synthetic approach provided the desired phenol-substituted analogues; however, the compounds, except for compound 30, were obtained in very low yields after the final hydrogenation reaction (<20%).

Scheme 3. Couplings Procedures for Phenols and 2nd Generation ITZ Amides*

(A)

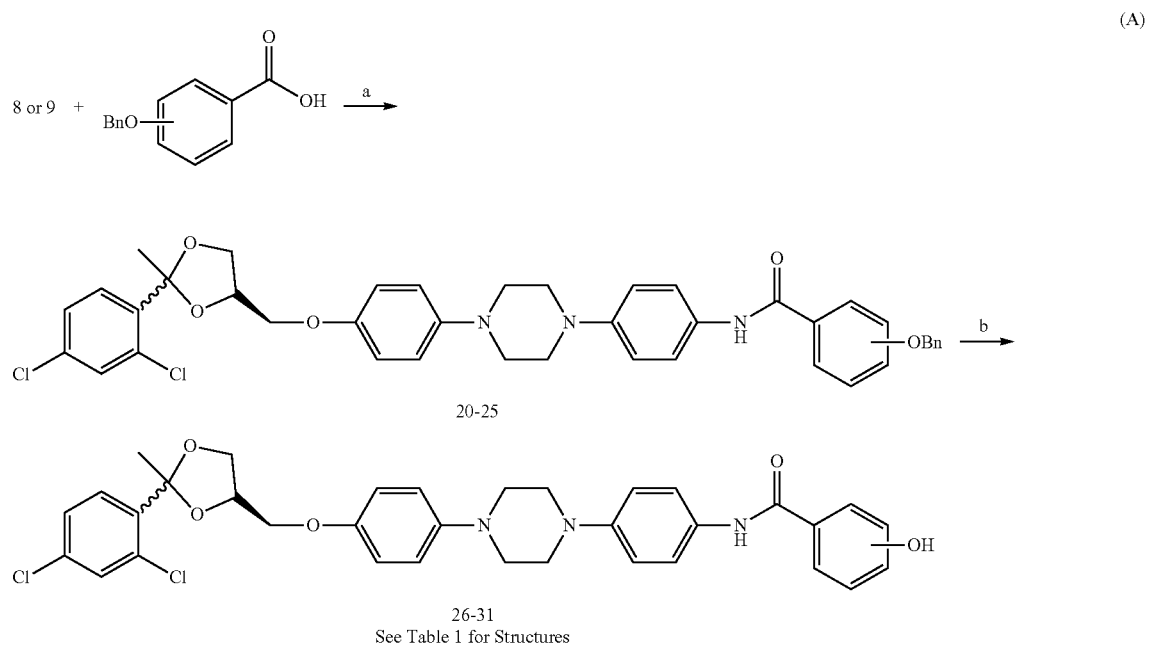

20-25

26-31
See Table 1 for Structures

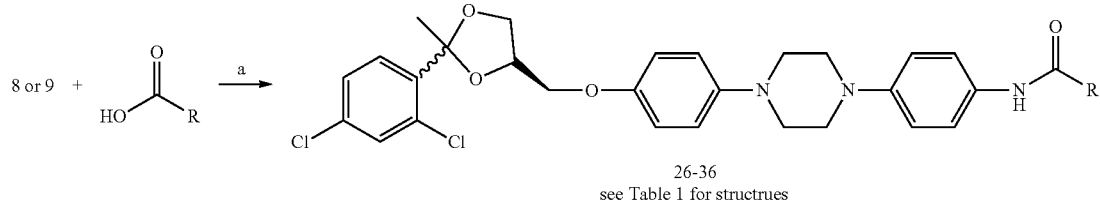

(B)

26-36
see Table 1 for structrues

<sup>a</sup>Reagents and conditions: (a) EDCI, DMAP, DCM, RT, 12 h, <50%; (b) 10% Pd/C, THF:EtOH, H₂, <20%; (c) HATU, NMM, DMF, RT, 12 h, 8-31%.

In an attempt to obtain higher yields for the analogues incorporating a phenol, N-methylmorpholine (NMM) and 1-[bis(dimethylamino)methylene]-1H-1,2,3-triazolo[4,5,6]pyridinium3-oxidhexafluorophosphate (HATU) were utilized in dimethyl formamide (Scheme 4). While obtaining higher yields was unsuccessful, these conditions allowed for an efficient direct coupling of the carboxylic acid of the free phenol to the aniline intermediates (8/9) to yield our final analogues (26-31). With the increased efficiency of these conditions (NMM/HATU), they were also utilized for subsequent second generation des-triazole ITZ amide analogues (32-36, Table 5) in combination with the original amide coupling conditions (EDCI/DMAP).

TABLE 4

First Generation Des-Triazole ITZ Amide Analogues.

| Cmpd | R₁ | R₂ |
|---|---|---|
| 6 | (2,4-dichlorophenyl dioxolane methyl ether, 2R,4R) | -NO₂ |
| 7 | (2,4-dichlorophenyl dioxolane methyl ether, 2S,4S) | -NO₂ |
| 8 | (2,4-dichlorophenyl dioxolane methyl ether, 2R,4R) | -NH₂ |
| 9 | (2,4-dichlorophenyl dioxolane methyl ether, 2S,4S) | -NH₂ |
| 10 | (2,4-dichlorophenyl dioxolane methyl ether, 2R,4R) | -NHC(O)Ph |

TABLE 4-continued

First Generation Des-Triazole ITZ Amide Analogues.

R₁—O—⟨phenyl⟩—N(piperazine)N—⟨phenyl⟩—R₂

| Cmpd | R₁ | R₂ |
|---|---|---|
| 11 | 2,4-dichlorophenyl-(2-methyl-1,3-dioxolan-4-yl)methoxy- (2R,4S) | -NH-C(O)-naphthalen-2-yl |
| 12 | 2,4-dichlorophenyl-(2-methyl-1,3-dioxolan-4-yl)methoxy- (2R,4S) | -NH-C(O)-pyridin-2-yl |
| 13 | 2,4-dichlorophenyl-(2-methyl-1,3-dioxolan-4-yl)methoxy- (2R,4S) | -NH-C(O)-pyridin-3-yl |
| 14 | 2,4-dichlorophenyl-(2-methyl-1,3-dioxolan-4-yl)methoxy- (2R,4S) | -NH-C(O)-pyridin-4-yl |
| 15 | 2,4-dichlorophenyl-(2-methyl-1,3-dioxolan-4-yl)methoxy- (2S,4S) | -NH-C(O)-phenyl |
| 16 | 2,4-dichlorophenyl-(2-methyl-1,3-dioxolan-4-yl)methoxy- (2S,4S) | -NH-C(O)-naphthalen-2-yl |
| 17 | 2,4-dichlorophenyl-(2-methyl-1,3-dioxolan-4-yl)methoxy- (2S,4S) | -NH-C(O)-pyridin-2-yl |
| 18 | 2,4-dichlorophenyl-(2-methyl-1,3-dioxolan-4-yl)methoxy- (2S,4S) | -NH-C(O)-pyridin-3-yl |
| 19 | 2,4-dichlorophenyl-(2-methyl-1,3-dioxolan-4-yl)methoxy- (2S,4S) | -NH-C(O)-pyridin-4-yl |

TABLE 4-continued

First Generation Des-Triazole ITZ Amide Analogues.

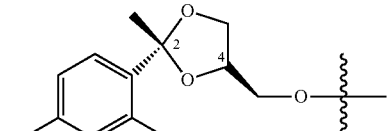

| Cmpd | R₁ | R₂ |
|---|---|---|
| 26 | 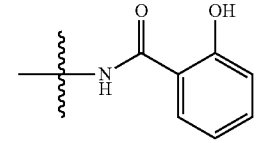 [SMILES: *NC(=O)c1ccccc1O] | 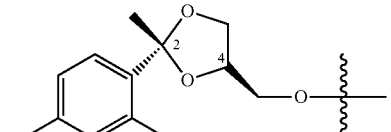 |
| 27 | 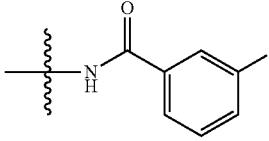 | 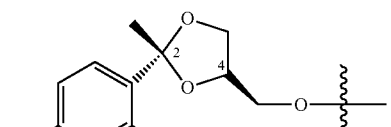 |
| 28 | 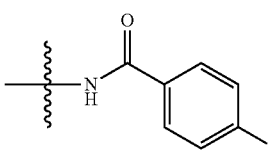 | 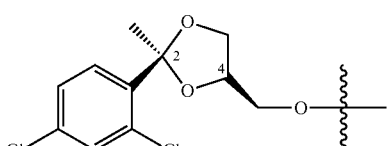 |
| 29 | 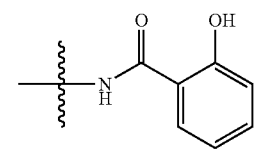 [SMILES: *NC(=O)c1ccccc1O] | 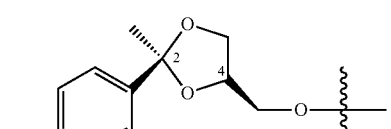 |
| 30 | 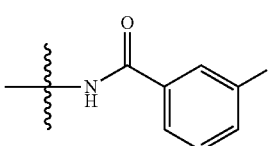 | 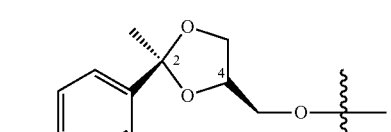 |
| 31 | 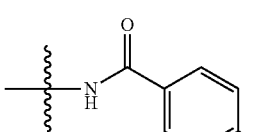 | |

Des-triazole ITZ analogues containing carbamate, hydrazine carboxamide, or an unsubstituted triazolone were synthesized in a similar manner as previously described for the synthesis of ITZ and other analogues (Scheme 5). The carbamates 37 and 38 were generated through the addition of phenyl chloroformate to anilines 8 and 9, respectively. Addition of hydrazine monohydrate to the carbamates provided the hydrazine carboxamides 39 and 40. Finally, the intact triazolones were generated following the addition of formamidine acetate to 41 and 42.

TABLE 5

Second Generation of Des-ITZ Amide Analogues

| Compound | R₁ | R₂ |
|---|---|---|
| 32 | 2,4-dichlorophenyl-2-methyl-1,3-dioxolan-4-yl-methyl | 3-chlorobenzamide |
| 33 | 2,4-dichlorophenyl-2-methyl-1,3-dioxolan-4-yl-methyl | 3-methoxybenzamide |
| 34 | 2,4-dichlorophenyl-2-methyl-1,3-dioxolan-4-yl-methyl | 3-acetylbenzamide |
| 35 | 2,4-dichlorophenyl-2-methyl-1,3-dioxolan-4-yl-methyl | furan-3-carboxamide |
| 35 | 2,4-dichlorophenyl-2-methyl-1,3-dioxolan-4-yl-methyl | thiophene-3-carboxamide |

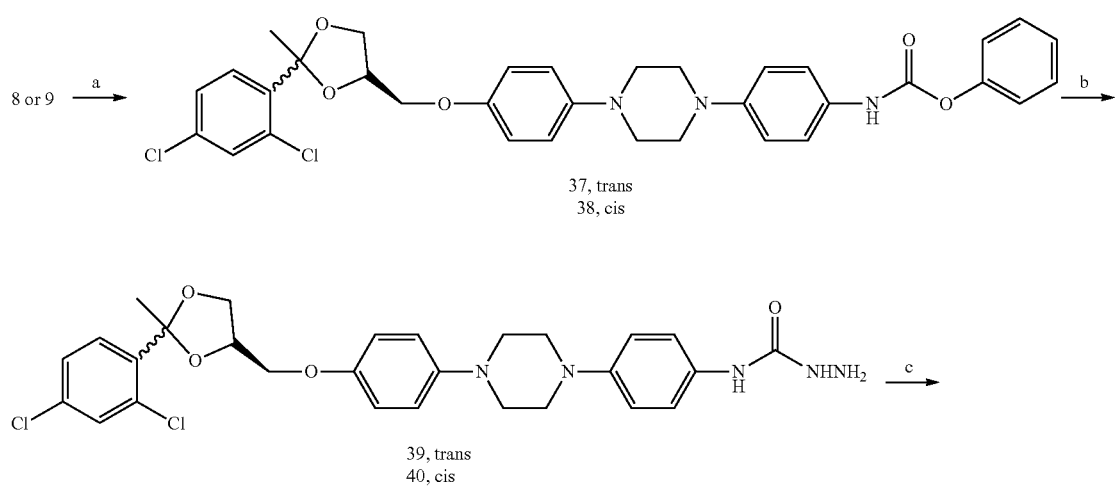

Scheme 5. Synthesis of Des-Triazole Triazolone Precursors<sup>a</sup>

37, trans
38, cis 39, trans
40, cis

-continued

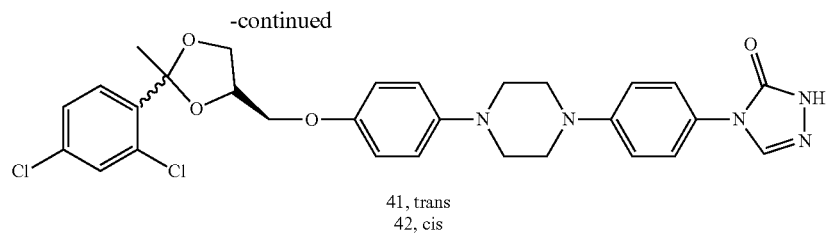

41, trans
42, cis

[a]Reagents and conditions: (a) Pyr (17 eq), ClCOOPh (1.1 eq), 3 h, 78-81%; (b)NH$_2$NH$_2$—H$_2$O (5.5 eq), reflux, 3 h, 88-89%; (c) formamidine acetate (4.5 eq), acetic acid, reflux, 3 h, 20-46%.

Biological Evaluation

Initial Hh inhibition studies. All des-triazole ITZ analogues were initially evaluated for Hh pathway inhibition by monitoring endogenous Gli1 mRNA levels in the murine BCC cell line ASZ-001. Previous SAR studies indicated that the ASZ cells represents a more appropriate cellular model for measuring des-triazole ITZ analogue Hh pathway activity compared to the C3H10T1/2 and NIH-3T3 mouse embryonic fibroblasts (MEFs) commonly used for evaluating inhibition of Hh signaling. Anti-Hh activity in the ASZ cell line correlated more closely with a primary Hh-dependent murine MB cell line isolated from conditional patched knockout (Math1-Cre-ER; Ptc$^{fl/fl}$, MERP) mice.

As shown above for lead analogue 2, initial SAR studies suggested that the trans, 4R orientation around the dioxolane resulted in potent Hh pathway inhibition. In addition, initial compounds suggested that truncation of the triazolone region of the scaffold was tolerated. With this in mind, the initial plan for this generation of ITZ analogues was to synthesize and evaluate a series of compounds that replaced the triazolone moiety with substituted phenyl groups directly appended to the linker region through an amide bond. Substituted amides were chosen based on their general stability (chemical and biological), enhanced solubility, and ease of synthesis.

The first series of des-triazole ITZ analogues focused on analogues that contained the 2R,4R-trans-dioxolane for the reasons noted above (6, 8, 10-14, 26-28, Table 4). Both truncated analogues (6 and 8) exhibited moderate Hh inhibition (IC$_{50}$=0.31±0.04 μM and 0.92±0.04 respectively); however, the majority of compounds containing an amide in place of the triazolone were inactive at the concentrations tested (Table 6). Despite reduced potency within this trans series of des-triazole ITZ amides, the SAR data did indicate that substitutions in the meta-position of the phenyl ring were most favorable as 13 (3-pyridyl) was moderately active (IC$_{50}$=4.3±0.2 μM) and 27 (3-phenol) demonstrated potent Hh inhibition (IC$_{50}$=0.19±0.01 μM) compared to the ortho- and para-substituted analogues. These results suggest that functional groups capable of hydrogen bonding at the meta-position may be advantageous to binding with Smo, the hypothesized target of ITZ and ITZ analogues.

TABLE 6

In Vitro Activity of First Generation Des-ITZ Amide Analogues

| Compound | IC$_{50}$ (μM)$^{a, b}$ | MERP |
|---|---|---|
| 6 | 0.31 ± 0.04 | |
| 7 | 0.26 ± 0.04 | |
| 8 | 0.92 ± 0.04 | |
| 9 | 0.39 ± 0.09 | |
| 10 | >10 | |

TABLE 6-continued

In Vitro Activity of First Generation Des-ITZ Amide Analogues

| Compound | IC$_{50}$ (μM)$^{a, b}$ | MERP |
|---|---|---|
| 11 | >10 | |
| 12 | >10 | |
| 13 | 4.3 ± 0.2 | >10 |
| 14 | >10 | |
| 15 | >10 | |
| 16 | >10 | |
| 17 | 3.9 ± 0.3 | |
| 18 | 0.19 ± 0.09 | 1.1 ± 0.6 |
| 19 | >10 | |
| 26 | >10 | |
| 27 | 0.19 ± 0.01 | 2.8 ± 1.5 |
| 28 | >10 | |
| 29 | 2.2 ± 0.3 | |
| 30 | 0.16 ± 0.03 | 0.35 ± 0.06 |
| 31 | 3.0 ± 0.1 | |

$^a$IC$_{50}$ values represent the Mean ± SEM of at least two separate experiments performed in triplicate.
$^b$All analogues evaluated following 48 h incubation.

As noted, initial focus was on the synthesis and evaluation of ITZ amides on the trans-dioxolane because of the activity of this stereochemical orientation in the first generation series; however, several cis-dioxolane ITZ analogues also demonstrated potent Hh inhibition. With this in mind, cis-dioxolane amides were prepared with the same substituents to determine what effect this modification would have on Hh inhibitory activity of the scaffold (7, 9, 15-19, 29-31, Table 6). Interestingly, each of the cis-dioxolane analogues was more potent than its corresponding trans-dioxolane suggesting that this orientation was preferred when the triazolone was substituted with the simplified aromatic moiety. In addition, analogues containing the 3-pyridyl (18, IC$_{50}$=0.19 μM) or 3-phenol (30, IC$_{50}$=0.16 μM) were the most potent for the cis-dioxolane.

Based on the SAR generated from our first series of amide-containing ITZ analogues, several more compounds that incorporated the cis-dioxolane and a meta-substituted aromatic moiety were synthesized and evaluated (Table 7). These analogues were designed to further probe the sterics, electronics, and hydrogen bonding of the substituents in the meta-position. Analogues containing a furan (35) or thiofuran (36) were inactive, suggesting 5-membered rings may not be capable of inhibiting the Hh pathway (Table 7). Masking the phenol of 30 as the methoxy (33) decreased potency supporting a role for increased polarity in the meta-position (IC$_{50}$ values=5.7 μM and 0.16 μM, respectively). The most potent analogue in this second series, and the most potent amide analogue prepared, was 34 (IC$_{50}$=0.089 which contains the 3-acetyl phenyl ring. Based on the results, and not wishing to be bound by theory, potent inhibition of the Hh pathway can be correlated to the ability to hydrogen bond and/or increased polarity at the meta-position of the phenyl ring for cis-dioxolane analogues incorporating a substituted aromatic moiety for the triazolone.

TABLE 7

In Vitro Evaluation of Second Generation Des-ITZ Amide Analogues

| Compound | IC$_{50}$ (μM)[a, b] | MERP GI$_{50}$ (μM) |
|---|---|---|
| 32 | >10 | |
| 33 | 5.7 ± 1.9 | |
| 34 | 0.089 ± 0.01 | 1.0 ± 0.3 |
| 35 | >10 | |
| 36 | >10 | |

[a]IC$_{50}$ values represent the Mean ± SEM of at least two separate experiments performed in triplicate.
[b]All analogues evaluated following 48 h incubation.

In parallel with the studies of ITZ analogues that contain amides as isosteres of the triazolone ring, the stereochemically unsubstituted triazolones (41 and 42) were synthesized and evaluated. Earlier SAR demonstrated that the side chain was not required for Hh inhibitory activity, but the defined cis- and trans-dioxolane analogues were not evaluated. The Hh inhibitory activity of several synthetic precursors to the triazolone were also explored (37-40). In addition to a shorter synthetic route, the functional groups on these precursors may aid in improving the overall drug-like properties of this scaffold. Carbamates have been widely studied within the field of medicinal chemistry and are key structural motifs in many FDA-approved compounds and prodrugs because they offer chemical stability and enhanced cell permeability. Hydrazine carboxamides are derivatives of urea and have thus been studied extensively within the field of drug development and may aid in hydrogen-bonding and solubility. Not surprisingly, both of the intact triazolones (41 and 42) were potent inhibitors of Hh signaling (IC$_{50}$ values=0.14 and 0.21 respectively, Table 8), similar to previous results for the undefined triazolone analogue (IC$_{50}$=0.12 μM). The most potent analogues for the triazolones and precursors were the two hydrazine carboxamides (39 and 40) and similar to the ITZ amides, the cis-hydrazine was more potent than the corresponding trans-analogue. In fact, the most potent analogue generated through these studies was the cis-dioxolane hydrazine (IC$_{50}$=0.009 Not wishing to be bound by theory, but the enhanced inhibitory activity for the hydrazine carboxamides may be due to their increased polarity and hydrogen bond donating/accepting properties. In addition, the hydrazine carboxamide is an acyclic functionality, providing strong evidence that anti-Hh activity can still be achieved without the cyclic functionality of the triazolone and aromatic isosteres. The carbamate analogues were inactive, which may be attributed to the presence of the bulky non-substituted hydrophobic ring.

TABLE 8

In Vitro Evaluation of Des-ITZ Intermediate Analogues

| Compound | IC$_{50}$ (μM)[a, b] | MERP |
|---|---|---|
| 37 | >10 | |
| 38 | >10 | |
| 39 | 0.11 ± 0.01 | 0.5 ± 0.4 |
| 40 | 0.009 ± 0.0002 | 2.8 ± 0.9 |
| 41 | 0.14 ± 0.03 | |
| 42 | 0.21 ± 0.04 | |

[a]IC$_{50}$ values represent the Mean ± SEM of at least two separate experiments performed in triplicate.
[b]All analogues evaluated following 48 h incubation.

Secondary In Vitro Evaluation. Based on their activity in ASZ cells, several compounds were evaluated further in a primary murine Hh-dependent MB cell line (MERP).

Preliminary In Vitro Pharmacokinetic Assays. In parallel with the secondary evaluation of promising compounds against MERP and mutant forms of SMO, several compounds were chosen for evaluation in a series of preliminary pharmacokinetic (PK) assays. The amide substituents did not aid in solubility. The half-life did not significantly change between ITZ and 30. Interestingly, stereoisomers 13 and 18 had significantly different half-lives suggesting that the stereochemistry plays a role in compound metabolism and clearance. It was previously determined that the removal of the triazole group abolishes inhibition of CYPA4 and this also translates over to the des-triazole ITZ analogues with amide functionality. Lastly, as these compounds are being targeted to treat MB, they were screened in a parallel artificial membrane permeability assay (PAMPA) for their ability to passively permeate cell membranes. While ITZ had a moderate PAMPA permeability, none of the des-triazole ITZ analogues were able to passively cross this artificial membrane barrier (Table 9).

TABLE 9

Pharmacokinetic Evaluation of Des-Triazole ITZ Amide Analogues

| | T$_{1/2}$ (HLM, min) | Solubility (μM) | PAMPA | CYP3A4 (μM) | BCRP | P-gp | Clearance |
|---|---|---|---|---|---|---|---|
| ITZ | 27.0 ± 6.2 | 0.8 | Moderate | 0.04 | No | No | — |
| 2a | ND | 0.8 | Poor | >20 | No | No | — |
| 2b | ND | 1.56 | Poor | 1.02 | No | No | — |
| 13 | 59.9 ± 2.0 | 0.0042 | Poor | >30 | — | — | 11.6 ± 0.4 |
| 18 | 8.9 ± 0.03 | 0.0069 | Poor | >20 | No | No | 78.3 ± 0.2 |
| 27 | >231 | 0.0014 | — | >30 | — | — | <3 |
| 30 | 19.9 ± 0.6 | 0.0016 | Poor | 11.4 | — | — | 34.7 ± 1.0 |
| 34 | 11.4 ± 0.06 | 0.0014 | — | >30 | — | — | 61.0 ± 0.3 |
| 39 | 20.1 ± 0.6 | 0.0093 | — | >30 | — | — | 34.5 ± 0.9 |
| 40 | 11.5 ± 0.1 | 0.0014 | — | >30 | — | — | 60.4 ± 0.7 |

Discussion and Conclusions

Two generations of des-triazole ITZ analogue generations were designed, synthesized, and evaluated for their ability to inhibit the Hh pathway. The goal of these analogues was to further probe the sterics, electronics, and hydrogen bonding in the triazolone/side-chain region of the ITZ scaffold. Des-triazole ITZ analogues contained the optimal stereochemically-defined dioxolane regions determined from previous SAR studies. The triazolone/side-chain region was replaced with various functionalities: amide, carbamate, hydrazine carboxamide, or triazolone. Des-triazole ITZ amide analogues results determined that the 2S,4R-cis-amides were more potent than the 2R,4R-trans-amide analogues. In addition, different substituents and positions around the phenyl ring were explored to determine if either of these components was important for potent Hh pathway inhibition. The most potent des-triazole ITZ amide analogues contained the 4R-cis-dioxolane regions and meta-substitution around the phenyl ring. Generally, anti-Hh activity becomes more potent with increasing meta-substituent polarity.

Although alcohols and amines are typically more polar than ketones, other characteristics of this functional group may be attributing to its potent activity such as its electron-withdrawing nature. In addition, the bond length of the carbonyl in combination with the position of the oxygen atom, may allow for tighter binding to a particular residue within the Smo binding pocket. Interestingly, posaconazole (PSZ), an azole antifungal structurally similar to ITZ, also serves as an Hh pathway inhibitor. PSZ differs from ITZ in that it contains a hydroxylated side-chain region; this supports the addition of polar moieties to the triazolone/side-chain region to maintain potency with the potential of improving overall drug-like properties.

Experimental Chemical Synthesis

General Information. All chemicals were purchased from either Sigma-Aldrich or Fisher Scientific. ACS grade methanol, ethyl acetate, toluene, anhydrous DMF, DCM, and DMSO were purchased from Fisher Scientific or Sigma-Aldrich. All reactions were performed under an argon atmosphere. NMR data were collected on a Bruker AVANCE 500 MHz spectrometer, and analysis was carried out using MestReNova. HRMS data was obtained at the Mass Spectrometry Facility at the University of Connecticut. FT-IR analysis was carried out on a Bruker Alpha Platinum ATR instrument using OPUS software (v7.2). The preparation of previously characterized ITZ intermediates (3-5) followed known procedures with minor modifications. (Shi et al., ACS Med. Chem. Lett. 2010, 1 (4), 155-159; Shi et al. J. Med. Chem. 2011, 54 (20), 7363-7374; Heeres et al., J. Med. Chem. 1984, 27 (7), 894-900; and Tanoury et al. Tetrahedron: Asymmetry 2003, 14 (22), 3487-3493.) All ITZ analogues evaluated in the biological assays were greater than 95% pure based on the HPLC methods described below.

Purity Analysis of Final Analogues. Purity analysis of all final des-triazole ITZ analogues was determined via one of the methods described below.

Method A. ITZ analogues were dissolved in HPLC-grade MeCN and injected (25 µL of a 1 mM solution) into an Agilent Manual FL-Injection Valve (600 bar) on an Agilent 1100/1200 Series HPLC equipped with an Agilent Eclipse Plus C18 (4.6×100 mm) column and Agilent 1100 Series Photodiode Array Detector. The mobile phase consisted of 70% MeCN/30% $H_2O$. All analogues were run at a flow rate of 1.0 mL/min for 20 min and purity was assessed at 254 nm.

Method B. ITZ analogues were dissolved in HPLC-grade MeCN and injected (25 µL of a 1 mM solution) into an Agilent HPLC system coupled to an Agilent ESI single quadrupole mass spectrometer equipped with a Kinetix C18 (150×4.6 mm) column and an Agilent G1315 diode array detector. The mobile phase was a gradient of 25%-100% MeCN (0.1% formic acid) in water over 75 min. All analogues were run at a flow rate of 0.7 mL/min for 30 min and purity was assessed at 254 nm.

1-(4-(((2R,4R)-2-(2,4-dichlorophenyl)-2-methyl-1,3-dioxolan-4-yl)methoxy)phenyl)-4-(4-nitrophenyl)piperazine (6). To a solution of 5 (0.77 g, 2.61 mmol) in DMSO (30 mL) was added $Cs_2CO_3$ (8.5 g, 26.14 mmol) and 3 (1.2 g, 2.87 mmol). The solution was warmed to 90° C. and stirred for 12 h. The mixture was cooled to room temperature and water was added slowly with vigorous stirring (~20 mL). A yellow precipitate formed, which was filtered and recrystallized in EtOH to yield 6 (1.2 g, 85%). $^1$H NMR (500 MHz, $CDCl_3$) δ 8.28-8.14 (m, 2H), 7.66 (d, 1H), 7.46 (d, 1H), 7.28 (m, 1H), 7.03-6.87 (m, 6H), 4.37 (m, 1H), 4.16 (m, 1H), 4.11-3.95 (m, 2H), 3.89 (m, 1H), 3.69-3.53 (m, 4H), 3.35-3.18 (m, 4H), 1.86 (s, 3H). $^{13}$C NMR (126 MHz, $CDCl_3$) δ 153.29, 134.59, 131.21, 128.89, 126.79, 125.98, 118.58, 115.56, 112.90, 109.99, 109.12, 77.28, 77.02, 76.77, 73.94, 69.27, 66.99, 50.39, 47.31, 25.73. DART-HRMS: m/z calcd. for $C_{27}H_{27}C_{12}N_3O_5$ [MH]$^+$, 544.1406; Found: 544.1388. IR (solid) vmax: 3060, 2926, 2880, 2828, 1556, 1507, 1485, 1446, 1376, 1222, 1190, 1142, 1047, 995, 942, 821, 737. Purity, Method A: 95.2%.

1-(4-(((2S,4R)-2-(2,4-dichlorophenyl)-2-methyl-1,3-dioxolan-4-yl)methoxy)phenyl)-4-(4-nitrophenyl)piperazine (7). To a solution of 5 (260 mg, 0.87 mmol) in DMSO (20 mL) was added $Cs_2CO_3$ (3.1 g, 9.58 mmol) and 4 (400 mg, 0.0958 mmol). The solution was warmed to 90° C. and stirred for 12 h. The mixture was cooled to room temperature and water was added slowly with vigorous stirring (~10 mL). A yellow precipitate formed, which was filtered and recrystallized in EtOH to yield 8 (175 mg, 34%) $^1$H NMR (500 MHz, $CDCl_3$) δ 8.22-8.17 (m, 2H), 7.68 (d, 1H), 7.42 (d, 1H), 7.24 (m, 1H), 6.96-6.89 (m, 4H), 6.81-6.76 (m, 2H), 4.65 (m, 1H), 4.35 (m, 1H), 3.99 (m, 1H), 3.81-3.76 (m, 2H), 3.64-3.59 (m, 4H), 3.26 (m, 4H), 1.83 (s, 3H). $^{13}$C NMR (126 MHz, $CDCl_3$) δ 154.78, 153.09, 145.50, 139.34, 138.76, 134.35, 132.82, 130.97, 128.55, 126.70, 125.98, 118.53, 115.31, 112.89, 109.18, 77.29, 77.03, 76.78, 75.05, 68.41, 67.33, 50.38, 47.30, 25.90. DART-HRMS: m/z calcd. for $C_{27}H_{27}C_{12}N_3O_5$ [MH]$^+$, 544.1406; Found: 544.1409. IR (solid) vmax: 2922, 2850, 1596, 1555, 1509, 1450, 1375, 1321, 1228, 1195, 1151, 1036, 944, 827, 753. Purity, Method B: 95.1%

4-(4-(4-((2R,4R)-2-(2,4-dichlorophenyl)-2-methyl-1,3-dioxolan-4-yl)methoxy)phenyl)piperazin-1-yl)aniline (8). 10% palladium on carbon (24.4 mg, 5% mole ratio) was added to a dry round bottom flask. Ethanol (100 mL) was added followed by slow addition of 6 (250 mg, 0.459 mmol). Hydrazine monohydrate (0.14 mL, 4.59 mmol) was added dropwise and the mixture was stirred at reflux for 2 h. Upon cooling to RT, the mixture was filtered through celite. The celite was washed with ethanol (500 mL) to ensure complete elution of the aniline. The filtrate was concentrated to afford a yellow solid, which was recrystallized in EtOH to afford 8 (100 mg, 42%). $^1$H NMR (500 MHz, $CDCl_3$) δ 8.20 (d, 1H), 7.66 (d, 1H), 7.46 (t, 1H), 7.06-6.85 (m, 6H), 6.72 (d, 1H), 4.37 (s, 1H), 4.16 (m, 1H), 4.13-3.94 (m, 2H), 3.94-3.82 (m, 1H), 3.63 (t, 2H), 3.50 (s, 1H), 3.35-3.16 (m, 6H), 1.86 (s, 3H). $^{13}$C NMR (126 MHz, $CDCl_3$) δ 131.20, 128.91, 126.79, 125.99, 118.85, 118.59, 118.25, 116.23, 115.56, 115.46, 112.90, 77.28, 77.03, 76.78, 73.97, 69.29, 67.04, 51.25, 50.86, 50.39, 47.31, 25.74, 0.02. DART-HRMS: m/z calcd. for $C_{27}H_{29}C_{12}N_3O_3$ [MH]$^+$, 514.1664; Found: 514.1648. IR (solid) vmax: 2919, 2850, 1595, 1560, 1510, 1464, 1450, 1375, 1228, 1196, 1150, 1037, 877, 825, 754. Purity, Method A: 98.0%.

4-(4-(4-(((2S,4R)-2-(2,4-dichlorophenyl)-2-methyl-1,3-dioxolan-4-yl)methoxy)phenyl)piperazin-1-yl)aniline (9). 10% palladium on carbon (10 mg, 5% mole ratio) was added to a dry round bottom flask. Ethanol (50 mL) was added followed by slow addition of 8 (100 mg, 0.184 mmol). Hydrazine monohydrate (0.06 mL, 1.84 mmol) was added dropwise and the mixture was stirred at reflux for 2 h. Upon cooling to RT, the mixture was filtered through celite. The celite was washed with ethanol (300 mL) to ensure complete elution of the aniline. The filtrate was concentrated to afford a yellow solid, which was recrystallized in EtOH to afford 9 (89 mg, 94%). $^1$H NMR (500 MHz, CDCl$_3$) δ 8.20 (d, 1H), 7.68 (d, 1H), 7.43 (s, 1H), 7.24 (d, 1H), 6.92 (m, 3H), 6.81-6.68 (m, 3H), 4.70-4.59 (m, 1H), 4.35 (m, 1H), 4.00 (d, 1H), 3.78 (m, 2H), 3.61 (m, 1H), 3.49 (s, 1H), 3.25 (m, 5H). $^{13}$C NMR (126 MHz, CDCl$_3$) δ 130.97, 128.59, 126.70, 125.99, 118.85, 118.54, 118.21, 116.24, 115.21, 112.90, 77.28, 77.03, 76.78, 75.07, 68.43, 67.40, 51.24, 50.85, 50.38, 47.30, 25.90. DART-HRMS: m/z calcd. for $C_{27}H_{29}C_{12}N_3O_3$ [MH]$^+$, 514.1664; Found: 514.1666. IR (solid) vmax: 2921, 2823, 1590, 1510, 1450, 1375, 1321, 1227, 1193, 1149, 1037, 944, 824, 753. Purity, Method B: 95.2%

General Amide Coupling Procedures. Method A. Aniline 8 or 9 (20 mg, 0.039 mmol), carboxylic acid (0.117 mmol), EDCI (0.117 mmol), and DMAP (0.117 mmol) were dissolved in anhydrous DCM (10 mL) and stirred under argon for 12 h at room temperature. The crude reaction was immediately purified via column chromatography (SiO$_2$, 0-80% acetone in hexanes) to afford the ITZ amide analogue.

Method B. Acid (0.038 mmol) and HATU (0.083 mmol) were added to a round bottom flask. Anhydrous DMF was added (5 mL) followed by NMM (0.15 mmol); and this mixture was stirred at room temperature for 30 mins. Aniline 8 or 9 (20 mg, 0.038 mmol) in anhydrous DMF (4 mL) was added to the mixture and stirred for 12 h at room temperature. The solution was added to ice cold water and washed with EtOAc (3×20 mL). The organic layers were combined and washed with H$_2$O (2×20 mL) and brine (1×20 mL). The organic layers were dried over Na$_2$SO$_4$ and evaporated to dryness. Crude products was purified via preparative thin layer chromatography (Analtech Uniplate 20×20 cm 2000 micron, 3% acetone in hexanes) or column chromatography (SiO$_2$, 0-80% acetone in hexanes) to afford the ITZ amide analogue.

N-(4-(4-(4-(((2R,4R)-2-(2,4-dichlorophenyl)-2-methyl-1,3-dioxolan-4-yl)methoxy)phenyl)piperazin-1-yl)phenyl) benzamide (10). Amide coupling method A; Yield=13.0 mg, 54%. $^1$H NMR (500 MHz, CDCl$_3$) δ 7.92 (d, 2H), 7.73 (s, 1H), 7.66 (d, 1H), 7.59 (m, 2H), 7.54 (t, 2H), 7.46 (d, 1H), 7.28 (m, 1H), 7.05 (d, 2H), 7.02-6.97 (m, 2H), 6.94 (d, 2H), 4.37 (m, 1H), 4.17 (m, 1H), 4.09-3.98 (m, 2H), 3.89 (t, 1H), 3.38 (m, 4H), 3.29 (m, 4H), 1.86 (s, 3H). $^{13}$C NMR (126 MHz, CDCl$_3$) δ 165.48, 152.92, 148.50, 146.09, 138.15, 135.17, 134.56, 132.83, 131.69, 131.19, 130.61, 128.91, 128.78, 126.95, 126.79, 121.64, 118.40, 116.95, 115.48, 110.66, 109.09, 77.27, 77.23, 77.02, 76.76, 73.96, 69.29, 67.03, 50.74, 49.88, 29.72, 25.74. DART-HRMS: m/z calcd. for $C_{34}H_{33}C_{12}N_3O_4$ [MH]$^+$, 618.1926; Found: 618.1919. IR (solid) vmax: 3367, 3333, 2958, 2924, 2853, 1693, 1638, 1547, 1511, 1450, 1375, 1248, 1230, 1194, 1157, 1037, 941, 822, 703. Purity, Method A: 96.2%

N-(4-(4-(4-(((2R,4R)-2-(2,4-dichlorophenyl)-2-methyl-1,3-dioxolan-4-yl)methoxy)phenyl)piperazin-1-yl)phenyl)-2-naphthamide (11). Amide coupling method A; Yield=6.0 mg, 23%. $^1$H NMR (500 MHz, CDCl$_3$) δ 8.39 (d, 1H), 7.97 (d, 1H), 7.93-7.85 (m, 1H), 7.75 (d, 1H), 7.66-7.48 (m, 7H), 7.41 (d, 1H), 7.24 (m, 1H), 7.03 (d, 2H), 6.96 (d, 2H), 6.90 (d, 2H), 4.33 (m, 1H), 4.12 (m, 1H), 4.05-3.93 (m, 2H), 3.85 (m, 1H), 3.38-3.30 (m, 5H), 3.26 (m, 5H), 1.82 (s, 3H). $^{13}$C NMR (126 MHz, CDCl$_3$) δ 167.31, 152.94, 148.59, 146.09, 138.15, 134.75, 134.56, 133.81, 132.84, 131.20, 130.94, 130.75, 130.17, 128.91, 128.43, 127.33, 126.79, 126.59, 125.38, 125.02, 124.79, 121.41, 118.41, 117.01, 115.92, 115.49, 111.61, 109.09, 106.00, 101.89, 97.74, 77.28, 77.22, 77.02, 76.77, 73.96, 69.29, 67.03, 50.74, 49.92, 29.72, 25.74, 0.02. DART-HRMS: m/z calcd. for $C_{38}H_{35}C_{12}N_3O_4$ [MH]$^+$, 668.2083; Found: 668.2075. IR (solid) vmax: 3294, 3247, 3042, 2985, 2873, 1639, 1586, 1509, 1450, 1373, 1226, 1192, 1146, 1035, 942, 821, 733. Purity, Method A: 97.0%.

N-(4-(4-(4-(((2R,4R)-2-(2,4-dichlorophenyl)-2-methyl-1,3-dioxolan-4-yl)methoxy)phenyl)piperazin-1-yl)phenyl)picolinamide (12). Amide coupling method A; Yield=9.0 mg, 37%. $^1$H NMR (500 MHz, CDCl$_3$) δ 9.96 (s, 1H), 8.69-8.62 (m, 1H), 8.35 (d, 1H), 7.95 (m, 1H), 7.76 (d, 1H), 7.66 (d, 1H), 7.55-7.48 (m, 1H), 7.46 (d, 1H), 7.28 (m, 1H), 7.06 (d, 2H), 7.00 (d, 2H), 6.94 (d, 2H), 4.37 (s, 1H), 4.17 (m, 1H), 4.09-3.97 (m, 2H), 3.89 (m, 1H), 3.38 (m, 4H), 3.33-3.25 (m, 4H), 1.86 (s, 3H). $^{13}$C NMR (126 MHz, CDCl$_3$) δ 161.67, 152.90, 150.10, 148.20, 147.94, 146.11, 138.16, 137.64, 134.56, 132.84, 131.20, 130.66, 128.91, 126.79, 126.26, 122.32, 120.91, 118.38, 116.97, 115.48, 111.61, 109.09, 106.05, 102.12, 77.28, 77.23, 77.03, 76.77, 73.97, 69.30, 67.04, 50.75, 49.91, 25.74. DART-HRMS: m/z calcd. for $C_{33}H_{32}C_{12}N_4O_4$ [MH]$^+$, 619.1879; Found: 619.1872. IR (solid) vmax: 3367, 2923, 2851, 1672, 1585, 1552, 1509, 1454, 1385, 1268, 1227, 1192, 1148, 1020, 940, 912, 814, 747, 620. Purity, Method A: 96.9%.

N-(4-(4-(4-(((2R,4R)-2-(2,4-dichlorophenyl)-2-methyl-1,3-dioxolan-4-yl)methoxy)phenyl)piperazin-1-yl)phenyl) nicotinamide (13). Amide coupling method A; Yield=6.2 mg, 25%. $^1$H NMR (500 MHz, CDCl$_3$) δ 9.14 (s, 1H), 8.83 (s, 1H), 8.26 (d, 1H), 7.72 (s, 1H), 7.66 (d, 1H), 7.59 (d, 2H), 7.49 (d, 1H), 7.46 (d, 1H), 7.28 (m, 1H), 7.05 (d, 2H), 7.00 (d, 2H), 6.96-6.90 (m, 2H), 4.37 (m, 1H), 4.17 (m, 1H), 4.10-3.94 (m, 2H), 3.89 (m, 1H), 3.44-3.33 (m, 4H), 3.33-3.20 (m, 4H), 1.86 (s, 3H). $^{13}$C NMR (126 MHz, CDCl$_3$) δ 131.20, 128.91, 126.80, 121.87, 118.43, 116.86, 115.49, 111.26, 109.10, 105.77, 101.72, 77.28, 77.23, 77.03, 76.77, 73.96, 69.29, 67.03, 50.73, 49.72, 25.74. DART-HRMS: m/z calcd. for $C_{33}H_{32}C_{12}N_4O_4$ [MH]$^+$, 619.1879; Found: 619.1876. IR (solid) vmax: 3639, 3570, 2920, 2824, 1644, 1509, 1447, 1374, 1227, 1194, 1150, 1037, 941, 828, 733, 534. Purity, Method A: 96.9%.

N-(4-(4-(4-(((2R,4R)-2-(2,4-dichlorophenyl)-2-methyl-1,3-dioxolan-4-yl)methoxy)phenyl)piperazin-1-yl)phenyl) isonicotinamide (14). Amide coupling method A; Yield=12.0 mg, 49%. 41 NMR (500 MHz, CDCl$_3$) δ 8.85 (d, 2H), 7.75 (d, 3H), 7.66 (d, 1H), 7.60 (d, 2H), 7.05 (d, 2H), 7.00 (d, 2H), 6.94 (d, 2H), 4.17 (m, 1H), 4.09-3.95 (m, 2H), 3.44-3.33 (m, 4H), 3.33-3.24 (m, 4H). $^{13}$C NMR (126 MHz, Chloroform-d) δ 150.79, 131.19, 126.79, 121.81, 120.79, 118.43, 116.79, 115.50, 115.25, 110.09, 104.91, 77.22, 73.96, 69.30, 67.02, 50.72, 49.66, 25.73. DART-HRMS: m/z calcd. for $C_{33}H_{32}C_{12}N_4O_4$ [MH]$^+$, 619.1879; Found: 619.1871. IR (solid) vmax: 3302, 3290, 2950, 2936, 1662, 1587, 1512, 1458, 1377, 1249, 1225, 1194, 1151, 1035 943, 823, 690. Purity, Method A: 94.1%

N-(4-(4-(4-(((2S,4R)-2-(2,4-dichlorophenyl)-2-methyl-1,3-dioxolan-4-yl)methoxy)phenyl)piperazin-1-yl)phenyl)benzamide (15). Amide coupling method A; Yield=5.0 mg, 20.6%. $^1$H NMR (500 MHz, CDCl$_3$) δ 7.91 (d, 2H), 7.73 (s, 1H), 7.69 (d, 1H), 7.59 (m, 2H), 7.54 (t, 2H), 7.04 (d, 2H), 6.95 (d, 2H), 6.78 (d, 2H), 4.65 (m, 1H), 4.35 (m, 1H), 4.00 (m, 1H), 3.82-3.74 (m, 2H), 3.36 (d, 3H), 3.28 (d, 4H), 1.83 (s, 3H). $^{13}$C NMR (126 MHz, CDCl$_3$) δ 131.68, 130.97, 128.78, 128.58, 126.95, 126.70, 121.64, 118.35, 116.95, 115.24, 112.04, 109.16, 106.31, 77.27, 77.22, 77.02, 76.77, 75.07, 68.44, 67.39, 50.73, 49.88, 25.90. DART-HRMS: m/z calcd. for C$_{34}$H$_{33}$C$_{12}$N$_3$O$_4$ [MH]$^+$, 618.1926; Found: 618.1916. IR (solid) vmax: 3305, 2964, 2824, 1637, 1592, 1511, 1448, 1374, 1226, 1192, 1152, 1034, 943, 818, 728, 703. Purity, Method B: 95.6%.

N-(4-(4-(4-(((2S,4R)-2-(2,4-dichlorophenyl)-2-methyl-1,3-dioxolan-4-yl)methoxy)phenyl)piperazin-1-yl)phenyl)-2-naphthamide (16). Amide coupling method A; Yield=3.0 mg, 11.5%. $^1$H NMR (500 MHz, CDCl$_3$) δ 8.43 (s, 1H), 8.08-7.92 (m, 4H), 7.89 (s, 1H), 7.73-7.58 (m, 5H), 7.06 (d, 2H), 6.96 (d, 2H), 6.78 (d, 2H), 4.65 (m, 1H), 4.35 (m, 1H), 4.00 (m, 2H), 3.86-3.71 (m, 2H), 3.45-3.33 (m, 4H), 3.33-3.21 (m, 4H), 1.83 (s, 3H). $^{13}$C NMR (126 MHz, CDCl$_3$) δ 165.53, 152.75, 148.50, 146.03, 139.34, 134.83, 134.36, 132.80, 132.69, 132.36, 130.97, 130.68, 128.96, 128.73, 128.59, 127.83, 127.41, 126.94, 126.71, 123.57, 121.69, 118.36, 116.96, 115.63, 115.24, 111.68, 109.16, 105.89, 77.27, 77.22, 77.02, 76.77, 75.07, 68.44, 67.40, 50.74, 49.87, 25.91, 1.04. DART-HRMS: m/z calcd. for C$_{38}$H$_{35}$C$_{12}$N$_3$O$_4$ [MH]$^+$, 668.2083; Found: 668.2116. IR (solid) vmax: 3326, 2920, 2851, 1663, 1596, 1558, 1513, 1450, 1373, 1229, 1195, 1151, 1037, 948, 822, 760. Purity, Method A: 96.3%

N-(4-(4-(4-(((2S,4R)-2-(2,4-dichlorophenyl)-2-methyl-1,3-dioxolan-4-yl)methoxy)phenyl)piperazin-1-yl)phenyl)picolinamide (17). Amide coupling method A; Yield=9.0 mg, 37%. $^1$H NMR (500 MHz, CDCl$_3$) δ 9.96 (s, 1H), 8.71-8.60 (m, 1H), 8.34 (m, 1H), 7.95 (m, 1H), 7.76 (m, 2H), 7.69 (d, 1H), 7.57-7.48 (m, 1H), 7.25 (m, 1H), 7.06 (d, 2H), 6.96 (d, 2H), 6.78 (d, 2H), 4.65 (m, 1H), 4.35 (m, 1H), 4.00 (m, 1H), 3.83-3.74 (m, 2H), 3.37 (s, 5H), 3.28 (s, 4H), 1.83 (s, 3H). $^{13}$C NMR (126 MHz, CDCl$_3$) δ 147.93, 137.64, 130.97, 128.58, 126.71, 122.31, 120.91, 118.33, 116.96, 115.25, 111.75, 77.28, 77.02, 76.77, 75.06, 68.44, 67.39, 50.74, 49.90, 25.91. DART-HRMS: m/z calcd. for C$_{33}$H$_{32}$C$_{12}$N$_4$O$_4$ [MH]$^+$, 619.1879; Found: 619.1862. IR (solid) vmax: 3365, 2955, 2849, 1675, 1586, 1568, 1510, 1453, 1373, 1268, 1229, 1193, 1151, 1097, 1037, 942, 823, 747. Purity, Method B: 92.7%

N-(4-(4-(4-(((2S,4R)-2-(2,4-dichlorophenyl)-2-methyl-1,3-dioxolan-4-yl)methoxy)phenyl)piperazin-1-yl)phenyl)nicotinamide (18). Amide coupling method A; Yield=6.0 mg, 24.7%. $^1$H NMR (500 MHz, CDCl$_3$) δ 9.15 (s, 1H), 8.83 (s, 1H), 8.26 (d, 1H), 7.86 (s, 1H), 7.68 (d, 1H), 7.60 (d, 2H), 7.49 (s, 1H), 7.43 (d, 1H), 7.28-7.20 (m, 1H), 7.01 (m, 4H), 6.83-6.73 (m, 2H), 4.65 (m, 1H), 4.35 (m, 1H), 4.00 (m, 1H), 3.83-3.74 (m, 2H), 3.44-3.34 (m, 4H), 3.29 (t, 4H), 1.83 (s, 3H). $^{13}$C NMR (126 MHz, CDCl$_3$) δ 139.33, 134.36, 132.80, 130.97, 128.58, 126.71, 121.92, 118.54, 116.92, 115.27, 109.17, 77.29, 77.24, 77.03, 76.78, 75.05, 68.43, 67.36, 50.88, 49.67, 25.90. DART-HRMS: m/z calcd. for C$_{33}$H$_{32}$C$_{12}$N$_4$O$_4$ [MH]$^+$, 619.1879; Found: 619.1866. IR (solid) vmax: 3364, 3315, 2960, 2924, 2853, 1673, 1511, 1456, 1372, 1259, 1227, 1193, 1097, 1035, 826, 807. Purity, Method A: 96.5%

N-(4-(4-(4-(((2S,4R)-2-(2,4-dichlorophenyl)-2-methyl-1,3-dioxolan-4-yl)methoxy)phenyl)piperazin-1-yl)phenyl)isonicotinamide (19). Amide coupling method A; Yield=8.0 mg, 33%. 41 NMR (500 MHz, CDCl$_3$) δ 8.85 (s, 2H), 7.82-7.70 (m, 3H), 7.68 (d, 1H), 7.59 (d, 2H), 7.43 (d, 1H), 7.24 (m, 1H), 7.04 (d, 2H), 7.01-6.88 (m, 2H), 6.82-6.72 (m, 2H), 4.66 (m, 1H), 4.35 (m, 1H), 4.00 (m, 1H), 3.85-3.71 (m, 2H), 3.38 (m, 4H), 3.27 (m, 4H), 1.86 (s, 3H). $^{13}$C NMR (126 MHz, CDCl$_3$) δ 152.80, 150.80, 145.98, 139.36, 134.36, 132.81, 130.97, 128.58, 126.70, 121.81, 120.80, 118.38, 116.79, 115.27, 111.58, 109.16, 77.27, 77.22, 77.02, 76.77, 75.07, 68.46, 67.39, 50.71, 49.65, 29.72, 25.90, 1.03. DART-HRMS: m/z calcd. for C$_{33}$H$_{32}$C$_{12}$N$_4$O$_4$ [MH]$^+$, 619.1879; Found: 619.1866. IR (solid) vmax: 3256, 2963, 2854, 1660, 1587, 1510, 1449, 1376, 1261, 1226, 1193, 1150, 1034, 940, 826, 740. Purity, Method A: 95.1%

N-(4-(4-(4-(((2R,4R)-2-(2,4-dichlorophenyl)-2-methyl-1,3-dioxolan-4-yl)methoxy)phenyl)piperazin-1-yl)phenyl)-2-hydroxybenzamide (26). Amide coupling method B; Yield=10.0 mg, 16%. $^1$H NMR (500 MHz, CDCl$_3$) δ 7.87 (s, 1H), 7.58-7.42 (m, 5H), 7.28 (m, 1H), 7.07 (m, 3H), 7.02-6.91 (m, 5H), 4.37 (m, 1H), 4.17 (m, 1H), 4.09-3.98 (m, 2H), 3.93-3.85 (m, 1H), 3.44-3.35 (m, 4H), 3.29 (t, 4H), 1.86 (s, 2H). $^{13}$C NMR (126 MHz, CDCl$_3$) δ 134.52, 131.20, 128.91, 126.79, 125.25, 122.85, 118.97, 118.43, 116.79, 115.49, 73.96, 69.29, 67.03, 50.72, 49.65. DART-HRMS: m/z calcd. for C$_{34}$H$_{33}$C$_{12}$N$_3$O$_5$ [MH]$^+$, 634.1865; Found: 634.1875. IR (solid) vmax: 3310, 2956, 2916, 2848, 1646, 1596, 1511, 1453, 1373, 1250, 1228, 1196, 1152, 1036, 942, 821, 755. Purity, Method B: 98.1%

N-(4-(4-(4-(((2R,4R)-2-(2,4-dichlorophenyl)-2-methyl-1,3-dioxolan-4-yl)methoxy)phenyl)piperazin-1-yl)phenyl)-3-hydroxybenzamide (27). Amide coupling method B; Yield=6.0 mg, 25%. $^1$H NMR (500 MHz, CDCl$_3$) δ 7.74 (d, 4H), 7.63-7.48 (m, 6H), 7.48-7.37 (m, 6H), 7.17-6.84 (m, 8H), 5.21 (s, 1H), 4.37 (s, 1H), 4.16 (m, 1H), 4.12-3.95 (m, 2H), 3.37 (d, 4H), 3.29 (t, 4H), 1.88 (m, 2H). $^{13}$C NMR (126 MHz, CDCl$_3$) δ 131.20, 130.08, 126.79, 125.30, 121.68, 118.41, 116.94, 115.49, 114.42, 69.29, 67.03, 50.73, 49.84, 25.73. DART-HRMS: m/z calcd. for C$_{34}$H$_{33}$C$_{12}$N$_3$O$_5$ [MH]$^+$, 634.1876; Found: 634.1847. IR (solid) vmax: 3311, 2967, 2926, 2877, 1736, 1644, 1586, 1513, 1449, 1375, 1230, 1198, 1038, 945, 825, 746. Purity, Method A: 97.8%.

N-(4-(4-(4-(((2R,4R)-2-(2,4-dichlorophenyl)-2-methyl-1,3-dioxolan-4-yl)methoxy)phenyl)piperazin-1-yl)phenyl)-4-hydroxybenzamide (28). Amide coupling method B; Yield=5.0 mg, 8%. $^1$H NMR (500 MHz, CDCl$_3$) δ 7.84 (d, J=8.3 Hz, 1H), 7.66 (d, J=8.3 Hz, 1H), 7.57 (d, J=8.5 Hz, 2H), 7.04 (d, J=8.9 Hz, 2H), 7.00 (d, J=9.0 Hz, 2H), 6.98-6.91 (m, 3H), 4.42-4.31 (m, 1H), 4.16 (dd, J=9.4, 5.1 Hz, 1H), 4.10-3.96 (m, 2H), 3.89 (t, J=7.7 Hz, 1H), 3.44-3.32 (m, 4H), 3.32-3.21 (m, 4H), 2.05 (s, 3H). $^{13}$C NMR (126 MHz, CDCl$_3$) δ 152.99, 138.03, 134.54, 131.14, 129.02, 126.78, 118.50, 117.00, 115.46, 109.54, 69.24, 66.91, 50.79, 49.94, 49.17, 30.85, 25.62. DART-HRMS: m/z calcd. for C$_{34}$H$_{33}$C$_{12}$N$_3$O$_5$ [MH]$^+$, 634.1865; Found: 634.1779. IR (solid) vmax: 3288, 2918, 2828, 1627, 1515, 1375, 1230, 1038, 944, 824, 762, 527. Purity, Method A: 99.9%.

N-(4-(4-(4-(((2S,4R)-2-(2,4-dichlorophenyl)-2-methyl-1,3-dioxolan-4-yl)methoxy)phenyl)piperazin-1-yl)phenyl)-2-hydroxybenzamide (29). Amide coupling method B; Yield=7.4 mg, 30%. $^1$H NMR (500 MHz, Chloroform-d) δ 12.14 (s, 1H), 7.87 (s, 1H), 7.69-7.68 (d, J=8.4 Hz, 1H), 7.54-7.47 (s, 3H), 7.43 (s, 1H), 7.25-7.24 (d, J=8.4 Hz, 1H), 7.09-7.04 (m, 3H), 6.97-6.94 (m, 3H), 6.79-6.77 (d, J=8.7 Hz, 2H), 4.68-4.63 (m, 1H), 4.37-4.34 (m, 1H), 4.01-3.98 (m, 1H), 3.80-3.77 (m, 2H), 3.55-3.50 (m, 1H), 3.38-3.27 (m, 8H), 1.83 (s, 3H). $^{13}$C NMR (126 MHz, CDCl$_3$) δ

168.27, 161.99, 152.80, 146.03, 139.36, 134.52, 130.98, 128.59, 126.71, 125.26, 122.86, 118.98, 118.86, 118.39, 116.79, 115.26, 109.17, 75.07, 68.45, 67.39, 50.70, 49.63, 25.90. DART-HRMS: m/z calcd. for $C_{34}H_{33}C_{12}N_3O_5$ [MH]$^+$, 634.1876; Found: 634.1843. IR (solid) vmax: 2924, 2852, 1598, 1511, 1452, 1228, 1191, 1036, 824, 756. Purity, Method A: 99.3%.

N-(4-(4-(4-(((2S,4R)-2-(2,4-dichlorophenyl)-2-methyl-1,3-dioxolan-4-yl)methoxy)phenyl)piperazin-1-yl)phenyl)-3-hydroxybenzamide (30). Amide coupling A; Yield=8 mg, 45.5%. $^1$H NMR (500 MHz, CDCl$_3$) δ 7.70 (s, 1H), 7.64 (d, 1H), 7.52 (d, 2H), 7.46 (s, 1H), 7.38 (s, 1H), 7.34 (s, 2H), 7.24-7.17 (m, 1H), 7.04-6.96 (m, 3H), 6.90 (d, 2H), 6.73 (d, 2H), 5.72 (s, 1H), 4.65-4.56 (m, 1H), 4.31 (t, 1H), 3.95 (m, 1H), 3.74 (t, 2H), 3.31 (d, 4H), 3.23 (d, 4H), 1.80 (d, 3H). $^{13}$C NMR (126 MHz, CDCl$_3$) δ 130.05, 128.58, 126.71, 121.75, 118.47, 118.36, 116.92, 115.25, 114.62, 111.69, 106.06, 102.05, 77.22, 75.07, 67.39, 50.71, 49.81, 25.90. DART-HRMS: m/z calcd. for $C_{34}H_{33}C_{12}N_3O_5$ [MH]$^+$, 634.1876; Found: 634.1884. IR (solid) vmax: 3279, 2925, 2852, 2824, 1639, 1590, 1446, 1409, 1373, 1228, 1190, 115, 1036, 944, 826, 747. Purity, Method A: 96.2%.

N-(4-(4-(4-(((2S,4R)-2-(2,4-dichlorophenyl)-2-methyl-1,3-dioxolan-4-yl)methoxy)phenyl)piperazin-1-yl)phenyl)-4-hydroxybenzamide (31). Amide coupling method B; Yield=7.7 mg, 31% 41 NMR (500 MHz, Chloroform-d): 7.83-7.82 (d, J=7.6 Hz, 1H), 7.69-7.68 (d, J=5.9 Hz, 1H), 7.57-7.55 (d, J=8.2 Hz, 1H), 7.43 (s, 1H), 7.25-7.23 (d, J=8.6 Hz, 1H), 7.03-7.02 (d, J=8.0 Hz, 2H), 6.94 (m, 3H), 6.79-6.77 (d, J=7.9 Hz, 1H), 4.66-4.64 (t, 1H), 4.37-3.43 (t, J=7.5 Hz, 1H), 4.01-3.98 (m, 1H), 3.79-3.76 (t, J=7.6 Hz, 1H), 3.36-3.27 (m, 8H), 1.83 (s, 3H); 6 $^{13}$C NMR (126 MHz, CDCl$_3$): 165.16, 158.80, 152.84, 148.46, 146.02, 139.35, 134.37, 132.81, 130.98, 129.08, 128.59, 126.71, 121.74, 118.38, 116.98, 115.55, 115.26, 109.16, 77.27, 77.02, 76.77, 75.07, 68.44, 67.39, 50.74, 49.89, 25.90; DART-HRMS: m/z calcd. for $C_{34}H_{33}C_{12}N_3O_5$ [MH]$^+$, 634.1876; Found: 634.1843. IR (solid) vmax: 3068, 2927, 2853, 1729, 1607, 1511, 1230, 1099, 824. Purity, Method A: 95.7%.

3-chloro-N-(4-(4-(4-(((2S,4R)-2-(2,4-dichlorophenyl)-2-methyl-1,3-dioxolan-4-yl)methoxy)phenyl)piperazin-1-yl)phenyl)benzamide (32). Amide coupling method A; Yield=6.0 mg, 24%. $^1$H NMR (500 MHz, CDCl$_3$) δ 7.90 (t, 1H), 7.78 (d, 1H), 7.68 (d, 2H), 7.60-7.54 (m, 3H), 7.47 (t, 1H), 7.43 (d, 1H), 7.24 (m, 1H), 7.04 (d, 2H), 6.98-6.92 (m, 2H), 6.81-6.75 (m, 2H), 4.65 (m, 1H), 4.35 (m, 1H), 4.00 (m, 1H), 3.82-3.73 (m, 2H), 3.41-3.32 (m, 4H), 3.27 (m, 4H), 1.83 (s, 3H). $^{13}$C NMR (126 MHz, CDCl$_3$) δ 130.97, 130.10, 128.58, 127.34, 126.71, 121.74, 118.36, 116.88, 115.24, 111.47, 109.16, 105.92, 101.77, 77.27, 77.02, 76.76, 75.06, 68.44, 67.39, 50.72, 49.77, 25.90. DART-HRMS: m/z calcd. for $C_{34}H_{32}C_{13}N_3O_4$ [MH]$^+$, 648.2032; Found: 648.1998. IR (solid) vmax: 3311, 3283, 3254, 2961, 2854, 1640, 1588, 1512, 1451, 1375, 1228, 1192, 1152, 1037, 943, 820, 755. Purity, Method A: 99.8%.

N-(4-(4-(4-(((2S,4R)-2-(2,4-dichlorophenyl)-2-methyl-1,3-dioxolan-4-yl)methoxy)phenyl)piperazin-1-yl)phenyl)-3-methoxybenzamide (33). Amide coupling method A; Yield=4.0 mg, 16%. $^1$H NMR (500 MHz, CDCl$_3$) δ 7.74 (s, 1H), 7.68 (d, 1H), 7.59 (d, 2H), 7.51-7.46 (m, 1H), 7.45-7.41 (m, 3H), 7.24 (m, 1H), 7.14-7.08 (m, 1H), 7.04 (d, 2H), 6.95 (d, 2H), 6.81-6.75 (m, 2H), 4.65 (m, 1H), 4.35 (m, 1H), 4.00 (m, 1H), 3.92 (s, 3H), 3.81-3.74 (m, 2H), 3.42-3.31 (m, 5H), 3.27 (t, 4H), 1.83 (s, 3H). $^{13}$C NMR (126 MHz, CDCl$_3$) δ 129.75, 121.58, 118.35, 115.35, 116.93, 116.93, 115.24, 110.72, 109.81, 104.93, 100.60, 96.72, 77.21, 55.52, 50.72, 49.86. DART-HRMS: m/z calcd. for $C_{35}H_{35}C_{12}N_3O_5$ [MH]$^+$, 652.1537; Found: 652.1532. IR (solid) vmax: 3289, 2922, 2823, 138, 1580, 1510, 1450, 1374, 1288, 1190, 1150, 1033, 943, 817, 746, 686, 524. Purity, Method A: 94.8%.

3-acetyl-N-(4-(4-(4-(((2S,4R)-2-(2,4-dichlorophenyl)-2-methyl-1,3-dioxolan-4-yl)methoxy)phenyl)piperazin-1-yl)phenyl)benzamide (34). Amide coupling method A; Yield=3.4 mg, 26%. $^1$H NMR (500 MHz, CDCl$_3$) δ 8.47 (t, J=1.7 Hz, 1H), 8.16 (dd, J=7.7, 1.7 Hz, 2H), 7.88 (s, 1H), 7.71-7.58 (m, 4H), 7.24 (dd, J=8.5, 2.2 Hz, 1H), 7.08-7.01 (m, 2H), 7.00-6.91 (m, 2H), 6.82-6.74 (m, 2H), 4.65 (p, J=6.1 Hz, 1H), 4.35 (dd, J=8.6, 6.4 Hz, 1H), 4.00 (dd, J=9.7, 5.2 Hz, 1H), 3.84-3.72 (m, 2H), 3.37 (dd, J=6.4, 3.6 Hz, 4H), 3.27 (dd, J=6.4, 3.6 Hz, 4H), 2.72 (s, 3H), 1.83 (s, 3H). $^{13}$C NMR (126 MHz, CDCl$_3$) δ 197.40, 152.76, 148.66, 139.35, 135.62, 134.35, 132.80, 131.75, 131.37, 130.97, 129.26, 128.59, 126.71, 126.30, 121.80, 118.36, 116.86, 115.24, 109.16, 75.07, 68.44, 67.39, 50.72, 49.76, 26.78, 25.90, 1.04. DART-HRMS: m/z calcd. for $C_{36}H_{35}C_{12}N_3O_5$ [MH]$^+$, 660.2021; Found: 660.1904; IR (solid) vmax: 3295, 2928, 2827, 1685, 1511, 1229, 1037, 823. Purity, Method B: 97.2%

N-(4-(4-(4-(((2S,4R)-2-(2,4-dichlorophenyl)-2-methyl-1,3-dioxolan-4-yl)methoxy)phenyl)piperazin-1-yl)phenyl)furan-3-carboxamide (35). Amide coupling method A; Yield=2.0 mg, 8%. $^1$H NMR (500 MHz, CDCl$_3$) δ 8.06 (s, 1H), 7.68 (d, J=8.5 Hz, 1H), 7.53 (d, J=7.8 Hz, 3H), 7.36 (s, 1H), 7.24 (dd, J=8.5, 2.1 Hz, 1H), 7.05-6.98 (m, 2H), 6.99-6.91 (m, 2H), 6.82-6.71 (m, 3H), 4.65 (p, J=6.0 Hz, 1H), 4.35 (dd, J=8.6, 6.4 Hz, 1H), 4.00 (dd, J=9.7, 5.4 Hz, 1H), 3.82-3.73 (m, 2H), 3.36 (dd, J=6.6, 3.5 Hz, 4H), 3.27 (dd, J=6.4, 3.5 Hz, 4H), 1.83 (s, 3H). $^{13}$C NMR (126 MHz, CDCl$_3$) δ 152.75, 143.99, 139.34, 130.97, 128.58, 126.71, 118.35, 116.89, 115.24, 109.16, 68.44, 67.39, 49.81, 29.72, 25.90. DART-HRMS m/z calcd. for $C_{32}H_{31}C_{12}N_3O_5$ [MH]$^+$, 608.1719; Found: 608.1701. IR (solid) vmax: 3313, 2918, 2849, 1636, 1512, 1375, 1233, 1155, 1037, 873, 821, 752, 601. Purity, Method B: 95.6%

N-(4-(4-(4-(((2S,4R)-2-(2,4-dichlorophenyl)-2-methyl-1,3-dioxolan-4-yl)methoxy)phenyl)piperazin-1-yl)phenyl)thiophene-3-carboxamide (36). Amide coupling method A; Yield=3.0 mg, 13%. 41 NMR (500 MHz, CDCl$_3$) δ 7.99 (d, 1H), 7.68 (d, 1H), 7.59-7.49 (m, 4H), 7.44 (m, 2H), 7.24 (m, 1H), 7.03 (d, 2H), 6.95 (d, 2H), 6.78 (d, 2H), 4.65 (m, 1H), 4.35 (m, 1H), 4.00 (m, 1H), 3.78 (m, 2H), 3.41-3.32 (m, 4H), 3.27 (m, 4H). $^{13}$C NMR (126 MHz, CDCl$_3$) δ 152.75, 146.02, 139.34, 134.36, 130.97, 128.58, 128.36, 126.83, 126.70, 126.03, 121.67, 119.77, 118.35, 116.93, 115.88, 115.24, 111.51, 109.16, 105.96, 101.84, 97.85, 93.77, 77.27, 77.22, 77.01, 76.76, 75.07, 68.44, 67.39, 50.72, 49.84, 31.95, 30.18, 29.72, 29.38, 25.90, 22.71, 14.13, 1.04. DART-HRMS: m/z calcd. for $C_{32}H_{31}C_{12}N_3O_4S$ [MH]$^+$, 624.1491; Found: 624.1473. IR (solid) vmax: 2922, 2853, 1635, 1512, 1259, 1036, 818. Purity, Method A: 96.8% phenyl (4-(4-(4-(((2R,4R)-2-(2,4-dichlorophenyl)-2-methyl-1,3-dioxolan-4-yl)methoxy)phenyl)piperazin-1-yl)phenyl)carbamate (37). A solution of aniline 8 (500 mg) and pyridine (1.3 mL) in CHCl$_3$ (30 mL) was cooled to 0° C. Phenyl chloroformate (0.134 mL) was added dropwise and the mixture stirred at RT for 3 h. Water and petroleum ether (1:1) were added at which time an off-white precipitate formed. The solid was washed with H$_2$O and isopropyl alcohol to directly provide the trans-dioxolane carbamate 37. Yield=500 mg, 81%. 41 NMR (500 MHz, Chloroform-d) δ 7.67-7.65 (d, J=8.4 Hz, 1H), 7.45-7.42 (m, 4H), 7.29-7.23 (m, 3H), 7.02-6.98 (t, 4H), 6.94-6.92 (d, J=9.1 Hz, 2H), 4.38-4.36 (m, 1H), 4.18-4.15 (m, 1H), 4.07-3.83 (m, 2H), 3.91-3.83 (t, 1H), 3.83 (s, 1H), 3.35-3.34 (m, 4H), 3.29-3.28

(m, 4H), 1.86 (s, 3H). Found: 634.1779. $^{13}$C NMR (126 MHz, Chloroform-d) δ 152.93, 150.75, 146.09, 138.17, 134.57, 132.85, 131.21, 129.39, 128.92, 126.80, 125.60, 121.66, 120.35, 118.55, 118.39, 117.17, 115.50, 114.55, 110.01, 109.98, 109.10, 77.29, 77.03, 76.78, 73.97, 69.31, 67.03, 50.74, 49.98, 25.74. IR (solid) vmax: 3332, 3292, 2926, 2825, 1733, 1706, 1510, 1490, 1450, 1414, 1227, 1179, 1161, 1034, 943, 823, 747, 687. Xevo ESI-HRMS: m/z calcd. for $C_{34}H_{34}C_{12}N_3O_5$ [MH]$^+$, 633.1797; Found: 634.1865. Purity, Method A: 99.1%.

phenyl (4-(4-(4-(((2S,4R)-2-(2,4-dichlorophenyl)-2-methyl-1,3-dioxolan-4-yl)methoxy)phenyl)piperazin-1-yl)phenyl)carbamate (38). A solution of aniline 9 (500 mg) and pyridine (1.3 mL) in CHCl$_3$ (30 mL) was cooled to 0° C. Phenyl chloroformate (0.134 mL) was added dropwise and the mixture stirred at RT for 3 h. Water and petroleum ether (1:1) were added at which time an off-white precipitate formed. The solid was washed with H$_2$O and isopropyl alcohol to directly provide the cis-dioxolane carbamate 38. Yield=480 mg, 78%. 41 NMR (500 MHz, Chloroform-d) δ 7.69-7.68 (d, J=8.5 Hz, 1H), 7.45-7.42 (m, 5H), 7.31-7.23 (m, 4H), 7.02-7.00 (d, J=8.4 Hz, 2H), 6.96 (s, 2H), 6.79-6.77 (d, J=8.8 Hz, 2H), 4.68-4.63 (m, 1H), 4.36-4.34 (m, 1H), 4.01-3.98 (dd, J=9.6, 5.3 Hz, 1H), 3.80-3.77 (m, 2H), 3.35 (m, 4H), 3.28 (m, 4H), 1.86 (s, 1H), 1.83 (s, 2H). IR (solid) vmax: 3332, 2958, 2926, 2853, 1757, 1736, 1553, 1510, 1491, 1417, 1229, 1195, 1181, 1162, 1024, 911, 828, 751, 688. $^{13}$C NMR (126 MHz, Chloroform-d) δ 150.75, 139.36, 134.37, 132.81, 130.98, 129.39, 128.59, 126.71, 125.60, 121.66, 115.27, 109.17, 77.29, 77.03, 76.78, 75.06, 68.44, 67.38, 50.78, 49.94, 25.90. Xevo ESI-HRMS: m/z calcd. for $C_{34}H_{34}C_{12}N_3O_5$ [MH]$^+$, 633.1797; Found: 634.1866. Purity, Method A: 99.9%

N-(4-(4-(4-(((2R,4R)-2-(2,4-dichlorophenyl)-2-methyl-1,3-dioxolan-4-yl)methoxy)phenyl)piperazin-1-yl)phenyl)hydrazinecarboxamide (39). A solution of hydrazine hydrate (0.132 mL) and 37 (500 mg) in 1,4-dioxane (30 mL) was stirred at reflux for 3 h. After cooling to room temperature, the mixture was poured into H$_2$O (15 mL) and the resulting precipitate was filtered and washed with H$_2$O and isopropyl alcohol to directly provide the trans-dioxolane carboxamide 39. Yield=400 mg, 89%. $^1$H NMR (500 MHz, Chloroform-d) δ 8.07 (s, 1H), 7.67-7.65 (d, J=8.2 Hz, 1H), 7.52 (s, 1H), 7.47-7.41 (m, 3H), 7.30-7.27 (m, 3H), 7.00-6.98 (d, J=6.5 Hz, 4H), 6.94-6.92 (d, J=8.3 Hz, 2H), 4.37 (s, 1H), 4.16 (s, 1H), 4.05-4.01 (m, 2H), 3.89-3.83 (m, 2H), 3.33-3.28 (d, J=21.6 Hz, 8H), 1.91-1.86 (d, J=23.5 Hz, 3H). $^{13}$C NMR (126 MHz, Chloroform-d) δ 153.65, 152.87, 147.69, 147.08, 146.15, 138.17, 134.56, 132.84, 131.20, 128.92, 126.80, 121.21, 121.12, 118.35, 117.31, 117.25, 115.48, 109.09, 73.97, 69.30, 67.04, 50.77, 50.21, 25.74, 25.26, 16.25. DART-HRMS: m/z calcd. for $C_{28}H_{32}C_{12}N_5O_4$ [MH]$^+$, 572.1753; Found: 572.1958. IR (solid) vmax: 2916, 2848, 1546, 1510, 1462, 1450, 1375, 1225, 1197, 1037, 945, 824. Purity, Method A: 95.0%

N-(4-(4-(4-(((2S,4R)-2-(2,4-dichlorophenyl)-2-methyl-1,3-dioxolan-4-yl)methoxy)phenyl)piperazin-1-yl)phenyl)hydrazinecarboxamide (40). A solution of hydrazine hydrate (0.127 mL) and 38 (480 mg) in 1,4-dioxane (30 mL) was stirred at reflux for 3 h. After cooling to room temperature, the mixture was poured into H$_2$O and the resulting precipitate was filtered and washed with H$_2$O and isopropyl alcohol to directly provide the cis-dioxolane carboxamide 40. Yield=380 mg, 88%. 41 NMR (500 MHz, Chloroform-d) δ 8.06 (s, 1H), 7.69-7.68 (d, J=8.5 Hz, 1H), 7.47-7.45 (d, J=8.9 Hz, 1H), 7.43-7.42 (m, J=4.0 Hz, 2H), 7.25-7.23 (m, J=8.2 Hz, 2H), 7.02-6.99 (m, 2H), 6.96-6.93 (m, 2H), 6.78-6.77 (d, J=9.1 Hz, 2H), 4.66-4.64 (m, 1H), 4.36-4.33 (m, 2H), 4.01-3.98 (dd, J=9.7, 5.3 Hz, 1H), 3.80-3.74 (m, 2H), 3.33-3.25 (m, 8H), 1.90 (s, 1H), 1.83 (s, 2H). $^{13}$C NMR (126 MHz, Chloroform-d) δ 153.56, 146.98, 139.35, 132.81, 130.98, 129.40, 128.60, 126.72, 121.66, 121.21, 118.34, 118.31, 117.25, 115.24, 110.00, 109.98, 109.16, 77.28, 77.03, 76.78, 75.07, 68.44, 67.40, 50.75, 50.20, 49.97, 25.90, 25.25. Xevo ESI-HRMS: m/z calcd. for $C_{28}H_{32}C_{12}N_5O_4$ [MH]$^+$, 572.1753; Found: 572.1711. IR (solid) vmax: 2920, 2876, 2851, 1554, 1511, 1464, 1450, 1377, 1225, 1184, 1151, 1035, 944, 826. Purity, Method A: 100%

4-(4-(4-(4-(02R,4R)-2-(2,4-dichlorophenyl)-2-methyl-1,3-dioxolan-4-yl)methoxy)phenyl)piperazin-1-yl)phenyl)-1H-1,2,4-triazol-5(4H)-one (41). A solution of formamidine acetate (364 mg) and 39 (400 mg) in anhydrous DMF (30 mL) was stirred at 130° C. for 3 h. The mixture was cooled to room temperature and diluted with H$_2$O at which point a light brown precipitate formed. The solid was filtered and washed with CHCl$_3$ to provide trans-dioxolane triazolone 41. Yield=187 mg, 46%. $^1$H NMR (500 MHz, Chloroform-d) δ 7.67-7.65 (d, J=8.3 Hz, 1H), 7.50-7.48 (d, J=8.7 Hz, 1H), 7.45-7.44 (d, J=8.6 Hz, 2H), 7.29-7.27 (d, J=8.4 Hz, 1H), 7.09-7.06 (m, 1H), 7.00-6.98 (d, J=7.8 Hz, 33H), 6.94 (s, 2H), 4.37 (s, 1H), 4.18-4.15 (m, 1H), 4.07-4.00 (m, 2H), 3.91-3.87 (t, J=7.5 Hz, 1H), 3.42 (s, 1H), 3.35 (s, 2H), 3.28 (s, 4H), 1.86 (s, 3H). $^{13}$C NMR (126 MHz, Chloroform-d) δ 162.76, 158.68, 145.98, 138.29, 136.45, 134.64, 132.84, 131.20, 128.91, 126.80, 123.99, 121.47, 118.41, 117.33, 116.86, 116.69, 115.51, 109.29, 77.29, 77.03, 76.78, 73.96, 69.30, 67.02, 50.71, 49.79, 49.67, 49.17, 25.73. Xevo ESI-HRMS: m/z calcd. for $C_{29}H_{29}C_{12}N_5O_4$ [MH]$^+$, 582.1597; Found: 582.1666 IR (solid) vmax: 2958, 1687, 1509, 1227, 1191, 1036, 941, 819, 455. Purity, Method A: 95.7%

4-(4-(4-(4-(((2S,4R)-2-(2,4-dichlorophenyl)-2-methyl-1,3-dioxolan-4-yl)methoxy)phenyl)piperazin-1-yl)phenyl)-1H-1,2,4-triazol-5(4H)-one (42). A solution of formamidine acetate (mL) and 40 (380 mg) in anhydrous DMF (30 mL) was stirred at 130° C. for 3 h. The mixture was cooled to room temperature and diluted with H$_2$O at which point a light brown precipitate formed. The solid was filtered and washed with CHCl$_3$ to provide cis-dioxolane triazolone 42. Yield=78 mg, 20%. $^1$H NMR (500 MHz, Chloroform-d) δ 8.57-8.55 (d, J=11.6 Hz, 1H), 8.37 (s, 1H), 7.69-7.67 (d, J=8.5 Hz, 1H), 7.56-7.54 (d, J=11.0 Hz, 1H), 7.50-7.48 (d, J=8.9 Hz, 2H), 7.43-7.42 (s, J=2.0, 2H), 7.25-7.23 (dd, J=8.4, 7.2 Hz, 2H), 7.12 (s, 1H), 7.08-7.06 (d, J=8.8 Hz, 1H), 7.01-6.98 (m, 2H), 6.95-6.93 (d, J=8.8 Hz, 2H), 6.78-6.77 (d, J=8.9 Hz, 2H), 4.66-4.64 (m, 1H), 4.36-4.33 (m, 1H), 4.01-3.98 (m, 1H), 3.80-3.76 (m, 2H), 3.34-3.25 (m, 8H), 1.86 (s, 1H), 1.83 (s, 2H). $^{13}$C NMR (126 MHz, Chloroform-d) δ 162.70, 158.66, 152.78, 149.48, 148.66, 146.00, 139.41, 134.36, 132.81, 131.03, 128.58, 126.71, 121.48, 118.36, 117.32, 116.86, 115.27, 109.17, 75.07, 68.45, 67.38, 50.70, 49.78, 49.65, 29.72, 25.90. DART-HRMS: m/z calcd. for $C_{29}H_{30}C_{12}N_5O_4$ [MH]$^+$, 582.1597; Found: 582.1728. IR (solid) vmax: 2961, 1510, 1258, 1022, 1016, 794. Purity, Method A: 97.1%.

Biological Assay Protocols.

General Information for Cell Culture Studies Protocols for general cell culture, qPCR, and Hh inhibition ASZ cells are as previously described. (Pace et al, J. Med. Chem. 2016, 59 (8), 3635-3649; Banerjee et al. Bioorg. Med. Chem. Lett. 2012, 22 (3), 1330-1334. Protocols for the initiation and growth of Math1-Cre-ER; Ptc$^{fl/fl}$ medulloblastoma tumors, isolation, and in vitro culture of MERP MB cells, and the antiproliferation and qPCR studies carried out in these cells were previously described. (Brun et al., Oncogene 2015, 34 (29), 3770-3779; Mishra et al., J. Phys.: Conf Ser. 2014, 534 (1), 012029; Heeres et al., J. Med. Chem. 1984, 27 (7), 894-900. Data was analyzed using GraphPad Prism 5 and reported values represent mean SEM for at least two separated experiments carried out in triplicate.

Example B: Posaconazole (PSZ) Analogues

Posaconazole (PSZ, Scheme P1) is a second generation azole antifungal that has been identified as a Hedgehog (Hh) signaling pathway inhibitor with anti-cancer properties. The Hh-signaling pathway plays an essential role in embryonic development by regulating the proliferation and differentiation of cells in a time-dependent manner. Hh signaling is significantly less activate in adults with the exception of maintaining stem cell homeostasis predominately in the skin and the central nervous system. Inappropriate activation of the Hh signaling pathway has been implicated in several cancers most notably basal cell carcinoma (BCC) and medulloblastoma (MB). This aberrant Hh pathway activation is thought to be caused by genetic mutations to several key proteins involved in the pathway including Patch (Ptch), Smoothened (Smo), and Suppressor of fused (Sufu) proteins. Current FDA approved BCC drugs target Smo to inhibit Hh activation, however, drug resistance due to specific point mutations in the binding pocket of Smo has been observed in patients who have experienced recurrence of the disease. PSZ is thought to directly bind to Smo, as well, but has been shown to inhibit Hh activation in the presence of mutant Smo because it binds in a distinct manner from other Hh pathway inhibitors that function through Smo antagonism.

Heretofore, focus has been on improving the anti-Hh activity and drug-like properties of ITZ. ITZ is a first generation azole anti-fungal that was identified as a Hh-signaling pathway inhibitor during a screening of FDA-approved drugs with intentions of re-purposing. Structure activity relationship (SAR) studies of ITZ was conduced to determine functionality and stereochemistry of the scaffold for Hh inhibition. However, a pitfall of the ITZ scaffold not resolved through SAR is the poor metabolic stability of the dioxolane ring present in the structure. The PSZ scaffold overcomes this by containing a more metabolically stable THF ring instead. The study below focused on the synthesis and evaluation of des-triazole PSZ analogues utilizing structural modification determined through the studies of ITZ. Additionally, a homology model of Smo was built and used for molecular dynamics studies that correlated the modifications made to the scaffold to the observed anti-Hh activity of the ligands in BCC cells.

Example 2. Preparation of Des-Triazole PSZ Analogues

Based on SAR study focused on the ITZ scaffold, it has been determined that removal of the triazole moiety completely abolished the ability for ITZ to inhibit CYP3A4 while having no effect on its ability to inhibit Hh signaling. Therefore, an initial proof-of-concept des-triazole PSZ analogue that, for ease of synthesis, utilized the optimal ITZ side chain was synthesized. By modifying a previously published synthesis of PSZ by Saksena et. al., compound P1 (Scheme P2) was successfully synthesized. Starting with 1,3-difluorobenzene (P2) and succinic anhydride (P3), a Friedel-Craft reaction followed by a Wittig reaction produced the corresponding alkene (P4). Subsequently, an amidation reaction using (4R)-(+)-4-benzyl-2-oxazolidi-none (OXZ) made intermediate P5. The OXZ group facili- Scheme P1. Initial SAR for the PSZ scaffold and proof-of-concept Des-triazole PSZ analogue that led to subsequent analogues.

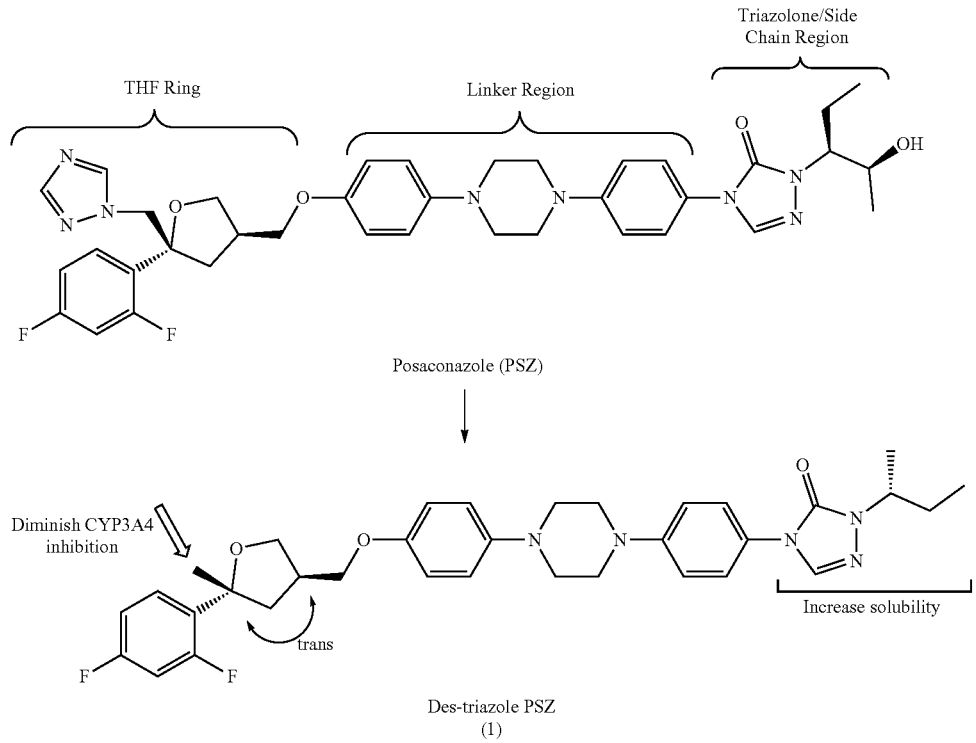

tated selective hydroxymethylation in the presence of titanium tetrachloride to form intermediate P6. Iodocyclization provided the 2S, 4R conformation of the THF ring (7). stereochemical assignment of position 4 from the 4R tosylate (P7) to the final trans-2S,4S conformation. The synthesis of the linker region is well established in the literature.

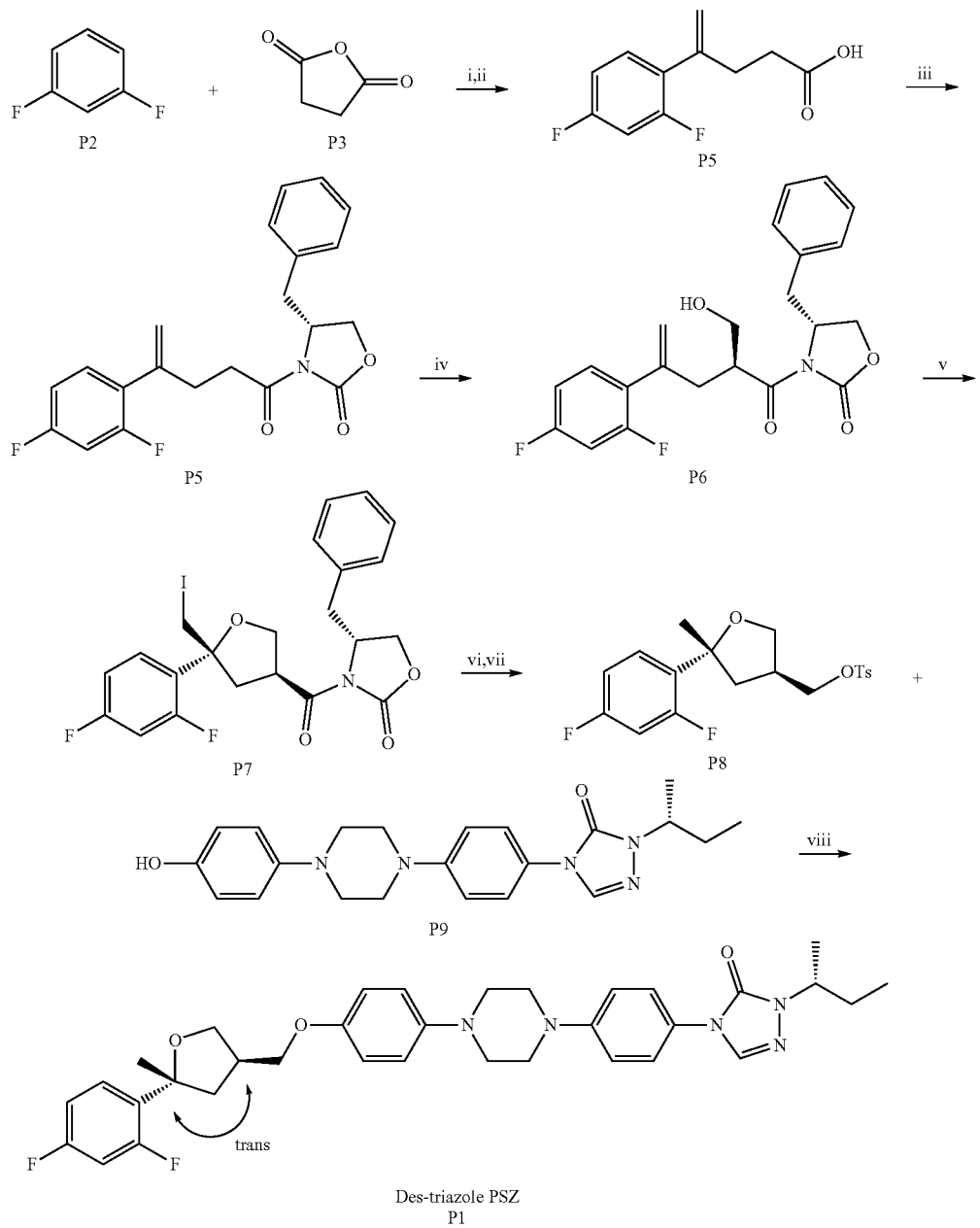

Scheme P2. Synthesis of THF Ring for Des-PSZ Analogues.[a]

Des-triazole PSZ
P1

[a]Reagents and conditions: i) AlCl$_3$, DCM, 45° C., 3-4 h, 65%, ii) NaOtBu, MePPh$_3$Br, THF, 40° C., 12 h, 100%; iii) a) DMC, TEA, pivaloyl chloride, b) OXZ, DMAP, DMF, 45-50° C., 12 h, 68%; iv) a) DCM, TiCl$_4$, DIPEA, 0° C., 1 h, b) s-trioxane, TiCl$_4$, DCM, 0° C., 12 h, 50%; v) I$_2$, pyridine, CH$_3$CN, R.T., 20 h, 61%; vi) NaBH$_4$, DMSO, 110° C., 12 h, 62%; vii) Pyridine, TsCl, R.T., 12 h, 100%; viii) Linker region/triazolone region, Cs$_2$CO$_3$, DMSO, 90° C., 12 h, 63%.

Reduction with sodium borohydride removed the iodine and deprotected the alcohol to allow tosylation yielding intermediate P8. Subsequent coupling of the linker/side chain region (P9) at yielded the final desired product, P1, with the trans conformation in an overall yield of 5%. Coupling of the THF region to the linker/side chain phenol reverses the Anti-Hh activity of PSZ and des-triazole PSZ (P1) were determined by measuring their ability to down-regulate Hh-dependent Gli1 mRNA expression in ASZ cells, a well-characterized Hh-dependent murine BCC cell line (Table P1). Additionally, CYP3A4 inhibition and P-glycoprotein (P-gp) efflux of each compound were evaluated. Compound P1 was 2.5 times more potent than PSZ with an IC$_{50}$ of 0.19

μM. As expected removal of the triazole ring to make compound 1 decreased CYP3A4 inhibition. Surprisingly, while PSZ is a substrate for P-gp, P1 was not suggesting another improvement in the PSZ scaffold.

TABLE P1

In Vitro and Pharmacokinetic Activity of PSZ and initial Des-triazole PSZ Analogue.

| Compound | $IC_{50}$ (μM)[a, b] | MERP | [c]CYP3A4 $IC_{50}$ (μM) | [d]P-gp (Efflux) | Metabolic Stability |
|---|---|---|---|---|---|
| PSZ | 0.50 ± 0.1 | 1.5 ± 0.3 | 0.15 | Efflux | |
| P1 | 0.19 ± 0.03 | 0.61 ± 0.12 | >20 | No Efflux | |

[a]$IC_{50}$ values represent the Mean ± SEM of at least two separate experiments performed in triplicate.
[b]All analogues evaluated following 48 h incubation.[c]

Molecular modeling (MD) of for PSZ and des-triazole PSZ with SMO was then used to further validate the experimental biological activity for each compounds as well as further guide SAR of the PSZ scaffold. The modeling was conducted using the D. E. Shaw Desmond molecular dynamics software available through Schrodinger. Because no known crystal structure of PSZ (or ITZ) bound to human Smo exists, a homology model of Smo was built from several previously reported crystal structures bound to known Smo inhibitors (PDB 4QIM: Anta XV; PDB 4O9R: cyclopamine; PDB 4JRV: 4C; and PDB 4N4W: SANT-1). The 2-D ligand contact maps of PSZ and compound P1 detail the major interactions that occur per simulation time. For both molecules, the triazole region is oriented extracellularly with the linker/side chain region reaching intracellularly into the Smo binding pocket. This may explain why removal of the triazole ring from des-triazole PSZ P1 did not affect anti-Hh activity of the compound. This was also observed within the ITZ SAR previously conducted. Rather, an increase in anti-Hh activity in the ASZ cell assay was observed for des-triazole PSZ P1 suggesting that removal of the triazole ring may have allowed it to fit deeper into the pocket and make more favorable interactions when compared to PSZ. This deeper penetration of the pocket is evidenced by the hydrogen bond interaction between the triazolone oxygen of P1 with ARG400 that is maintained 99% of the time. In contrast, the side chain hydroxyl and the triazolone oxygen of PSZ make two strong hydrogen bond interactions with ASP473 and ASP384 at 76% and 100% of the simulation time, respectively that are found in a more shallow part of the binding pocket of SMO. Des-triazole PSZ also makes additional favorable water bridged hydrogen bond interactions between the THF oxygen and linker oxygen and GLU208 (58%) and GLU481 (46%), respectively, that may contribute to its increase anti-Hh activity. This was not observed with PSZ. Therefore, not wishing to be bound by theory, but it may be concluded that these molecule benefitted from the removal of the triazole ring and that by introducing potential hydrogen bonding moieties in the triazolone/side chain region of future des-triazole PSZ analogues anti-Hh activity can be maintained or increased as well as improve pharmacokinetic properties, such as solubility, of the scaffold.

Although the original PSZ side chain group, (2S,3S)-2-hydroxypentan-3-yl, would increase solubility and introduce a hydrogen bonding group, choice of simplified carboxylic acid and alcohol side chains that required less synthetic steps and avoided difficulty stereochemistry were taken. Des-triazole PSZ analogues P13-P15 were synthesized according to Scheme P3. The methoxy-protected linker P10 was coupled under basic conditions to either ethyl 3-bromopropanoate or ethyl bromoacetate to yield esters P11 and P12. Demethylation to form the corresponding phenols (P11 and P12) was achieved using BBr3. Subsequent coupling of the tosylated THF ring afforded compounds P13 and P14 which due to the basic conditions and elevated temperature were hydrolyzed to the acid. Analogue P13 was further reduced using $LiAlH_4$ to make the corresponding alcohol, P15. Interested in the effect the propanoic acid side chain on the anti-Hh activity of the des-triazole ITZ scaffold, the nonsteriochemically defined compound, 117, was synthesized (Scheme 14).

Scheme P3. Synthesis of Carboxylic Acid and Alcohol Side Chain Des-PSZ Analogues.[a]

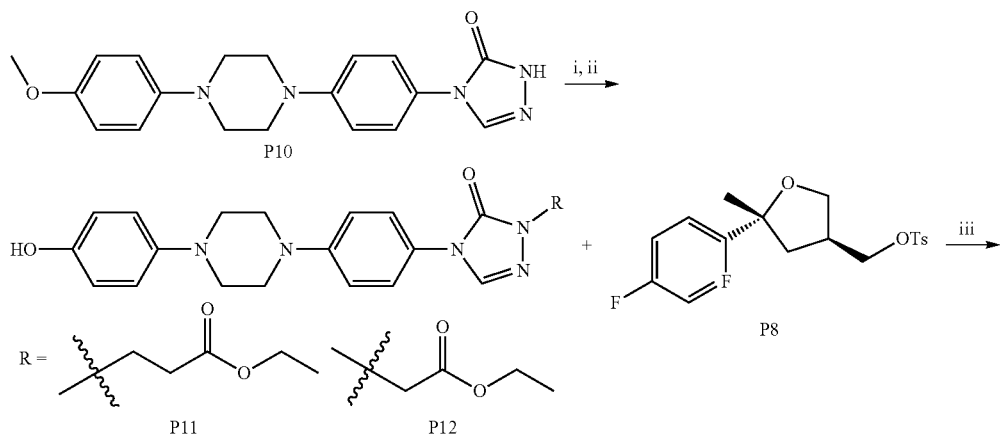

-continued

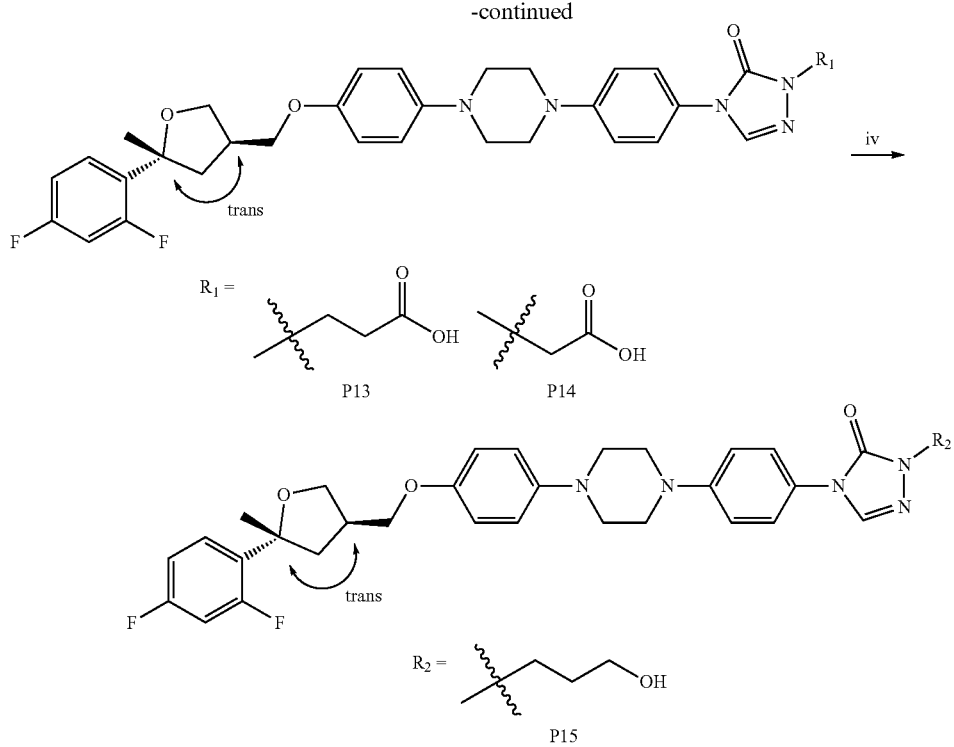

aReagents and conditions: i) ethyl 3-bromopropanoate or ethyl bromoacetate, Cs2CO3, DMF, 60° C.-100° C., O/N, ~100%; ii) BBr3 (1M), DCM, 0° C.-R.T., 4 h, 29-35%; iii) Cs2CO3, DMSO, 90° C., O/N, 36%; iv) LiAlH4, THF, 0° C. to R.T., 63%.

Scheme I4. Synthesis of Des-triazole ITZ Carboxylic Acid Side Chain.[a]

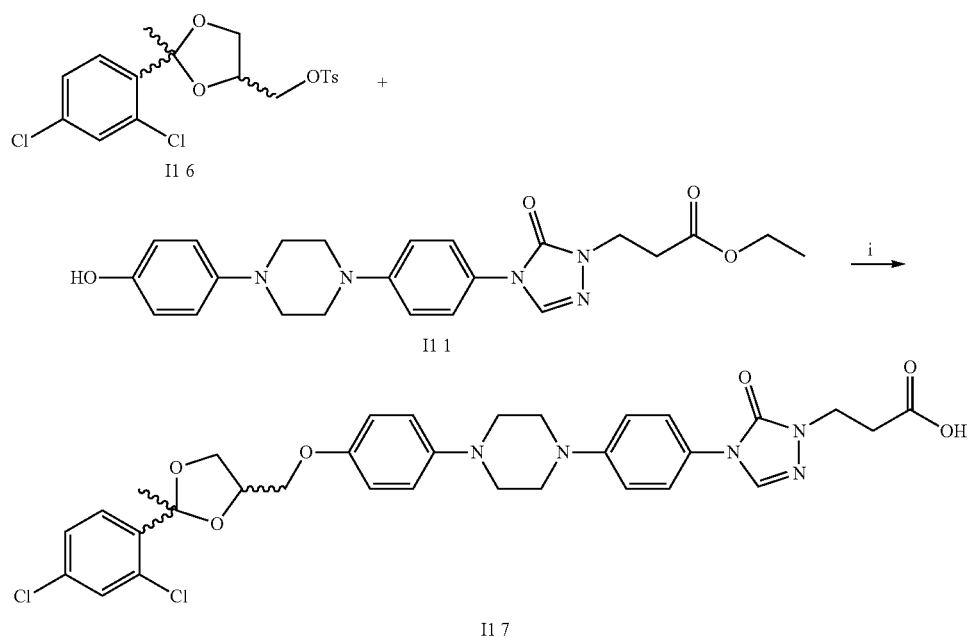

[a]i) Cs2CO3, DMSO, 90° C., O/N, 54%

Based on ITZ SAR studies, it was determined that the cis conformation of the ITZ carboxamide intermediate inhibited Gli expression in ASZ at $IC_{50}$=0.009 μM. Although the synthesis of the des-triazole THF ring allows for only the trans conformation, there is still interest in the anti-Hh activity of these intermediates. Therefore, des-triazole PSZ intermediates, P19-P23, were synthesized (Scheme P5) to determine whether this SAR was applicable to the PSZ scaffold. As part of the linker synthesis, commercially available 4-(piperazin-1-yl)phenol and 1-chloro-4-nitrobenzene are coupled to make a nitro-substituted linker with a methoxy protecting group on the other end of the molecule. Removal of the methoxy with hydrobromic acid produced the corresponding phenol (P18) and allowed for coupling of P8 to make nitro des-triazole PSZ intermediate, P19. The nitro intermediate is then reduced in presence of 10% Pd/C and hydrazine monohydrate to produce the aniline intermediate, P20. The carbamate intermediate, P21, was generated through the addition of phenyl chloroformate to aniline P20, followed by treatment with hydrazide monohydrate to yield the carboxamide intermediate P22. The final unsubstituted triazolone intermediate, P23, was generated by heating carboxamide P22 with formamidine acetate.

Scheme P5. Synthesis of Des-triazole PSZ Triazolone Precursors.[a]

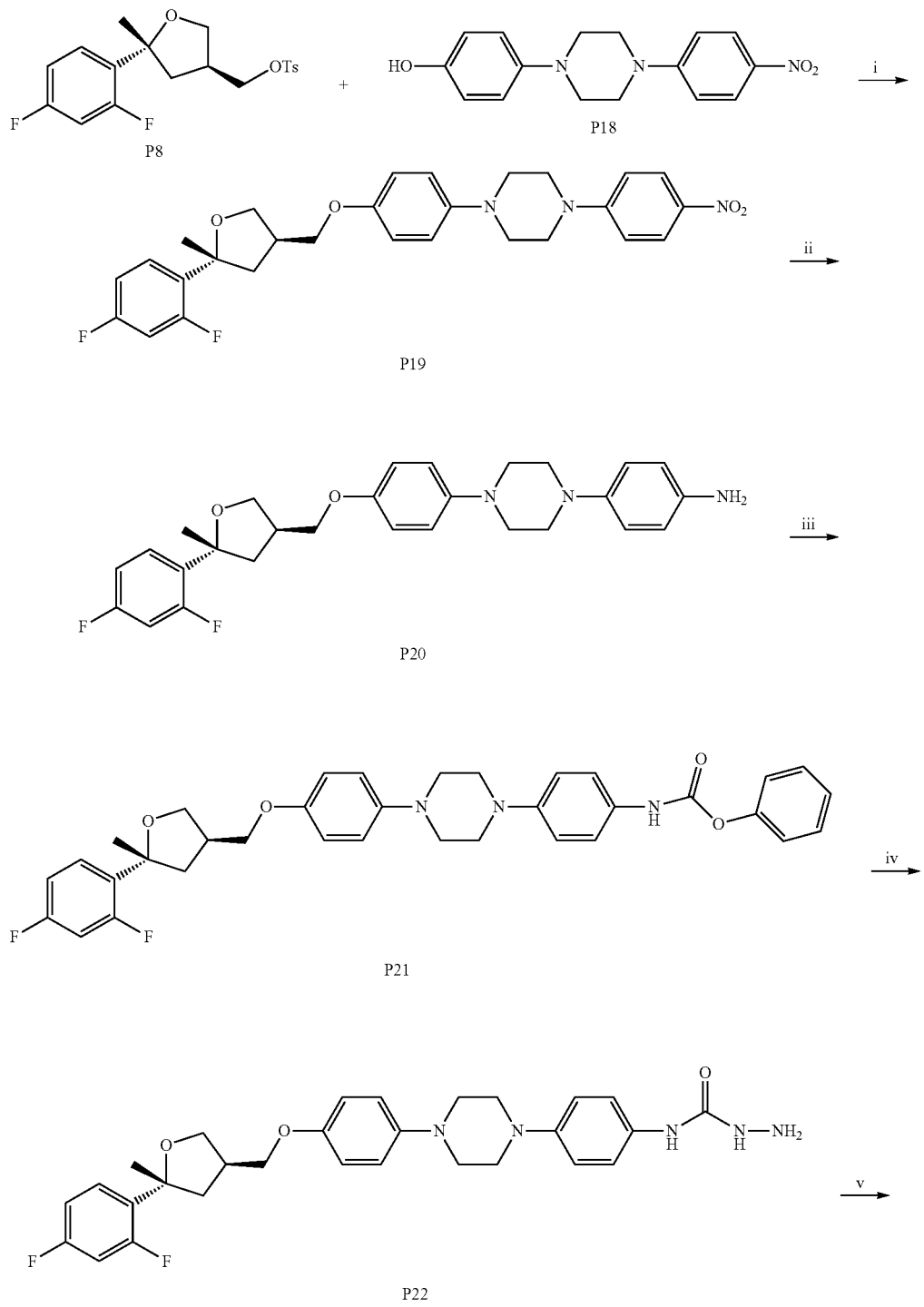

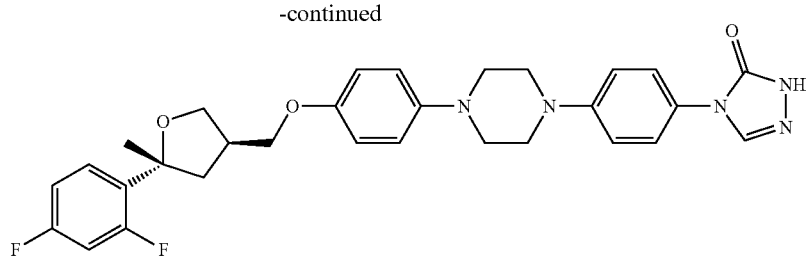

P23

<sup>a</sup>Reagents and conditions: i) Cs₂CO₃, DMSO, 90° C., O/N, 67%; ii) 10% Pd/C, EtOH, NH₂NH₂, reflux, O/N, 90%; iii) Pyr (17 eq), ClCOOPh (1.1 eq), 3 h, 40%; iv) NH₂NH₂—H₂O (5.5 eq), reflux, 3 h, 30%; v) formamidine acetate (4.5 eq), acetic acid, reflux, 3 h, 46%.

A previous study identified three des-triazole ITZ amide analogues containing either a 3-acetyl phenyl ($IC_{50}$=0.089 µM), 3-phenol ($IC_{50}$=0.16 µM), or 3-pyridyl ($IC_{50}$=0.19 µM) as potent Hh inhibitors in ASZ cells. The des-triazole PSZ version of these amide analogues were then synthesized using peptide coupling conditions. In Scheme P6, the aniline intermediate P20 and 3-acetyl benzoic acid, 3-hydroxybenzoic acid, or nicotinic acid were subjected to one of two sets of conditions [1-ethyl-3-(3-dimethylaminopropyl)carbon-iimide (EDCI) and 4-dimethylaminopyridine (DMAP) or N-methylmorpholine (NMM) and 1-[bis(dimethylamino)methylene]-1H-1,2,3-triazolo[4,5,6]pyridinium3-oxid-hexafluorophosphate (HATU)] to yield analogues P24, P25 and P26, respectively.

TABLE P2

In Vitro and Pharmacokinetic Activity of Des-triazole PSZ Analogues.

| Compound | $IC_{50}$ (µM)[a, b] | Solubility (µM) | [c]CYP3A4 $IC_{50}$ (µM) | PAMPA | Metabolic Stability |
|---|---|---|---|---|---|
| P13 | 0.032 ± 0.01 | ZZ | ZZ | ZZ | ZZ |
| P14 | 0.15 ± 0.02 | | | | |
| P15 | 0.020 ± 0.01 | | | | |
| I17 | 0.012 ± 0.005 | | | | |
| P19 | 0.74 ± 0.15 | | | | |
| P20 | 0.33 ± 0.12 | | | | |

Scheme P6. Synthesis of Des-triazole PSZ Amide Analogues.<sup>a</sup>

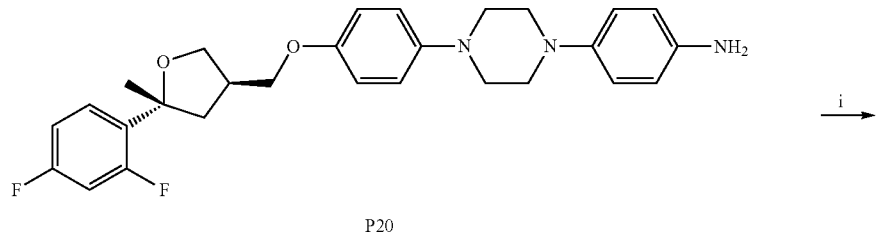

P20

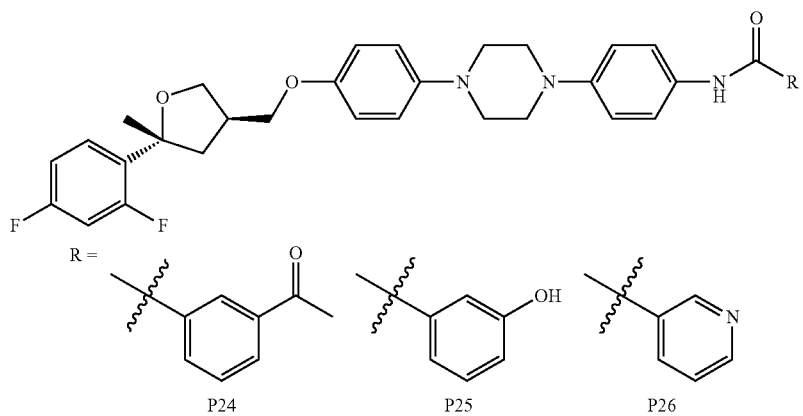

<sup>a</sup>Reagents and conditions: i) (a) EDCI, DMAP, DCM, RT, 12 h, 27-63% or (b) HATU, NMM, DMF, RT, 12 h, 80%.

TABLE P2-continued

In Vitro and Pharmacokinetic Activity
of Des-triazole PSZ Analogues.

| Compound | IC$_{50}$ (μM)$^{a, b}$ | Solubility (μM) | $^c$CYP3A4 IC$_{50}$ (μM) | PAMPA | Metabolic Stability |
| --- | --- | --- | --- | --- | --- |
| P21 | Inactive (>10) | | | | |
| P22 | 0.22 ± 0.08 | | | | |
| P23 | 0.19 ± 0.10 | | | | |
| P24 | 0.024 ± 0.009 | | | | |
| P25 | 0.19 ± 0.03 | | | | |
| P26 | 0.038 | | | | |

$^a$IC$_{50}$ values represent the Mean ± SEM of at least two separate experiments performed in triplicate.
$^b$All analogues evaluated following 48 h incubation.

Experimental Chemical Synthesis

General Information. Starting materials were purchased from Sigma-Aldrich or Fisher Scientific. All solvents including anhydrous solvents were purchased from Fisher Scientific or Sigma-Aldrich. All reactions were run under an argon atmosphere. The linker and ITZ side chain synthesis have been previously published in Pace et. al. The THF ring synthesis was previously published and performed with minor modifications. NMR data was collected on a Bruker AVANCE 500 MHz spectrometer and analysis performed using MestReNova. HRMS data was obtained at the Mass Spectrometry Facility at the University of Connecticut. FT-IR analysis was performed on a Bruker Alpha Platinum ATR instrument using OPUS software (v 7.2). All PSZ analogues evaluated in the biological assays were greater than 95% purity. Purity was determined by injecting 25 μL of a 1 mg/mL solution each PSZ analogues dissolved in HPLC-grade MeCN into an Agilent Manual FL-Injection Valve (600 bar) on an Agilent 1100/1200 Series HPLC equipped with an Agilent Eclipse Plus C18 (4.6×100 mm) column and Agilent 1100 Series Photodiode Array Detector. The mobile phase consisted of 70% MeCN/30% H$_2$O. All analogues were run at a flow rate of 1.0 mL/min for 12 min and purity was assessed at 254 nm.

General Synthesis for Coupling of THF Ring to Linker Region PSZ analogues Cs$_2$CO$_3$ (10 equiv.) and linker (1 equiv.) were diluted in anhydrous DMSO and stirred for 30 minutes at room temperature before the addition of the linker region (P8). The reaction was heated to 90° C. and stirred overnight. In the case of P13 and P14, the esters were hydrolyzed to the acid after coupling. The next day, the reaction was quenched with water and extracted using EtOAc (2×) and DCM (2×). In the case of P13 and P14, the water layer had to be acidified to pH=2 to ensure extraction of the acid product. The organic layers were combined, dried over Na$_2$SO$_4$, filtered and concentrated. The crude was purified by column chromatography (SiO$_2$, 10-30% Acetone in Hexanes). The fractions containing product were collected and dried by rotary evaporation.

3-(4-(4-(4-(4-(((3R,5R)-5-(2,4-difluorophenyl)-5-methyltetrahydrofuran-3-yl)methoxy)phenyl)piperazin-1-yl)phenyl)-5-oxo-4,5-dihydro-1H-1,2,4-triazol-1-yl)propanoic acid P13. White solid. (Yield=42%) $^1$HNMR (500 MHz, CDCl$_3$) δ 7.63 (s, 1H), 7.59-7.51 (m, 2H), 7.45-7.43 (d, J=8.9 Hz, 1H), 7.08-7.06 (d, J=9.0 Hz, 2H), 7.00-6.97 (m, 3H), 6.90-6.79 (m, 5H), 4.29-4.21 (m, 1H), 4.14-4.07 (m, 1H), 4.03-3.91 (m, 4H), 3.8-3.72 (m, 1H), 3.42-3.40 (m, 3H), 3.32-3.31 (m, 1H), 3.28-3.27 (m, 4H), 2.71-2.51 (m, 3H), 2.11-1.97 (m, 2H), 1.66 (s, 1H), 1.65 (s, 2H). $^{13}$CNMR (126 MHz, CDCl$_3$) δ 176.37, 162.98, 161.01, 153.50, 152.29, 150.77, 145.57, 134.42, 127.72, 125.49, 123.73, 118.69, 118.60, 118.04, 116.67, 116.50, 115.31, 110.79, 110.63, 110.01, 109.98, 104.57, 104.36, 104.16, 82.80, 77.32, 77.06, 76.81, 70.43, 70.16, 70.10, 50.77, 50.21, 49.12, 48.00, 42.99, 42.04, 39.51, 39.42, 36.79, 29.71, 28.36, 20.87. DART-HRMS: m/z [M+H]$^+$ cald. for [C$_{33}$H$_{36}$F$_2$N$_5$O$_5$]$^+$, 620.2060; found [M 114.9653]$^+$, 505.2407 m/z. IR (solid) νmax: 2931, 1705, 1614, 1512, 1231.6, 1039, 966, 822. Purity=95.1%.

2-(4-(4-(4-(4-(((3R,5R)-5-(2,4-difluorophenyl)-5-methyltetrahydrofuran-3-yl)methoxy)phenyl)piperazin-1-yl)phenyl)-5-oxo-4,5-dihydro-1H-1,2,4-triazol-1-yl)acetic acid P14. Tan solid. (Yield=27%)$^1$H NMR (500 MHz, CDCl$_3$) δ 7.63-7.51 (m, 1H), 7.00-6.94 (m, 5H), 6.90-6.88 (m, 3H), 6.81-6.79 (m, 2H), 4.29-4.26 (m, 1H), 4.14-4.11 (m, 1H), 3.99-3.94 (m, 3H), 3.87-3.72 (m, 2H), 3.40 (s, 1H), 3.33-3.26 (m, 8H), 2.65-2.62 (m, 2H), 1.98 (d, J=4.3 Hz, 1H), 1.65 (s, 2H), 1.58 (s, 1H), 1.30 (s, 3H). $^{13}$CNMR (126 MHz, CDCl$_3$) δ 163.11, 161.01, 153.31, 148.19, 145.76, 129.69, 127.65, 118.49, 117.91, 116.63, 115.30, 110.79, 110.61, 104.57, 104.36, 104.15, 82.71, 70.12, 50.80, 50.08, 42.07, 39.54, 29.72, 28.36. DART-HRMS: m/z [M+H]$^+$ cald. for [C$_{32}$H$_{34}$F$_2$N$_5$O$_5$]$^+$, 606.2450; found [M 101.0026]$^+$, 505.2424 m/z. IR (solid) νmax: 2928, 2854, 2229, 1614, 1511, 1230, 966, 823; Purity=97.2%

3-(4-(4-(4-(4-((2-(2,4-dichlorophenyl)-2-methyl-1,3-dioxolan-4-yl)methoxy)phenyl)piperazin-1-yl)phenyl)-5-oxo-4,5-dihydro-1H-1,2,4-triazol-1-yl)propanoic acid 117. White solid. (Yield=20 mg, 54%)$^1$H NMR (500 MHz, CDCl$_3$) δ 7.78-7.76 (d, J=8.4 Hz, 1H), 7.69-7.62 (m, 2H), 7.57 (s, 1H), 7.45-7.39 (m, 2H), 7.29-7.23 (m, 1H), 7.08-7.06 (m, 1H), 7.00-6.98 (s, 2H), 6.95-6.93 (m, 2H), 6.78-6.77 (m, 1H), 4.67-4.64 (m, 1H), 4.42-4.33 (m, 2H), 4.19-4.14 (m, 1H), 4.07-4.00 (m, 2H), 3.91-3.77 (m, 2H), 3.42-3.39 (m, 3H), 3.30-3.25 (m, 5H), 1.86 (s, 3H). $^{13}$C NMR (126 MHz, CDCl$_3$) δ 153.06, 153.06, 152.54, 152.54, 150.80, 150.75, 147.98, 145.94, 145.94, 139.35, 139.13, 138.14, 134.63, 134.58, 132.84, 132.77, 131.21, 131.16, 130.98, 129.00, 128.91, 128.59, 126.81, 126.75, 125.49, 123.70, 123.62, 118.50, 118.46, 118.42, 117.92, 116.66, 115.52, 115.27, 110.00, 109.17, 109.11, 77.30, 77.05, 76.79, 75.07, 75.07, 74.77, 74.77, 73.96, 73.96, 73.62, 73.62, 69.29, 69.29, 68.43, 68.43, 67.94, 67.37, 67.37, 67.31, 67.01, 67.01, 50.73, 50.64, 50.64, 50.14, 49.16, 49.16, 48.23, 48.23, 47.25, 31.61, 29.72, 25.90, 25.74, 25.74, 25.66, 22.67. DART-HRMS: m/z [M+H]$^+$ cald. for [C$_{32}$H$_{34}$Cl$_2$N$_5$O$_6$]$^+$, 654.1808; found [M 115.0225]$^+$, 539.1583 m/z. IR (solid) νmax: 2937, 2881, 2826, 1705, 1509, 1225, 1193, 1034, 819, 731, 500. Purity=30.1%: 69.0% (cis: trans), total=99.1%.

2-((R)-sec-butyl)-4-(4-(4-(4-(((3R,5R)-5-(2,4-difluorophenyl)-5-methyltetrahydrofuran-3-yl)methoxy)phenyl)-piperazin-1-yl)phenyl)-2,4-dihydro-3H-1,2,4-triazol-3-one P1. Dark grey solid. (Yield=63%). $^1$H NMR (500 MHz, CDCl$_3$) δ 7.66 (s, 1H), 7.59-7.54 (dd, J=16.2, 8.2 Hz, 1H), 7.48-7.46 (d, J=8.5 Hz, 2H), 7.08-7.06 (d, J=8.5 Hz, 2H), 6.98 (m, 1H), 6.90-6.89 (d, J=7.6 Hz, 3H), 6.85-6.80 (m, 1H), 4.34 (m, 1H), 4.14-4.11 (t, J=7.7 Hz, 1H), 3.97-3.96 (m, 3H), 3.85-3.74 (m, 1H), 3.41 (m, 4H), 3.28 (m, 4H), 2.64-2.62 (m, 2H), 2.10-1.87 (m, 2H), 1.79-1.75 (m, 1H), 1.65 (s, 3H), 1.44-1.43 (d, J=6.7 Hz, 3H), 0.95 (t, J=7.3 Hz, 3H). $^{13}$CNMR (126 MHz, CDCl$_3$) δ 152.08, 150.59, 145.72, 127.74, 127.66, 125.98, 123.59, 118.57, 116.70, 115.32, 104.50, 104.36, 104.15, 82.80, 70.16, 52.72, 50.75, 49.27, 42.07, 39.54, 29.72, 28.47, 28.39, 19.27, 10.81. DART-HRMS: m/z [M+H]$^+$ cald. for [C$_{34}$H$_{40}$F$_2$N$_5$O$_3$]$^+$, 604.3021;

found 604.3085. IR (solid) vmax: 2932, 2842, 1702, 1513, 1230, 1041, 966, 823. Purity=95.1%.

1-(4-(((3R,5R)-5-(2,4-difluorophenyl)-5-methyltetrahydrofuran-3-yl)methoxy)phenyl)-4-(4-nitrophenyl)piperazine P19. $Cs_2CO_3$ (445 mg, 1.26 mmol, 10 equiv.) and 4-(4-(4-nitrophenyl)piperazin-1-yl)phenol (38 mg, 0.126 mmol, 1 equiv.) were diluted in anhydrous DMSO (10 mL) and stirred for 30 minutes at room temperature before the addition of P8 (45 mg, 0.126 mmol, 1 equiv.). The reaction was heated to 90° C. and stirred overnight. The next day, the reaction was quenched with water and extracted using EtOAc (3×). The organic layers were combined, dried over $Na_2SO_4$, filtered and concentrated. The crude was purified by column chromatography ($SiO_2$, 10-30% Acetone in Hexanes). The fractions containing product were collected and dried by rotary evaporation. Orange oil. (Yield=40 mg, 67%). $^1$H NMR (500 MHz, $CDCl_3$) δ 8.21-8.19 (m, 2H), 7.65-7.51 (m, 1H), 6.98-6.80 (m, 8H), 4.29-4.26 (m, 1H), 4.19-4.10 (m, 1H), 4.00-3.94 (m, 2H), 3.87-3.72 (m, 1H), 3.63-3.60 (m, 4H), 3.28-3.26 (m, 4H), 2.98-2.95 (m, 1H), 2.66-2.52 (m, 2H), 2.07-1.95 (m, 1H), 1.65 (s, 1H), 1.58 (s, 2H). $^{13}$CNMR (126 MHz, $CDCl_3$) δ 154.79, 145.38, 130.16, 127.72, 127.64, 126.99, 125.98, 118.68, 115.38, 115.33, 113.38, 112.92, 104.36, 104.15, 82.81, 70.19, 70.08, 69.90, 60.31, 50.47, 47.29, 42.03, 39.53, 28.37. DART-HRMS: m/z $[M+H]^+$ cald. for $[C_{28}H_{30}F_2N_3O_4]^+$, 510.2126; found 510.2205. IR (solid) vmax: 2932, 2850, 1596, 1509, 1322, 1229, 1115, 1038, 944, 826, 754. Purity=95.6%.

4-(4-(4-(((3R,5R)-5-(2,4-difluorophenyl)-5-methyltetrahydrofuran-3-yl)methoxy)phenyl)piperazin-1-yl)aniline P20. To a dry round bottom flask purged with $Ar_{(g)}$, Pd/C (10 wt. %, 0.05 equiv.) followed by ethanol was added. P19 (20 mg, 0.04 mmol, 1 equiv.) was then added to the flask followed by dropwise addition of hydrazine monohydrate (13 mg, 0.40 mmol, 0.013 mL, 10 equiv.). The reaction was refluxed overnight. The next day, the reaction was cooled, filtered through celite and washed with ethanol. The filtrate was dried by rotary evaporation to give a grey solid. The crude was purified by column chromatography ($SiO_2$, 20-30% Acetone in Hexanes). The fractions containing product were collected and dried by rotary evaporation. White solid. (Yield=17 mg, 90%). $^1$H NMR (500 MHz, $CDCl_3$) δ 7.65-7.54 (m, 1H), 6.99-6.97 (m, 2H), 6.92-6.85 (m, 5H), 6.83-6.79 (m, 2H), 6.73-6.71 (m, 2H), 4.29-4.26 (m, 1H), 4.14-4.11 (m, 1H), 3.97-3.94 (m, 3H), 3.81-3.72 (m, 1H), 3.49 (br, s, 1H), 3.27-3.23 (m, 8H), 2.63-2.62 (m, 2H), 2.00-1.95 (m, 1H), 1.65 (s, 3H), 1.58 (s, 1H). $^{13}$CNMR (126 MHz, $CDCl_3$) δ 162.97, 158.04, 153.12, 145.98, 144.46, 140.40, 127.74, 127.67, 118.86, 118.34, 116.24, 115.27, 115.22, 110.80, 110.61, 104.56, 104.35, 104.15, 82.70, 70.20, 70.14, 69.92, 51.26, 50.92, 42.06, 39.77, 39.55, 29.72, 28.38. DART-HRMS: m/z $[M+H]^+$ cald. for $[C_{28}H_{32}F_2N_3O_2]^+$, 480.2384; found 480.2450. IR (solid) vmax: 3459, 3364, 2974, 2821, 1614, 1510, 1496, 1221, 1038, 942, 819, 515. Purity=98.1%.

phenyl (4-(4-(4-(((3R,5R)-5-(2,4-difluorophenyl)-5-methyltetrahydrofuran-3-yl)methoxy)phenyl)piperazin-1-yl)phenyl)carbamate P21. P20 (100 mg, 0.42 mmol, 1 equiv.) was diluted in $CHCl_3$ (15 mL) under $Ar_{(g)}$ followed by the addition of pyridine (6.72 mmol, 0.27 mL, 16 equiv.). The solution was then cooled to 0° C. and phenylchloroformate (33 mg, 0.42 mmol, 0.025 mL, 1 equiv.) was added dropwise. The reaction was stirred at room temperature for 3 hours. When complete, the reaction was diluted with water and extracted using DCM (3×). The crude was purified by column chromatography ($SiO_2$, 20-30% Acetone in Hexanes). The fractions containing product were collected and dried by rotary evaporation. White solid. (Yield=50 mg, 40%). $^1$H NMR (500 MHz, $CDCl_3$) δ 7.65-7.54 (m, 1H), 7.45-7.40 (m, 4H), 7.29-7.23 (m, 3H), 7.02-6.94 (m, 4H), 6.89-6.88 (m, 3H), 6.86-6.79 (m, 1H), 4.30-4.27 (dd, J=8.5, 7.5 Hz, 1H), 4.14-4.11 (m, 1H), 4.00-3.94 (m, 2H), 3.87-3.72 (m, 1H), 3.35-3.32 (m, 4H), 3.28-3.25 (m, 4H), 2.99-2.94 (m, 1H), 2.67-2.61 (m, 1H), 2.56-2.52 (m, 1H), 2.07-1.98 (m, 1H), 1.65 (s, 2H), 1.58 (s, 1H). $^{13}$CNMR (126 MHz, $CDCl_3$) δ 159.99, 158.02, 153.26, 150.76, 145.82, 129.39, 127.69, 125.59, 121.67, 120.34, 118.46, 118.42, 117.16, 115.31, 115.31, 115.26, 110.81, 110.64, 104.36, 104.15, 82.71, 70.21, 70.13, 69.92, 50.81, 49.98, 42.06, 39.77, 39.56, 28.39. DART-HRMS: m/z $[M+H]^+$ cald. for $[C_{35}H_{36}F_2N_3O_4]^+$, 600.2596; found 600.2595. IR (solid) vmax: 3334, 3295, 3044, 2966, 2831, 1707, 1534, 1488, 1197, 1030, 820, 687. Purity=96.2%.

N-(4-(4-(4-(((3R,5R)-5-(2,4-difluorophenyl)-5-methyltetrahydrofuran-3-yl)methoxy)phenyl)piperazin-1-yl)phenyl)hydrazinecarboxamide P22. P21 (40 mg, 0.067 mmol, 1 equiv.) was dissolved in 1,4-dioxane (2 mL). To the solution, hydrazine monohydrate (12 mg, 0.36 mmol, 0.011 mL, 5.4 equiv.) was added and the reaction was refluxed for 3 hours. When complete, the reaction cooled to room temperature, poured into water and extracted with EtOAc (3×). The organic layers were combined, dried over $Na_2SO_4$, filtered and concentrated. The crude was purified by column chromatography ($SiO_2$, 20-30% Acetone in Hexanes). The fractions containing product were collected and dried by rotary evaporation. Tan solid. (Yield=10.4 mg, 30%). $^1$H NMR (500 MHz, $CDCl_3$) δ 8.08 (s, 1H), 7.61 (s, 1H), 7.57-7.54 (m, 1H), 7.47-7.46 (d, J=8.0 Hz, 2H), 7.01-6.94 (m, 3H), 6.89-6.79 (m, 3H), 4.29-4.26 (t, J=7.3 Hz, 1H), 4.14-4.11 (t, J=7.0 Hz, 1H), 3.97 (br, s, 2H), 3.88-3.72 (m, 1H), 3.40 (s, 1H), 3.32-3.27 (m, 7H), 2.98-2.95 (m, 1H), 2.63-2.62 (m, 1H), 2.56-2.52 (m, 1H), 1.65 (s, 2H), 1.57 (s, 1H). $^{13}$CNMR (126 MHz, $CDCl_3$) δ 162.97, 153.71, 147.67, 147.11, 145.91, 131.06, 127.74, 121.17, 118.43, 117.25, 115.28, 115.24, 104.36, 104.15, 70.19, 70.13, 69.91, 50.84, 50.21, 42.05, 39.76, 39.54, 28.38, 25.26. DART-HRMS: m/z $[M+H]^+$ cald. for $[C_{29}H_{34}F_2N_5O_3]^+$, 538.2551; found. IR (solid) vmax: 3349, 3206, 2927, 2874, 2819, 1677, 1508, 1223, 1014, 817, 625, 516. Purity=96.7%

4-(4-(4-(4-(((3R,5R)-5-(2,4-difluorophenyl)-5-methyltetrahydrofuran-3-yl)methoxy)phenyl)piperazin-1-yl)phenyl)-2,4-dihydro-3H-1,2,4-triazol-3-one P23. A solution of formamidine acetate (8.7 mg, 0.084 mmol, 4.5 equiv.) and P22 (10 mg, 0.019 mmol, 1 equiv.) in anhydrous DMF (5 mL) were stirred at 130° C. for 3-5 hours. The mixture was then cooled to room temperature, diluted with water, and extracted with EtOAc (3×). The organic layers were combined, dried over $Na_2SO_4$, filtered and concentrated. The crude was purified by column chromatography ($SiO_2$, 15-30% Acetone in Hexanes). The fractions containing product were collected and dried by rotary evaporation. Tan solid. (Yield=4.7 mg, 46%). $^1$H NMR (500 MHz, $CDCl_3$) δ 8.57-8.54 (d, J=11.6 Hz, 1H), 8.38 (s, 1H), 7.63-7.48 (m, 2H), 7.26-7.23 (d, J=11.5 Hz, 1H), 7.06-6.79 (m, 8H), 4.29-4.26 (m, 1H), 4.14-4.11 (m, 1H), 3.98-3.94 (m, 2H), 3.87-3.72 (m, 1H), 3.40 (s, 1H), 3.37-3.27 (m, 7H), 2.63-2.51 (m, 2H), 2.08-1.90 (m, 1H) 1.65 (s, 1H), 1.58 (s, 2H). $^{13}$CNMR (126 MHz, $CDCl_3$) δ 162.54, 158.58, 153.28, 148.76, 129.35, 127.68, 121.57, 121.41, 118.48, 117.31, 116.85, 115.31, 104.36, 70.20, 50.77, 49.79, 49.65, 42.08, 39.55, 29.72, 28.38. DART-HRMS: m/z $[M+H]^+$ cald. for $[C_{30}H_{32}F_2N_5O_3]^+$, 548.2395; IR (solid) vmax: 2923, 2852, 1690, 1509, 1226, 1076, 1018, 966, 944, 816, 730, 516. Purity=96.7%

4-(4-(4-(4-(((3R,5R)-5-(2,4-difluorophenyl)-5-methyltetrahydrofuran-3-yl)methoxy)phenyl)piperazin-1-yl)phenyl)-2-(3-hydroxypropyl)-2,4-dihydro-3H-1,2,4-triazol-3-one P15. P13 (24 mg, 0.039 mmol, 1 equiv.) was diluted in THF (5 mL) and cooled to 0° C. 2M LiAlH$_4$ (0.062 mmol, 0.031 mL, 2 equiv.) was added dropwise. The reaction was warmed to room temperature and stirred for 3-4 hrs. When complete, the reaction flask was placed on ice and saturated NH$_4$Cl was added dropwise. The product was using EtOAc (3×). The organic layers were combined, dried over Na$_2$SO$_4$, filtered and concentrated. The crude was purified by column chromatography (SiO$_2$, 1% MeOH in DCM). The fractions containing product were collected and dried by rotary evaporation. Tan solid. (Yield=17 mg, 87%). $^1$H NMR (500 MHz, CDCl$_3$) δ 7.64 (s, 1H), 7.61-7.52 (m, 2H), 7.44-7.43 (d, J=8.9 Hz, 1H), 7.07-7.06 (d, J=9.1 Hz, 1H), 7.00-6.97 (m, 4H), 6.89-6.87 (m, 3H), 6.82-6.79 (m, 2H), 4.29-4.21 (m, 1H), 4.14-4.07 (m, 2H), 4.03-3.91 (m, 4H), 3.87-3.71 (m, 2H), 3.40 (m, 2H), 3.31 (m, 2H), 3.27 (s, 4H), 2.63-2.62 (m, 3H), 2.12-1.98 (m, 2H), 1.65 (s, 3H), 1.37-1.33 (dd, J=13.6, 6.7 Hz, 2H). $^{13}$CNMR (126 MHz, CDCl$_3$) δ 163.04, 161.11, 160.07, 158.01, 153.39, 152.22, 150.77, 148.03, 145.76, 134.29, 127.73, 123.64, 118.58, 118.50, 117.92, 116.65, 116.61, 115.31, 111.50, 110.78, 110.63, 110.01, 109.98, 104.57, 104.36, 104.15, 82.74, 77.29, 77.03, 76.78, 70.46, 70.19, 70.12, 69.90, 50.81, 50.73, 50.11, 49.19, 47.98, 43.01, 42.05, 39.54, 39.45, 28.38, 22.35, 14.07. DART-HRMS: m/z [M+H]$^+$ cald. for [C$_{33}$H$_{38}$F$_2$N$_5$O$_4$]$^+$, 605.2814; found [M 100.0.390]$^+$, 505.2424. IR (solid) vmax: 2932, 2828, 2232, 1689, 1614, 1511, 1230, 1112, 1039, 966, 821. Purity=96.2%.

N-(4-(4-(4-(((3R,5R)-5-(2,4-difluorophenyl)-5-methyltetrahydrofuran-3-yl)methoxy)phenyl)piperazin-1-yl)phenyl)-3-hydroxybenzamide (P25): To a dry round bottom flask purged with Ar$_{(g)}$, 3-hydroxybenzoic acid (4 mg, 0.03 mmol, 1 equiv.) and HATU (15 mg, 0.04 mmol, 1.2 equiv.) were added and then diluted with DMF (5 mL). Next, NMM (12 mg, 0.12 mmol, 0.013 mL, 4 equiv.) was added and the mixture was stirred at room temperature for 30 minutes followed by the addition of P20 (16 mg, 0.03 mmol, 1 equiv.). The reaction was stirred at room temperature overnight. When complete, the reaction was added to ice cold water (~5 mL) and extracted with EtOAc (3×). The organic layers were combined, dried over Na$_2$SO$_4$, filtered and concentrated. The crude was purified by column chromatography (SiO$_2$, 30% Acetone in Hexanes). The fractions containing product were collected and dried by rotary evaporation. White solid. (Yield=10 mg, 80%). $^1$H NMR (500 MHz, CDCl$_3$) δ 8.18-8.10 (m, 1H), 7.83-7.54 (m, 5H), 7.44-7.39 (m, 2H), 7.91-7.17 (d, J=7.3 Hz, 1H), 7.09-6.79 (m, 7H), 4.28-4.26 (m, 1H), 4.12-4.10 (t, J=7.8 Hz, 1H), 3.97 (m, 2H), 3.81-3.74 (m, 1H), 3.39-3.27 (m, 8H), 3.19-2.93 (m, 2H), 2.66-2.53 (m, 2H), 1.65 (s, 2H), 1.57 (s, 1H). $^{13}$CNMR (126 MHz, CDCl$_3$) δ 156.31, 155.97, 153.28, 151.10, 148.63, 145.86, 136.88, 130.03, 127.79, 122.69, 121.73, 121.19, 118.61, 118.49, 116.92, 115.31, 104.36, 104.15, 82.71, 70.20, 70.13, 50.79, 49.81, 42.05, 39.55, 29.72, 28.37. DART-HRMS: m/z cald. for [C$_{35}$H$_{36}$F$_2$N$_3$O$_4$]$^+$, 600.2596; found 600.2681. IR (solid) vmax: 3269, 2925, 2825, 1676, 1642, 1511, 1225, 1020, 817, 731, 685, 590, 532, 516. Purity=100%.

N-(4-(4-(4-(((3R,5R)-5-(2,4-difluorophenyl)-5-methyltetrahydrofuran-3-yl)methoxy)phenyl)piperazin-1-yl)phenyl)nicotinamide (P26): To a dry round bottom flask purged with Ar$_{(g)}$, P20 (15 mg, 0.031 mmol, 1 equiv.), nicotinic acid (12 mg, 0.09 mmol, 3 equiv.), N-(3-dimethylaminopropyl)-N'-ethylcarbodiimide hydrochloride (EDCI) (17 mg, 0.09 mmol, 3 equiv.) and 4-dimethylaminopyridine (11 mg, 0.09 mmol, 3 equiv.) were added together and diluted in DCM (8 mL). The reaction was stirred overnight at room temperature. When complete, the reaction flask diluted with water and extracted with DCM (3×). The organic layers were combined, dried over Na$_2$SO$_4$, filtered and concentrated. The crude was purified by column chromatography (SiO$_2$, 30% Acetone in Hexanes). The fractions containing product were collected and dried by rotary evaporation. White solid. (Yield=11.4 mg, 63%). $^1$H NMR (500 MHz, CDCl$_3$) δ 9.13 (s, 1H), 8.81 (d, J=3.3 Hz, 1H), 8.25-8.24 (d, J=7.6 Hz, 1H), 7.87 (s, 1H), 7.60-7.47 (m, 4H), 7.05-6.79 (m, 7H), 4.29-4.26 (dd, J=8.7, 7.3 Hz, 1H), 4.14-4.11 (dd, J=8.6, 7.4 Hz, 1H), 3.99-3.94 (m, 2H), 3.85-3.74 (m, 1H), 3.39-3.36 (m, 4H), 3.29-3.27 (m, 4H), 2.99-2.94 (m, 1H), 2.67-2.52 (m, 2H), 2.07-1.95 (m, 1H), 1.65 (s, 2H), 1.58 (s, 1H). $^{13}$CNMR (126 MHz, CDCl$_3$) δ 163.63, 162.98, 161.17, 153.29, 152.43, 148.83, 147.81, 145.82, 135.26, 130.97, 129.92, 127.62, 123.68, 121.93, 118.49, 116.82, 115.30, 110.78, 110.65, 104.57, 104.36, 104.15, 82.74, 70.20, 70.13, 50.79, 49.72, 42.05, 39.55, 28.39. DART-HRMS: m/z [M+H]$^+$ cald. for [C$_{34}$H$_{35}$F$_2$N$_4$O$_3$]$^+$, 585.2599; found 585.2649. IR (solid) vmax: 3312, 2932, 2874, 2826, 1737, 1646, 1614, 1592, 1242, 966, 945, 849, 748. Purity=97.4%.

3-acetyl-N-(4-(4-(4-(((3R,5R)-5-(2,4-difluorophenyl)-5-methyltetrahydrofuran-3-yl)methoxy)phenyl)piperazin-1-yl)phenyl)benzamide (P24). To a dry round bottom flask purged with Ar$_{(g)}$, P20 (17 mg, 0.035 mmol, 1 equiv.), 3-acetyl benzoic acid (18 mg, 0.11 mmol, 3 equiv.), N-(3-dimethylaminopropyl)-N'-ethylcarbodiimide hydrochloride (EDCI) (21 mg, 0.11 mmol, 3 equiv.) and 4-dimethylaminopyridine (13 mg, 0.11 mmol, 3 equiv.) were added and diluted with DCM (8 mL). The reaction was stirred overnight at room temperature. When complete, the reaction flask diluted with water and extracted with DCM (3×). The organic layers were combined, dried over Na$_2$SO$_4$, filtered and concentrated. The crude was purified by column chromatography (SiO$_2$, 30% Acetone in Hexanes). The fractions containing product were collected and dried by rotary evaporation. White solid. (Yield=5.2 mg, 27%). $^1$H NMR (500 MHz, CDCl$_3$) δ 8.48 (s, 1H), 8.18-8.16 (m, 2H), 7.85 (s, 1H), 7.68-7.54 (m, 4H), 7.06-6.80 (m, 7H), 4.30-4.27 (dd, J=8.7, 7.3 Hz, 1H), 4.14-4.11 (m, 1H), 4.00-3.94 (m, 2H), 3.87-3.73 (m, 1H), 3.40-3.37 (m, 4H), 3.30-3.28 (m, 4H), 2.73 (s, 3H), 2.65-2.53 (m, 2H), 2.07-1.95 (m, 1H), 1.65 (s, 3H). $^{13}$CNMR (126 MHz, CDCl$_3$) δ 197.40, 164.45, 162.98, 161.01, 160.08, 158.02, 153.28, 148.70, 145.85, 137.41, 135.64, 131.74, 131.38, 130.19, 129.28, 127.69, 126.29, 121.80, 118.49, 118.45, 116.87, 115.31, 115.26, 104.56, 104.36, 104.15, 82.71, 70.20, 70.13, 69.92, 50.80, 49.78, 42.05, 39.77, 39.55, 29.72, 28.38, 26.77. DART-HRMS: m/z [M+H]$^+$ cald. for [C$_{37}$H$_{38}$F$_2$N$_3$O$_4$]$^+$, 626.2752; found 626.2807. IR (solid) vmax: 3305, 2944, 2830, 1642, 1591, 1511, 1497, 1227, 1023, 818, 706, 537, 515. Purity=100%.

Biological Assay Protocols.

General Information for Cell Culture Studies. Protocols for general cell culture, qPCR, and Hh inhibition ASZ cells are as previously described. Protocols for the initiation and growth of Math1-Cre-ER; Ptc$^{fl/fl}$ medulloblastoma tumors, isolation, and in vitro culture of MERP MB cells, and the antiproliferation and qPCR studies carried out in these cells were previously described. Data was analyzed using GraphPad Prism 5 and reported values represent mean SEM for at least two separated experiments carried out in triplicate.

Example 3. Preparation of Liposome Formulation: Medulloblastoma

There is tremendous promise in utilizing nanotechnology to attain more targeted treatment regimens for both pediatric and brain cancers. Liposomes are the most studied form of nanotechnology and ITZ has been experimentally formulated into liposomes for the treatment of various fungal infections. If ITZ or ITZ analogues are going to be used for the treatment of Medulloblastoma, they must be able to penetrate the blood brain barrier (BBB) and reach the brain. Due to their large size, it is anticipated that ITZ and the ITZ analogues may have trouble crossing the BBB and liposomes serve as a viable option for achieving this targeted drug delivery. Modifying the characteristics of liposomes, such as size and composition, can aid in the nanoparticles' ability to cross the BBB. Liposomes containing ITZ or ITZ analogues would be advantageous for the targeted treatment of pediatric SHH subtype MB. Liposomes were formulated utilizing the coaxial turbulent jet in co-flow instrument, hydrogenated soy phosphatidyl choline (HSPC; 900 mg), 1,2-distearoyl-phosphatidylethanolamine-methyl-polyethylene glycol-2000 (DSPE mPEG-2000; 300 mg), cholesterol (300 mg), and ITZ (60 mg) were dissolved in EtOH (100 mL) with the help of slight heating (50° C.) and sonication. In parallel, four liters of a 6.6 mM $KH_2PO_4$ solution were prepared and adjusted to pH 6. Lipid solution was added to stainless steel tank within the coaxial turbulent jet apparatus and this solution were incubated at 50° C. to ensure lipids and drug remains in solution. The aqueous solution was attached to the apparatus within its preparation container. The lipid concentration and lipid formulation were added into the computer program and the flow rates were set. Liposome size and poly-dispersion index (PDI) were measured with Malvern Zetasizer Nano S and liposomes were collected in 50 mL eppendorf centrifuge tubes. Liposome samples were stored at 4° C.

Free Drug Separation: Free ITZ was separated from liposomes by centrifugation. Liposomes were centrifuged in a Beckman J2-HC centrifuge at 13,000 rpm for 90 minutes in a 4° C. environment. Liposomes were decanted leaving behind a pellet containing free drug.

Determination of Encapsulation Efficiency: After removal of free drug, the percentage of drug encapsulated into liposomes was determined with a UV spectrophotometer (BioTek Synergy H1 Hybrid Reader). Liposomes were lysed with 5% triton and heat (60° C.) for 2 hours. The concentration of ITZ was determined by measuring UV at 254 nm in triplicate and comparing to a standard curve of ITZ.

It is important to determine the amount of drug encapsulated into the liposomes. Encapsulation efficiency is described as the concentration of the incorporated material (in this instance ITZ) detected in the formulation over the initial concentration used to make the formulation. Lysing the liposomes and measuring drug content via UV or fluorescence detection can determine the drug concentration. When comparing to a standard curve of drug, the concentration can be determined. The absorbance of various concentrations of ITZ was measured using a UV-vis-spectrophotometer at 254 nm. Plotting absorbance versus concentration created a standard curve of ITZ (Appendix A). After removal of free drug via centrifugation, the liposomes were lysed to release ITZ. ITZ liposomes were lysed with 5% Triton solution and heated for 2 h at 60° C. Upon heating for shorter time periods (20 min), less ITZ was released from the liposomes. This may be due to the way ITZ is being encapsulated into the lipid bilayer of the liposome or the way it is interacting with the other lipids. Absorbance of these liposome samples was measured and concentrations of drug released were determined by using the slope equation of the standard curve. Drug concentrations ranged from 115.3 µg/mL 162.2 µg/mL. If 100% of ITZ were encapsulated into the collected volume of liposomes, the concentration would be 171 m/mL. The encapsulation efficiency of ITZ into this liposome formulation was averaged to be 80.2%. The ITZ encapsulation efficiency is reported in Table 10.

$$\text{Encapsulation Efficiency} = \frac{\text{Total drug} - \text{free drug}}{\text{Total drug}} \times 100\%$$

TABLE 10

| ITZ Encapsulation Efficiency | | | |
|---|---|---|---|
| ITZ Concentration (µg/mL) | Encapsulation Efficiency (%) | ITZ Concentration (µg/mL) | Encapsulation Efficiency (%) |
| 162.2 | 94.8 | 124.7 | 72.9 |
| 146.9 | 85.9 | 147.9 | 86.5 |
| 115.3 | 67.4 | 124.6 | 72.8 |
| 138.6 | 81.1 | | |

Gene Expression Assay Protocol (ASZ-001): Cells are seeded (10,000 cells per well; 100 µL total volume per well) in a 96-well tissue culture plate. After 24 h of incubation (37° C., 5% $CO_2$), growth media was removed and replaced with low FBS media. Cells were incubated for an additional 24 h. After this time, DMSO (vehicle control) and liposomes (Aqueous Solution) were added to the wells. Cells were incubated (37° C., 5% $CO_2$) for 48 h and RNA was isolated and evaluated by qRT-PCR.

Rt-PCR Protocol: Following treatment and incubation periods, both RNA extraction and cDNA synthesis were performed using a TaqMan Cells-to-CT (fast) kit. cDNA synthesis utilized a BioRad MyCycler and was programmed according to the manufacturer's instructions. Quantitative RT-PCR was performed on an ABI 7500 system and made use of the following TaqMan Gene Expression Probes: mouse ActB (Mm00607939_s1) and mouse Gli1 (Mm00494654_m1). Relative gene expression levels were computed via ΔΔCT method using GraphPad Prism. Corresponding $IC_{50}$ values were calculated as mean±SEM for at least three separate experiments performed in triplicate.

ITZ liposomes, empty liposomes, and free ITZ were evaluated in the gene expression assay in ASZ cells. Instead of immediately lysing cells after 48 h incubation with drug or liposomes, cells were lysed at various time points (24 h, 48 h, 72 h, 96 h) to determine if liposomes exhibited anti-Hh activity in a similar manner to free drug. Evaluation of Hh pathway inhibition at various time points was performed as it is unknown how long it would take ITZ-liposomes to enter the cell and release drug. Two subsequent time course experiments were performed, each exploring different concentrations of liposomes and free drug. Data suggested that the empty liposomes were upregulating the Hh pathway (48 h and 72 h) and as a result, empty liposomes were further examined in our preliminary MEF cell line.

Due to ASZ results, it was hypothesized that the cholesterol component of the liposome formulation was upregulating the Hh pathway. Oxysterols, oxidated forms of cholesterol, are known to upregulate the Hh pathway and are a well-characterized method to activate Hh signaling in MEFs. Due to cholesterol having a similar steroidal structure to oxysterols, it needed to be determined if the liposomes themselves were having an affect on the Hh pathway. Empty liposomes, centrifuged and not centrifuged, were treated in a gene expression assay with MEF cells. This cell line does not have aberrant Hh signaling and therefore these cells need to typically be treated with upregulators (Hh ligand or oxysterols). Cells were only treated with empty liposomes at various volumes and it was determined that they did not exhibit activity. Water was set to "100% Gli1 Activation" despite the pathway not being very active. Empty liposomes that were centrifuged and not centrifuged exhibited similar Gli1 values to water indicating that the liposomes themselves were not activating or deactivating Gli1 in C3H10T1/2 cells.

After determining that the liposomes themselves were not upregulating the Hh pathway, ITZ liposomes were tested in a dose dependent manner alongside free ITZ. Two liposome samples were utilized: one that was centrifuged and one that was not centrifuged. Both liposome samples were tested to confirm removal of free ITZ; there should be a difference in activity between liposomes alone and liposomes with free drug. At two different time points (48 h and 96 h) results indicated that the most potent compound was free ITZ, followed by non-centrifuged liposomes, and then centrifuged liposomes. ITZ potently inhibited the Hh pathway ($IC_{50}$=0.11±0.025 μM at 48 h) followed by liposome+free drug treatment ($IC_{50}$=0.49±0.04 μM at 48 h) and liposome treatment ($IC_{50}$=2.5±0.37 μM at 48 h). There is a trend in this data indicating that the liposomes that had not been subjected to centrifugation were more potent than ITZ liposomes that were centrifuged (Table 11). This further confirms that free drug was removed with the centrifugation method. It is important to note that at 96 h, liposome potency slightly increased ($IC_{50}$=1.04±0.17 μM) in comparison to 48 h ($IC_{50}$=2.5±0.37 μM) indicating that more drug may have been released during this longer incubation period resulting in increased Hh inhibitory activity (Table 11).

TABLE 11

In Vitro Analysis of Liposomes

| Treatment | $IC_{50}$ (μM) 48 h[a,b] | $IC_{50}$ (μM) 96 h[a,c] |
|---|---|---|
| ITZ | 0.11 ± 0.025 | 0.14 ± 0.012 |
| Liposomes | 2.5 ± 0.37 | 1.04 ± 0.17 |
| Liposomes + ITZ | 0.49 ± 0.04 | 0.45 ± 0.26 |

[a]$IC_{50}$ and $GI_{50}$ values represent the Mean ± SEM of at least two separate experiments performed in triplicate.
[b]All analogues evaluated following 48 hr incubation.
[c]All analogues evaluated following 96 hr incubation.

These liposomes demonstrated reduced anti-Hh activity in comparison to free ITZ. It is important to note that cell penetration assays were not performed and this could explain the difference in potency between free drug and liposomes. The liposome formulation could be optimized to increase cell permeability. The use of proteins to tag liposomes and target them to the BBB and the use of cationic liposomes may increase ability to interact with cells.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another. The terms "comprising", "having", "including", and "containing" are to be construed as open-ended terms (i.e., meaning "including, but not limited to") unless otherwise noted. All ranges disclosed herein are inclusive of the endpoints, and the endpoints are independently combinable with each other. Each range disclosed herein constitutes a disclosure of any point or sub-range lying within the disclosed range. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed.

As used herein the terms "analog" and "analogue" may be used interchangeably.

All patents, published patent applications and other documents cited herein are expressly incorporated herein in their entirety to the same extent as if each document or cited publication was individually and expressly incorporated herein. If a term in the present application contradicts or conflicts with a term in an incorporated reference, the term from the present application takes precedence over the conflicting term from the incorporated reference. While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A compound having the structure of Formula (I)

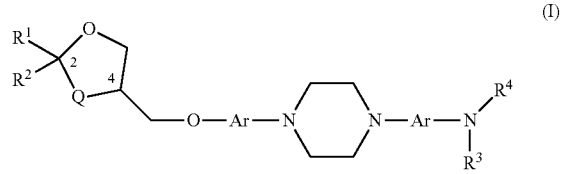

wherein
Q is O or $CH_2$;
each Ar is independently unsubstituted or substituted aryl;
$R^1$ is methyl;
$R^2$ is unsubstituted or substituted aryl;
$R^3$ is H or unsubstituted or substituted $C_{1-6}$ alkyl;
$R^4$ is —C(=O)—$R^5$, C(=O)—O—$R^5$, or —S(=O)$_n$—$R^5$, wherein $R^5$ is $C_{1-6}$ alkyl, unsubstituted or substituted $C_{3-7}$ cycloalkyl, unsubstituted or substituted aryl, unsubstituted or substituted heteroaryl, and n is 0, 1, or 2; or $R^4$ is H or unsubstituted or substituted $C_{1-6}$ alkyl; or $R^3$ and $R^4$ along with the nitrogen atom form a nitro ($NO_2$) group; or $R^3$ and $R^4$ join to form an unsubstituted or substituted 5- or 6-membered ring with the proviso that it does not contain a —N-(=J)-N— moiety where J is O or S;
wherein the substituted groups are substituted with 1, 2, or 3 substituents, each substituent is independently $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl;
a pharmaceutically acceptable salt, a stereoisomeric form thereof, or a combination thereof.

2. The compound of claim 1, wherein Q is O; and each Ar is phenyl, pyridine, pyrazine, or pyridazine.

3. The compound of claim 1, wherein each Ar is phenyl.

4. The compound of claim 1, wherein $R^2$ is unsubstituted or substituted phenyl.

5. The compound of claim 1, wherein is 2,4-dichlorophenyl or 2,4-difluorophenyl.

6. The compound of claim 1, wherein $R^4$ is —C(=O)—$R^5$ or —S(=O)$_n$—$R^5$.

7. The compound of claim 6, wherein $R^5$ is unsubstituted or substituted $C_{3-7}$ cycloalkyl, unsubstituted or substituted aryl, unsubstituted or substituted heteroaryl.

8. A compound having the structure of Formula (Ia)

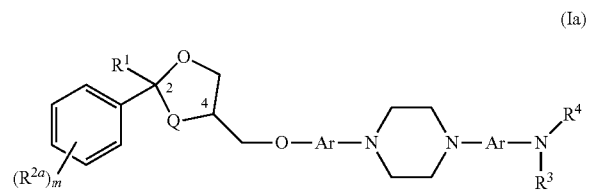

(Ia)

wherein
Q is O or $CH_2$;
each Ar is independently unsubstituted or substituted aryl;
$R^1$ is methyl;
each $R^{2a}$ independently is $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl;
m is 0, 1, 2, or 3;
$R^3$ is H or unsubstituted or substituted $C_{1-6}$ alkyl;
$R^4$ is —C(=O)—$R^5$, —C(=O)—O—$R^5$, or —S(=O)$_n$—$R^5$, wherein $R^5$ is $C_{1-6}$ alkyl, unsubstituted or substituted $C_{3-7}$ cycloalkyl, unsubstituted or substituted aryl, unsubstituted or substituted heteroaryl, and n is 0, 1, or 2; or $R^4$ is H or unsubstituted or substituted $C_{1-6}$ alkyl; or $R^3$ and $R^4$ along with the nitrogen atom form a nitro ($NO_2$) group; or $R^3$ and $R^4$ join to form an unsubstituted or substituted 5- or 6-membered ring with the proviso that it does not contain a —N-(=J)-N— moiety where J is O or S;
wherein the substituted groups are substituted with 1, 2, or 3 substituents, each substituent is independently $C_{1-6}$ alkyl, halo, —OH, —COOH, cyano, nitro, amine, $C_{1-6}$ monoalkylamine, $C_{1-6}$ dialkylamine, $C_{1-6}$ haloalkyl, $C_{1-6}$ haloalkoxy, $C_{2-6}$ alkanoyl, or $C_{1-6}$ alkoxcarbonyl;
a pharmaceutically acceptable salt, a stereoisomeric form thereof, or a combination thereof.

9. A pharmaceutical composition comprising the compound of claim 1 and optionally a pharmaceutically acceptable excipient.

10. The pharmaceutical composition of claim 9, wherein the composition is a solid dispersion of the compound and a polymer having acidic functional groups.

11. The pharmaceutical composition of claim 10, wherein the polymer comprises a polycarboxylic acid.

12. The pharmaceutical composition of claim 10, wherein the polymer comprises hydroxypropyl methylcellulose phthalate.

13. A method for the therapeutic treatment of a cell proliferation disorder in a subject in need thereof, comprising administering a therapeutically effective amount of the compound of claim 1.

14. The method of claim 13, wherein the cell proliferation disorder is dependent upon the Hh signaling pathway.

15. The method of claim 13, wherein the cell proliferation disorder is a non-cancerous cell proliferation disorder.

16. The method of claim 13, wherein the cell proliferation disorder is cancer.

17. The method of claim 16, wherein the cancer is basal cell carcinoma (BCC) or medulloblastoma (MB).

18. The method of claim 16, wherein the cancer is resistant to Vismodegib.

19. The method of claim 16, wherein the cancer is chronic myeloid leukemia, lung cancer, prostate cancer, pancreatic cancer or bone cancer.

20. A liposome formulation comprising the compound of claim 1 or a compound having the structure of Formula (II):

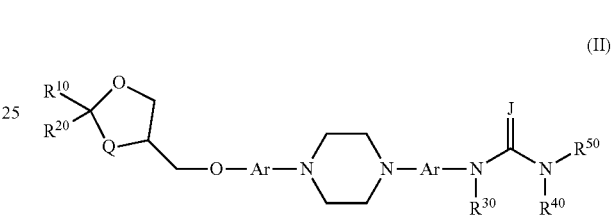

(II)

wherein
Q is O or $CH_2$;
each Ar is independently unsubstituted or substituted aryl;
J is O or S;
$R^{10}$ is methyl;
$R^{20}$ is unsubstituted or substituted aryl;
$R^{30}$ is H or unsubstituted or substituted $C_{1-6}$ alkyl;
$R^{40}$ is H or unsubstituted or substituted $C_{1-6}$ alkyl; or $R^{30}$ and $R^{40}$ join to form an unsubstituted or substituted 5- or 6-membered ring with the —N-(=J)-N— moiety where $R^{30}$ and $R^{40}$ form a unsubstituted or substituted $C_{2-3}$ carbohydryl group or a unsubstituted or substituted $C_{1-2}$ carbohydryl group linked via a nitrogen to a nitrogen of the —N-(=J)-N— moiety;
$R^{50}$ is H, substituted or unsubstituted $C_{1-6}$ alkyl, $C_{1-6}$ alkoxy, $C_{2-6}$ alkanoyl, $C_{1-6}$ alkoxcarbonyl, $C_{1-6}$ haloalkyl, wherein the substituted $C_{1-6}$ alkyl is substituted with 1, 2, or 3 substituents, each substituent is independently $C_{1-6}$ alkyl, —OH, —COOH, cyano, nitro, $C_{1-6}$ monoalkylamine, $C_{1-6}$ dialkylamine, $C_{1-6}$ haloalkyl, $C_{1-6}$ haloalkoxy;
a pharmaceutically acceptable salt, a stereoisomeric form thereof, or a combination thereof.

21. A method for the therapeutic treatment of a cell proliferation disorder in a subject in need thereof, comprising administering a therapeutically effective amount of the liposome formulation of claim 20.

22. The method of claim 21, wherein the cell proliferation disorder is dependent upon the Hh signaling pathway.

23. The method of claim 22, wherein the cell proliferation disorder is a non-cancerous cell proliferation disorder.

24. The method of claim 22, wherein the cell proliferation disorder is cancer.

25. The method of claim 24, wherein the cancer is basal cell carcinoma (BCC) or medulloblastoma (MB).

26. The method of claim 24, wherein the cancer is resistant to Vismodegib.

27. The method of claim 24, wherein the cancer is chronic myeloid leukemia, lung cancer, prostate cancer, pancreatic cancer or bone cancer.

\* \* \* \* \*